(12) United States Patent
Bigot-Corbel et al.

(10) Patent No.: US 9,915,662 B2
(45) Date of Patent: Mar. 13, 2018

(54) PROTEIN MICROARRAY FOR CHARACTERIZING THE SPECIFICITY OF THE MONOCLONAL IMMUNOGLOBULINS OF MGUS OR MYELOMA PATIENTS

(71) Applicants: Sylvie Hermouet, Nantes (FR); Edith Bigot-Corbel, Montfaucon-Montigné (FR); Delphine Feron, Pont-Saint-Martin (FR)

(72) Inventors: Edith Bigot-Corbel, Nantes (FR); Sylvie Hermouet, Nantes (FR); Delphine Feron, Nantes (FR); Cathy Charlier, Nantes (FR); Pierre Weigel, Nantes (FR); Adrien Herlédan, Lille (FR); Yannick Jacques, Nantes (FR)

(73) Assignees: Sylvie Hermouet, Nantes (FR); Edith Bigot-Corbel, Montfaucon-Montigné (FR); Delphine Feron, Pont-Saint-Martin (FR)

( * ) Notice: Subject to any disclaimer, the term of this patent is extended or adjusted under 35 U.S.C. 154(b) by 209 days.

(21) Appl. No.: 14/416,890

(22) PCT Filed: Jul. 23, 2013

(86) PCT No.: PCT/EP2013/065524
§ 371 (c)(1),
(2) Date: Jan. 23, 2015

(87) PCT Pub. No.: WO2014/016301
PCT Pub. Date: Jan. 30, 2014

(65) Prior Publication Data
US 2015/0204876 A1 Jul. 23, 2015

(30) Foreign Application Priority Data

Jul. 23, 2012 (EP) .................................. 12305896

(51) Int. Cl.
*G01N 33/577* (2006.01)
*B01J 19/00* (2006.01)
*G01N 33/569* (2006.01)
*G01N 33/574* (2006.01)
*G01N 33/576* (2006.01)
*G01N 33/68* (2006.01)

(52) U.S. Cl.
CPC ........ *G01N 33/577* (2013.01); *B01J 19/0046* (2013.01); *G01N 33/56905* (2013.01); *G01N 33/56922* (2013.01); *G01N 33/56972* (2013.01); *G01N 33/56994* (2013.01); *G01N 33/5767* (2013.01); *G01N 33/57426* (2013.01); *G01N 33/6854* (2013.01); *G01N 33/6893* (2013.01); *G01N 2333/045* (2013.01); *G01N 2333/05* (2013.01); *G01N 2333/186* (2013.01); *G01N 2333/205* (2013.01); *G01N 2333/45* (2013.01); *G01N 2800/22* (2013.01); *G01N 2800/52* (2013.01); *G01N 2800/60* (2013.01)

(58) Field of Classification Search
CPC ............. G01N 33/577; G01N 33/56905; B01J 19/0046
USPC .......................................................... 506/9
See application file for complete search history.

(56) References Cited

U.S. PATENT DOCUMENTS 5,976,807 A * 11/1999 Horlick .................. C12N 15/10 435/369
2011/0183364 A1* 7/2011 Carreno Garcia . G01N 33/5767 435/7.92

FOREIGN PATENT DOCUMENTS

WO WO 8905658 A1 * 6/1989 ............. C07K 14/45
WO WO 9318150 A1 * 9/1993 ........... C07K 14/195

OTHER PUBLICATIONS

Merlini et al. (Seminars in Oncology, vol. 13, No. 3, Sep. 1986, pp. 350-365).*
Waldenstrom (Medical Oncology and Tumor Pharmacotherapy, vol. 3, No. 3/4 1986, pp. 135-140).*
International Search Report for PCT/EP2013/065524 dated Sep. 4, 2013.
Written Opinion of the International Searching Authority for PCT/EP2013/065524 dated Sep. 4, 2013.
J. Karlsson et al: "Comparative Study of Immune Status to Infectious Agents in Elderly Patients with Multiple Myeloma, Waldenstrom's Macroglobulinemia, and Monoclonal Gammopathy of Undetermined Significance", Clinical and Vaccine Immunology, vol. 18, No. 6, (Jun. 1, 2011), pp. 969-977.
Ardizzoni A et al: "A protein microarray immunoassay for the serological evaluation of the antibody response in vertically transmitted infections", European Journal of Clinical Microbiology 1-5,7 & Infectious Diseases, Springer, Berlin, DE, vol. 28, No. 9, (May 5, 2009), pp. 1067-1075.
Mezzasoma Letizia et al: "Antigen microarrays for serodiagnosis of infectious diseases.", Clinical Chemistry Jan. 2002, vol. 48, No. 1, (Jan. 2002), pp. 121-130.
Burbelo Peter D et al: "Highly quantitative serological detection of anti-cytomegalovirus (CMV) antibodies", Virology Journal, Biomed Central, London, GB, vol. 6, No. 1, (May 1, 2009), pp. 45-1-45-8.
L. M. Brown et al: "Risk of multiple myeloma and monoclonal gammopathy of undetermined significance among white and black male United States veterans with prior autoimmune, infectious, inflammatory, and allergic disorders", Blood, vol. 111, No. 7, (Apr. 1, 2008) pp. 3388-3394.
Delphine Feron et al: "Multiplexed infectious protein microarray immunoassay suitable for the study of the specificity of monoclonal immunoglobulins", Analytical Biochemistry, vol. 433, No. 2, (Feb. 1, 2013), pp. 202-209.

* cited by examiner

*Primary Examiner* — Karla A Dines
(74) *Attorney, Agent, or Firm* — B. Aaron Schulman, Esq.; Stites & Harbison, PLLC

(57) ABSTRACT

The present invention concerns materials and methods for characterizing monoclonal immunoglobulin specificity of a Monoclonal Gammopathy of Undetermined Significance (MGUS) or Myeloma patients using a protein microarray comprising (a) a substrate, (b) antigens immobilized on the substrate, said antigens being selected from a defined group consisting of infectious agent antigens and/or self-antigens. In particular said protein microarray may be used to improve diagnosis, for the prognosis of myeloma or MGUS, for preventing transformation of MGUS toward myeloma, for adapting treatment of MGUS and myeloma or for monitoring the response to therapy of MGUS and myeloma patients.

9 Claims, 9 Drawing Sheets

Figure 1:
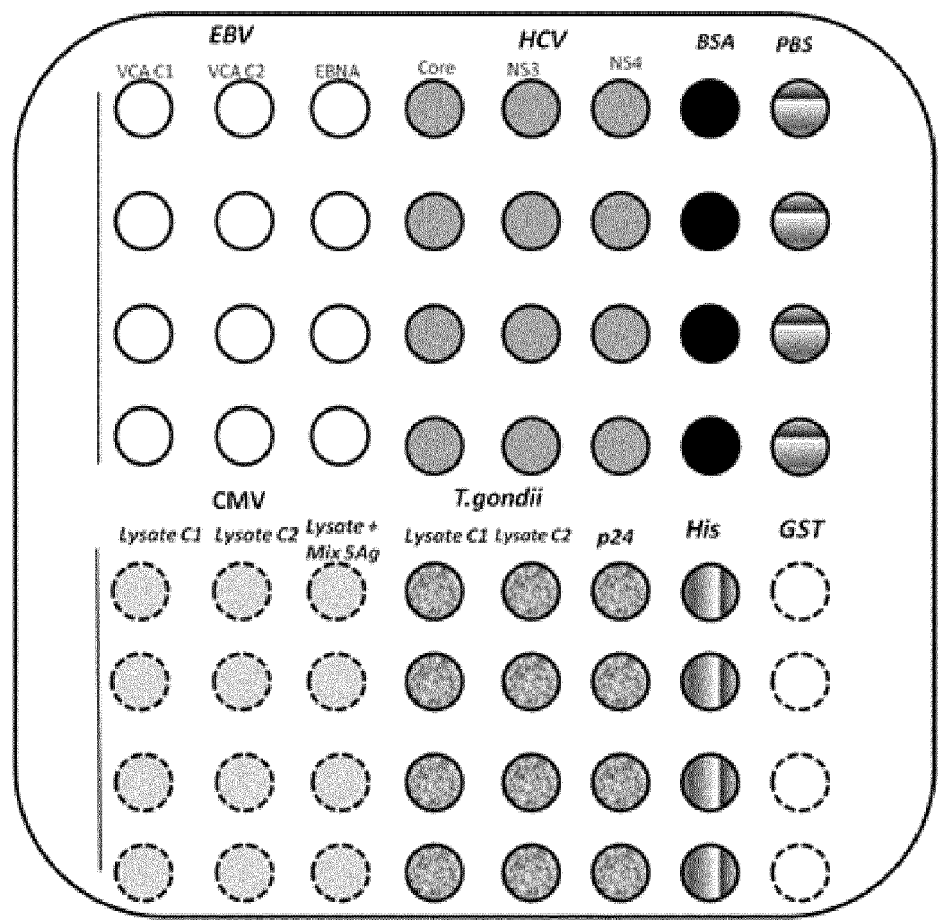

SEQUENCE LISTING

```
<160> NUMBER OF SEQ ID NOS: 66

<210> SEQ ID NO 1
<211> LENGTH: 207
<212> TYPE: PRT
<213> ORGANISM: Cytomegalovirus

<400> SEQUENCE: 1

Thr Ser His Glu His Phe Gly Leu Leu Cys Pro Lys Ser Ile Pro Gly
1               5                   10                  15

Leu Ser Ile Ser Gly Asn Leu Leu Met Asn Gly Gln Gln Ile Phe Leu
            20                  25                  30

Glu Val Gln Ala Ile Arg Glu Thr Val Glu Leu Arg Gln Tyr Asp Pro
        35                  40                  45

Val Ala Ala Leu Phe Phe Phe Asp Ile Asp Leu Leu Leu Gln Arg Gly
    50                  55                  60

Pro Gln Tyr Ser Glu His Pro Thr Phe Thr Ser Gln Tyr Arg Ile Gln
65                  70                  75                  80

Gly Lys Leu Glu Tyr Arg His Thr Trp Asp Arg His Asp Glu Gly Ala
            85                  90                  95

Ala Gln Gly Asp Asp Asp Val Trp Thr Ser Gly Ser Asp Ser Asp Glu
            100                 105                 110

Glu Leu Val Thr Thr Glu Arg Lys Thr Pro Arg Val Thr Gly Gly Gly
            115                 120                 125

Ala Met Ala Gly Ala Ser Thr Ser Ala Gly Arg Lys Arg Lys Ser Ala
    130                 135                 140

Ser Ser Ala Thr Ala Cys Thr Ser Gly Val Met Thr Arg Gly Arg Leu
145                 150                 155                 160

Lys Ala Glu Ser Thr Val Ala Pro Glu Glu Asp Thr Asp Glu Asp Ser
                165                 170                 175

Asp Asn Glu Ile His Asn Pro Ala Val Phe Thr Trp Pro Pro Trp Gln
            180                 185                 190

Ala Gly Ile Leu Ala Arg Asn Leu Val Pro Met Val Ala Thr Val
        195                 200                 205

<210> SEQ ID NO 2
<211> LENGTH: 190
<212> TYPE: PRT
<213> ORGANISM: Cytomegalovirus
```

```
<400> SEQUENCE: 2

Met Gly Ala Glu Leu Cys Lys Arg Ile Cys Cys Glu Phe Gly Thr Thr
1               5                   10                  15

Pro Gly Glu Pro Leu Lys Asp Ala Leu Gly Arg Gln Val Ser Leu Arg
            20                  25                  30

Ser Tyr Asp Asn Ile Pro Pro Thr Ser Ser Asp Glu Gly Glu Asp
        35                  40                  45

Asp Asp Asp Gly Glu Asp Asp Asn Glu Glu Arg Gln Gln Lys Leu
    50                  55                  60

Arg Leu Cys Gly Ser Gly Cys Gly Gly Asn Asp Ser Ser Ser Gly Ser
65                  70                  75                  80

His Arg Glu Ala Thr His Asp Gly Ser Lys Lys Asn Ala Val Arg Ser
                85                  90                  95

Thr Phe Arg Glu Asp Lys Ala Pro Lys Pro Ser Lys Ser Lys Lys
                100                 105                 110

Lys Lys Lys Pro Ser Lys His His His His Gln Gln Ser Ser Ile Met
            115                 120                 125

Gln Glu Thr Asp Asp Leu Asp Glu Glu Asp Thr Ser Ile Tyr Leu Ser
    130                 135                 140

Pro Pro Pro Val Pro Pro Val Gln Val Val Ala Lys Arg Leu Pro Arg
145                 150                 155                 160

Pro Asp Thr Pro Arg Thr Pro Arg Gln Lys Lys Ile Ser Gln Arg Pro
                165                 170                 175

Pro Thr Pro Gly Thr Lys Lys Pro Ala Ala Ser Leu Pro Phe
            180                 185                 190

<210> SEQ ID NO 3
<211> LENGTH: 433
<212> TYPE: PRT
<213> ORGANISM: Cytomegalovirus

<400> SEQUENCE: 3

Met Asp Arg Lys Thr Arg Leu Ser Glu Pro Pro Thr Leu Ala Leu Arg
1               5                   10                  15

Leu Lys Pro Tyr Lys Thr Ala Ile Gln Gln Leu Arg Ser Val Ile Arg
            20                  25                  30

Ala Leu Lys Glu Asn Thr Thr Val Thr Phe Leu Pro Thr Pro Ser Leu
        35                  40                  45

Ile Leu Gln Thr Val Arg Ser His Cys Val Ser Lys Ile Thr Phe Asn
    50                  55                  60

Ser Ser Cys Leu Tyr Ile Thr Asp Lys Ser Phe Gln Pro Lys Thr Ile
65                  70                  75                  80

Asn Asn Ser Thr Pro Leu Leu Gly Asn Phe Met Tyr Leu Thr Ser Ser
                85                  90                  95

Lys Asp Leu Thr Lys Phe Tyr Val Gln Asp Ile Ser Asp Leu Ser Ala
                100                 105                 110

Lys Ile Ser Met Cys Ala Pro Asp Phe Asn Met Glu Phe Ser Ser Ala
            115                 120                 125

Cys Val His Gly Gln Asp Ile Val Arg Glu Ser Glu Asn Ser Ala Val
        130                 135                 140

His Val Asp Leu Asp Phe Gly Val Val Ala Asp Leu Leu Lys Trp Ile
145                 150                 155                 160

Gly Pro His Thr Arg Val Lys Arg Asn Val Lys Lys Ala Pro Cys Pro
                165                 170                 175
```

```
Thr Gly Thr Val Gln Ile Leu Val His Ala Gly Pro Pro Ala Ile Lys
            180                 185                 190

Phe Ile Leu Thr Asn Gly Ser Glu Leu Glu Phe Thr Ala Asn Asn Arg
        195                 200                 205

Val Ser Phe His Gly Val Lys Asn Met Arg Ile Asn Val Gln Leu Lys
    210                 215                 220

Asn Phe Tyr Gln Thr Leu Leu Asn Cys Ala Val Thr Lys Leu Pro Cys
225                 230                 235                 240

Thr Leu Arg Ile Val Thr Glu His Asp Thr Leu Leu Tyr Val Ala Ser
                245                 250                 255

Arg Asn Gly Leu Phe Ala Val Glu Asn Phe Leu Thr Glu Glu Pro Phe
            260                 265                 270

Gln Arg Gly Asp Pro Phe Asp Lys Asn Tyr Val Gly Asn Ser Gly Lys
        275                 280                 285

Ser Arg Gly Gly Gly Gly Gly Gly Ser Leu Ser Ser Leu Ala Asn
    290                 295                 300

Ala Gly Gly Leu His Asp Asp Gly Pro Gly Leu Asp Asn Asp Leu Met
305                 310                 315                 320

Asn Glu Pro Met Gly Leu Gly Gly Leu Gly Gly Gly Gly Gly Gly
                325                 330                 335

Gly Lys Lys His Asp Arg Gly Gly Gly Gly Ser Gly Thr Arg Lys
            340                 345                 350

Met Ser Ser Gly Gly Gly Gly Asp His Asp His Gly Leu Ser Ser
        355                 360                 365

Lys Glu Lys Tyr Glu Gln His Lys Ile Thr Ser Tyr Leu Thr Ser Lys
    370                 375                 380

Gly Gly Ser Gly Gly Gly Gly Gly Gly Gly Gly Gly Leu Asp Arg
385                 390                 395                 400

Asn Ser Gly Asn Tyr Phe Asn Asp Ala Lys Glu Ser Asp Ser Glu
                405                 410                 415

Asp Ser Val Thr Phe Glu Phe Val Pro Asn Thr Lys Lys Gln Lys Cys
            420                 425                 430

Gly

<210> SEQ ID NO 4
<211> LENGTH: 906
<212> TYPE: PRT
<213> ORGANISM: Cytomegalovirus

<400> SEQUENCE: 4

Met Glu Ser Arg Ile Trp Cys Leu Val Val Cys Val Asn Leu Cys Ile
1               5                   10                  15

Val Cys Leu Gly Ala Ala Val Ser Ser Ser Thr Ser His Ala Thr
            20                  25                  30

Ser Ser Thr His Asn Gly Ser His Thr Ser Arg Thr Thr Ser Ala Gln
        35                  40                  45

Thr Arg Ser Val Tyr Ser Gln His Val Thr Ser Ser Glu Ala Val Ser
    50                  55                  60

His Arg Ala Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Ile Cys Thr
            100                 105                 110
```

```
Ser Met Lys Pro Ile Asn Glu Asp Leu Asp Glu Gly Ile Met Val Val
            115                 120                 125

Tyr Lys Arg Asn Ile Val Ala His Thr Phe Lys Val Arg Val Tyr Gln
        130                 135                 140

Lys Val Leu Thr Phe Arg Arg Ser Tyr Ala Tyr Ile Tyr Thr Thr Tyr
145                 150                 155                 160

Leu Leu Gly Ser Asn Thr Glu Tyr Val Ala Pro Pro Met Trp Glu Ile
                165                 170                 175

His His Ile Asn Lys Phe Ala Gln Cys Tyr Ser Ser Tyr Ser Arg Val
            180                 185                 190

Ile Gly Gly Thr Val Phe Val Ala Tyr His Arg Asp Ser Tyr Glu Asn
        195                 200                 205

Lys Thr Met Gln Leu Ile Pro Asp Asp Tyr Ser Asn Thr His Ser Thr
210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Leu Thr Ile Thr Thr
                245                 250                 255

Ala Arg Ser Lys Tyr Pro Tyr His Phe Phe Ala Thr Ser Thr Gly Asp
            260                 265                 270

Val Val Tyr Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
        290                 295                 300

Ile Val Ser Asp Phe Gly Arg Pro Asn Ala Ala Pro Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
        370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Ser Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Ile Thr His Arg Thr Arg Arg Ser Thr Ser Asp Asn
450                 455                 460

Asn Thr Thr His Leu Ser Ser Met Glu Ser Val His Asn Leu Val Tyr
465                 470                 475                 480

Ala Gln Leu Gln Phe Thr Tyr Asp Thr Leu Arg Gly Tyr Ile Asn Arg
                485                 490                 495

Ala Leu Ala Gln Ile Ala Glu Ala Trp Cys Val Asp Gln Arg Arg Thr
            500                 505                 510

Leu Glu Val Phe Lys Glu Leu Ser Lys Ile Asn Pro Ser Ala Ile Leu
        515                 520                 525

Ser Ala Ile Tyr Asn Lys Pro Ile Ala Ala Arg Phe Met Gly Asp Val
```

```
            530                 535                 540
Leu Gly Leu Ala Ser Cys Val Thr Ile Asn Gln Thr Ser Val Lys Val
545                 550                 555                 560

Leu Arg Asp Met Asn Val Lys Glu Ser Pro Gly Arg Cys Tyr Ser Arg
                565                 570                 575

Pro Val Val Ile Phe Asn Phe Ala Asn Ser Ser Tyr Val Gln Tyr Gly
            580                 585                 590

Gln Leu Gly Glu Asp Asn Glu Ile Leu Leu Gly Asn His Arg Thr Glu
        595                 600                 605

Glu Cys Gln Leu Pro Ser Leu Lys Ile Phe Ile Ala Gly Asn Ser Ala
    610                 615                 620

Tyr Glu Tyr Val Asp Tyr Leu Phe Lys Arg Met Ile Asp Leu Ser Ser
625                 630                 635                 640

Ile Ser Thr Val Asp Ser Met Ile Ala Leu Asp Ile Asp Pro Leu Glu
                645                 650                 655

Asn Thr Asp Phe Arg Val Leu Glu Leu Tyr Ser Gln Lys Glu Leu Arg
            660                 665                 670

Ser Ser Asn Val Phe Asp Leu Glu Glu Ile Met Arg Glu Phe Asn Ser
        675                 680                 685

Tyr Lys Gln Arg Val Lys Tyr Val Glu Asp Lys Val Val Asp Pro Leu
    690                 695                 700

Pro Pro Tyr Leu Lys Gly Leu Asp Asp Leu Met Ser Gly Leu Gly Ala
705                 710                 715                 720

Ala Gly Lys Ala Val Gly Val Ala Ile Gly Ala Val Gly Gly Ala Val
                725                 730                 735

Ala Ser Val Val Glu Gly Val Ala Thr Phe Leu Lys Asn Pro Phe Gly
            740                 745                 750

Ala Phe Thr Ile Ile Leu Val Ala Ile Ala Val Val Ile Ile Thr Tyr
        755                 760                 765

Leu Ile Tyr Thr Arg Gln Arg Arg Leu Cys Thr Gln Pro Leu Gln Asn
    770                 775                 780

Leu Phe Pro Tyr Leu Val Ser Ala Asp Gly Thr Thr Val Thr Ser Gly
785                 790                 795                 800

Ser Thr Lys Asp Thr Ser Leu Gln Ala Pro Pro Ser Tyr Glu Glu Ser
                805                 810                 815

Val Tyr Asn Ser Gly Arg Lys Gly Pro Gly Pro Pro Ser Ser Asp Ala
            820                 825                 830

Ser Thr Ala Ala Pro Pro Tyr Thr Asn Glu Gln Ala Tyr Gln Met Leu
        835                 840                 845

Leu Ala Leu Ala Arg Leu Asp Ala Glu Gln Arg Ala Gln Gln Asn Gly
    850                 855                 860

Thr Asp Ser Leu Asp Gly Gln Thr Gly Thr Gln Asp Lys Gly Gln Lys
865                 870                 875                 880

Pro Asn Leu Leu Asp Arg Leu Arg His Arg Lys Asn Gly Tyr Arg His
                885                 890                 895

Leu Lys Asp Ser Asp Glu Glu Glu Asn Val
            900                 905

<210> SEQ ID NO 5
<211> LENGTH: 707
<212> TYPE: PRT
<213> ORGANISM: Cytomegalovirus

<400> SEQUENCE: 5
```

```
Met Thr Met Asp Glu Gln Gln Pro Gln Ala Val Thr Pro Val Tyr Val
1               5                   10                  15

Gly Gly Phe Leu Ala Arg Tyr Asp Gln Ser Pro Asp Glu Ala Glu Leu
            20                  25                  30

Leu Leu Pro Arg Asp Val Val Glu His Trp Leu His Ala Gln Gly Gln
        35                  40                  45

Gly Gln Pro Ser Leu Ser Val Ala Leu Pro Leu Asn Ile Asn His Asp
50                  55                  60

Asp Thr Ala Val Val Gly His Val Ala Ala Met Gln Ser Val Arg Asp
65                  70                  75                  80

Gly Leu Phe Cys Leu Gly Cys Val Thr Ser Pro Arg Phe Leu Glu Ile
                85                  90                  95

Val Arg Arg Ala Ser Glu Lys Ser Glu Leu Val Ser Arg Gly Pro Val
            100                 105                 110

Ser Pro Leu Gln Pro Asp Lys Val Val Glu Phe Leu Ser Gly Ser Tyr
        115                 120                 125

Ala Gly Leu Ser Leu Ser Ser Arg Arg Cys Asp Asp Val Glu Ala Ala
    130                 135                 140

Thr Ser Leu Ser Gly Ser Glu Thr Thr Pro Phe Lys His Val Ala Leu
145                 150                 155                 160

Cys Ser Val Gly Arg Arg Gly Thr Leu Ala Val Tyr Gly Arg Asp
                165                 170                 175

Pro Glu Trp Val Thr Gln Arg Phe Pro Asp Leu Thr Ala Ala Asp Arg
            180                 185                 190

Asp Gly Leu Arg Ala Gln Trp Gln Arg Cys Gly Ser Thr Ala Val Asp
        195                 200                 205

Ala Ser Gly Asp Pro Phe Arg Ser Asp Ser Tyr Gly Leu Leu Gly Asn
    210                 215                 220

Ser Val Asp Ala Leu Tyr Ile Arg Glu Arg Leu Pro Lys Leu Arg Tyr
225                 230                 235                 240

Asp Lys Gln Leu Val Gly Val Thr Glu Arg Glu Ser Tyr Val Lys Ala
                245                 250                 255

Ser Val Ser Pro Glu Ala Ala Cys Asp Ile Lys Ala Ala Ser Ala Glu
            260                 265                 270

Arg Ser Gly Asp Ser Arg Ser Gln Ala Ala Thr Pro Ala Ala Gly Ala
        275                 280                 285

Arg Val Pro Ser Ser Ser Pro Ser Pro Val Glu Pro Pro Ser Pro
    290                 295                 300

Val Gln Pro Pro Ala Leu Pro Ala Ser Pro Ser Val Leu Pro Ala Glu
305                 310                 315                 320

Ser Ser Pro Ser Leu Ser Pro Ser Glu Pro Ala Glu Ala Ala Ser Met
                325                 330                 335

Ser His Pro Leu Ser Ala Ala Val Thr Ala Ala Thr Ala Pro Pro Gly
            340                 345                 350

Ala Thr Val Ala Gly Ala Ser Pro Ala Val Pro Ser Leu Ala Trp Pro
        355                 360                 365

His Asp Gly Val Tyr Leu Pro Lys Asp Ala Phe Phe Ser Leu Leu Gly
    370                 375                 380

Ala Ser Arg Ser Ala Ala Pro Val Met Tyr Pro Gly Ala Val Ala Ala
385                 390                 395                 400

Pro Pro Ser Ala Ser Pro Ala Pro Leu Pro Leu Pro Ser Tyr Pro Ala
                405                 410                 415

Ser Tyr Gly Ala Pro Val Val Gly Tyr Asp Gln Leu Ala Ala Arg His
```

```
                420                 425                 430
Phe Ala Asp Tyr Val Asp Pro His Tyr Pro Gly Trp Gly Arg Arg Tyr
            435                 440                 445
Glu Pro Ala Pro Ser Leu His Pro Ser Tyr Pro Val Pro Pro Pro Pro
        450                 455                 460
Ser Pro Ala Tyr Tyr Arg Arg Asp Ser Pro Gly Gly Met Asp Glu
465                 470                 475                 480
Pro Pro Ser Gly Trp Glu Arg Tyr Asp Gly Ser His Arg Gly Gln Ser
                485                 490                 495
Gln Lys Gln His Arg His Gly Ser Gly Gly His Asn Lys Arg Arg
            500                 505                 510
Lys Glu Ala Ala Ala Ser Ser Ser Asp Glu Asp Leu Ser Phe
        515                 520                 525
Pro Gly Glu Ala Glu His Gly Arg Ala Arg Lys Arg Leu Lys Ser His
        530                 535                 540
Val Asn Ser Asp Gly Gly Ser Gly Gly His Ala Gly Ser Asn Gln Gln
545                 550                 555                 560
Gln Gln Gln Arg Tyr Asp Glu Leu Arg Asp Ala Ile His Glu Leu Lys
                565                 570                 575
Arg Asp Leu Phe Ala Ala Arg Gln Ser Ser Thr Leu Leu Ser Ala Ala
            580                 585                 590
Leu Pro Ala Ala Ala Ser Ser Ser Pro Thr Thr Thr Thr Val Cys Thr
        595                 600                 605
Pro Thr Gly Glu Leu Thr Ser Gly Gly Gly Glu Thr Pro Thr Ala Leu
        610                 615                 620
Leu Ser Gly Gly Ala Lys Val Ala Glu Arg Ala Gln Ala Gly Val Val
625                 630                 635                 640
Asn Ala Ser Cys Arg Leu Ala Thr Ala Ser Gly Ser Glu Ala Ala Thr
                645                 650                 655
Ala Gly Pro Ser Thr Ala Gly Ser Ser Ser Cys Pro Ala Ser Val Val
            660                 665                 670
Leu Ala Ala Ala Ala Gln Ala Ala Ala Ser Gln Ser Pro Pro
        675                 680                 685
Lys Asp Met Val Asp Leu Asn Arg Arg Ile Phe Val Ala Ala Leu Asn
        690                 695                 700
Lys Leu Glu
705

<210> SEQ ID NO 6
<211> LENGTH: 190
<212> TYPE: PRT
<213> ORGANISM: Toxoplasma gondii

<400> SEQUENCE: 6

Met Val Arg Val Ser Ala Ile Val Gly Ala Ala Ser Val Phe Val
1               5                   10                  15

Cys Leu Ser Ala Gly Ala Tyr Ala Ala Glu Gly Gly Asp Asn Gln Ser
            20                  25                  30

Ser Ala Val Ser Asp Arg Ala Ser Leu Phe Gly Leu Leu Ser Gly Gly
        35                  40                  45

Thr Gly Gln Gly Leu Gly Ile Gly Glu Ser Val Asp Leu Glu Met Met
    50                  55                  60

Gly Asn Thr Tyr Arg Val Glu Arg Pro Thr Gly Asn Pro Asp Leu Leu
65              70                  75                  80
```

```
Lys Ile Ala Ile Lys Ala Ser Asp Gly Ser Tyr Ser Glu Val Gly Asn
                85                  90                  95

Val Asn Val Glu Glu Val Ile Asp Thr Met Lys Ser Met Gln Arg Asp
            100                 105                 110

Glu Asp Ile Phe Leu Arg Ala Leu Asn Lys Gly Glu Thr Val Glu Glu
        115                 120                 125

Ala Ile Glu Asp Val Ala Gln Ala Glu Gly Leu Asn Ser Glu Gln Thr
    130                 135                 140

Leu Gln Leu Glu Asp Ala Val Ser Ala Val Ala Ser Val Val Gln Asp
145                 150                 155                 160

Glu Met Lys Val Ile Asp Asp Val Gln Gln Leu Glu Lys Asp Lys Gln
                165                 170                 175

Gln Leu Lys Asp Asp Ile Gly Phe Leu Thr Gly Glu Arg Glu
            180                 185                 190

<210> SEQ ID NO 7
<211> LENGTH: 120
<212> TYPE: PRT
<213> ORGANISM: Hepatitis C virus

<400> SEQUENCE: 7

Asn Pro Lys Pro Gln Arg Lys Thr Lys Arg Asn Thr Asn Arg Arg Pro
1               5                   10                  15

Gln Asp Ala Lys Phe Pro Gly Gly Gly Gln Ile Val Gly Gly Val Tyr
            20                  25                  30

Leu Leu Pro Arg Arg Gly Pro Arg Leu Gly Val Arg Ala Thr Arg Lys
        35                  40                  45

Thr Ser Glu Arg Ser Gln Pro Arg Gly Arg Arg Gln Pro Ile Pro Lys
    50                  55                  60

Ala Cys Arg Pro Glu Gly Arg Ala Trp Ala Gln Pro Gly Tyr Pro Trp
65                  70                  75                  80

Pro Leu Tyr Gly Asn Glu Gly Leu Gly Trp Ala Gly Trp Leu Leu Ser
                85                  90                  95

Pro Arg Gly Ser Arg Pro Ser Trp Gly Pro Thr Asp Pro Arg Arg Arg
            100                 105                 110

Ser Arg Asn Leu Gly Lys Val Ile
        115                 120

<210> SEQ ID NO 8
<211> LENGTH: 119
<212> TYPE: PRT
<213> ORGANISM: Hepatitis C virus

<400> SEQUENCE: 8

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95
```

```
Leu Leu Ser Pro Arg Gly Ser Arg Pro Ser Trp Gly Pro Thr Asp Pro
            100                 105                 110

Arg Arg Arg Ser Arg Asn Leu
        115

<210> SEQ ID NO 9
<211> LENGTH: 119
<212> TYPE: PRT
<213> ORGANISM: Hepatitis C virus

<400> SEQUENCE: 9

Leu Pro Lys Pro Gln Arg Gln Thr Lys Arg Asn Thr Pro Arg Arg Pro
1               5                   10                  15

Gln Asn Val Lys Phe Pro Gly Gly Gln Ile Val Gly Gly Val Tyr
            20                  25                  30

Val Leu Pro Arg Arg Gly Pro Arg Leu Gly Val Arg Ala Val Arg Lys
            35                  40                  45

Thr Ser Glu Arg Ser Glu Pro Arg Ala Arg Gln Pro Ile Pro Lys
    50                  55                  60

Ala Arg Pro Gly Glu Gly Arg Ser Trp Ala Gln Pro Gly Tyr Pro Trp
65                  70                  75                  80

Pro Leu Tyr Gly Asn Glu Gly Cys Gly Trp Ala Gly Trp Leu Leu Ser
                85                  90                  95

Pro Arg Gly Ser Arg Pro Ser Trp Gly Pro Asn Asp Pro Arg Arg Arg
            100                 105                 110

Ser Arg Asn Leu Gly Lys Val
        115

<210> SEQ ID NO 10
<211> LENGTH: 120
<212> TYPE: PRT
<213> ORGANISM: Hepatitis C virus

<400> SEQUENCE: 10

Leu Pro Lys Pro Gln Arg Gln Thr Lys Arg Asn Thr Pro Arg Arg Pro
1               5                   10                  15

Gln Asn Val Lys Phe Pro Gly Gly Gln Ile Val Gly Gly Val Tyr
            20                  25                  30

Val Leu Pro Arg Arg Gly Pro Arg Leu Gly Val Arg Ala Val Arg Lys
            35                  40                  45

Thr Ser Glu Arg Ser Gln Pro Arg Gly Arg Arg His Arg Ile Pro Lys
    50                  55                  60

Ala Arg Gln Arg Glu Gly Arg Ser Trp Ala Gln Pro Gly Tyr Pro Trp
65                  70                  75                  80

Pro Leu Tyr Gly Asn Glu Gly Cys Gly Trp Ala Gly Trp Leu Leu Ser
                85                  90                  95

Pro Arg Gly Ser Arg Pro Ser Trp Gly Pro Asn Asp Pro Arg Arg Arg
            100                 105                 110

Ser Arg Asn Leu Gly Lys Val Ile
        115                 120

<210> SEQ ID NO 11
<211> LENGTH: 420
<212> TYPE: PRT
<213> ORGANISM: Hepatitis C virus

<400> SEQUENCE: 11

Val Phe Thr Asp Asn Ser Ser Pro Pro Ala Val Pro Gln Ser Phe Gln
```

-continued

```
1               5                   10                  15
Val Ala His Leu His Ala Pro Thr Gly Ser Gly Lys Ser Thr Lys Val
            20                  25                  30

Pro Ala Ala Tyr Ala Ala Gln Gly Tyr Lys Val Leu Val Leu Asn Pro
            35                  40                  45

Ser Val Ala Ala Thr Leu Gly Phe Gly Ala Tyr Met Ser Lys Ala His
 50                      55                  60

Gly Val Asp Pro Asn Ile Arg Thr Gly Val Arg Thr Ile Thr Thr Gly
 65                  70                  75                  80

Ser Pro Ile Thr Tyr Ser Thr Tyr Gly Lys Phe Leu Ala Asp Gly Gly
                     85                  90                  95

Cys Ser Gly Gly Ala Tyr Asp Ile Ile Ile Cys Asp Glu Cys His Ser
                100                 105                 110

Thr Asp Ala Thr Ser Ile Leu Gly Ile Gly Thr Val Leu Asp Gln Ala
                115                 120                 125

Glu Thr Ala Gly Ala Arg Leu Val Val Leu Ala Thr Ala Thr Pro Pro
130                 135                 140

Gly Ser Val Thr Val Ser His Pro Asn Ile Glu Glu Val Ala Leu Ser
145                 150                 155                 160

Thr Thr Gly Glu Ile Pro Phe Tyr Gly Lys Ala Ile Pro Leu Glu Val
                    165                 170                 175

Ile Lys Gly Gly Arg His Leu Ile Phe Cys His Ser Lys Lys Lys Cys
                180                 185                 190

Asp Glu Leu Ala Ala Lys Leu Val Ala Leu Gly Ile Asn Ala Val Ala
                195                 200                 205

Tyr Tyr Arg Gly Leu Asp Val Ser Val Ile Pro Thr Ser Gly Asp Val
210                 215                 220

Val Val Val Ser Thr Asp Ala Leu Met Thr Gly Phe Thr Gly Asp Phe
225                 230                 235                 240

Asp Ser Val Ile Asp Cys Asn Thr Cys Val Thr Gln Thr Val Asp Phe
                    245                 250                 255

Ser Leu Asp Pro Thr Phe Thr Ile Glu Thr Thr Thr Leu Pro Gln Asp
                260                 265                 270

Ala Val Ser Arg Thr Gln Arg Arg Gly Arg Thr Gly Arg Gly Lys Pro
                275                 280                 285

Gly Ile Tyr Arg Phe Val Ala Pro Gly Glu Arg Pro Ser Gly Met Phe
                290                 295                 300

Asp Ser Ser Val Leu Cys Glu Cys Tyr Asp Ala Gly Cys Ala Trp Tyr
305                 310                 315                 320

Glu Leu Thr Pro Ala Glu Thr Thr Val Arg Leu Arg Ala Tyr Met Asn
                    325                 330                 335

Thr Pro Gly Leu Pro Val Cys Gln Asp His Leu Glu Phe Trp Glu Gly
                340                 345                 350

Val Phe Thr Gly Leu Thr His Ile Asp Ala His Phe Leu Ser Gln Thr
                355                 360                 365

Lys Gln Ser Gly Glu Asn Phe Pro Tyr Leu Val Ala Tyr Gln Ala Thr
                370                 375                 380

Val Cys Ala Arg Ala Gln Ala Pro Pro Ser Trp Asp Gln Met Trp
385                 390                 395                 400

Lys Cys Leu Ile Arg Leu Lys Pro Thr Leu His Gly Pro Thr Pro Leu
                    405                 410                 415

Leu Tyr Arg Leu
            420
```

<210> SEQ ID NO 12
<211> LENGTH: 639
<212> TYPE: PRT
<213> ORGANISM: Hepatitis C virus

<400> SEQUENCE: 12

```
Ala Pro Ile Thr Ala Tyr Ala Gln Gln Thr Arg Gly Leu Leu Gly Cys
1               5                   10                  15

Ile Ile Thr Ser Leu Thr Gly Arg Asp Lys Asn Gln Val Glu Gly Glu
            20                  25                  30

Val Gln Ile Val Ser Thr Ala Ala Gln Thr Phe Leu Ala Thr Cys Ile
        35                  40                  45

Asn Gly Val Cys Trp Thr Val Tyr His Gly Ala Gly Thr Arg Thr Ile
50                  55                  60

Ala Ser Ser Lys Gly Pro Val Ile Gln Met Tyr Thr Asn Val Asp Gln
65                  70                  75                  80

Asp Leu Val Gly Trp Pro Ala Pro Gln Gly Ala Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Gly Arg Gly Ser Leu Leu Ser
        115                 120                 125

Pro Arg Pro Ile Ser Tyr Leu Lys Gly Ser Ser Gly Gly Pro Leu Leu
130                 135                 140

Cys Pro Ala Gly His Ala Val Gly Ile Phe Arg Ala Ala Val Cys Thr
145                 150                 155                 160

Arg Gly Val Ala Lys Ala Val Asp Phe Ile Pro Val Glu Gly Leu Glu
                165                 170                 175

Thr Thr Met Arg Ser Pro Val Phe Ser Asp Asn Ser Ser Pro Pro Ala
            180                 185                 190

Val Pro Gln Ser Tyr Gln Val Ala His Leu His Ala Pro Thr Gly Ser
        195                 200                 205

Gly Lys Ser Thr Lys Val Pro Ala Ala Tyr Ala Ala Gln Gly Tyr Lys
210                 215                 220

Val Leu Val Leu Asn Pro Ser Val Ala Ala Thr Leu Gly Phe Gly Ala
225                 230                 235                 240

Tyr Met Ser Lys Ala His Gly Ile Asp Pro Asn Ile Arg Thr Gly Val
                245                 250                 255

Arg Thr Ile Thr Thr Gly Ser Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ala Thr Ser Ile Leu Gly Ile Gly
290                 295                 300

Thr Val Leu Asp Gln Ala Glu Thr Ala Gly Ala Arg Leu Thr Val Leu
305                 310                 315                 320

Ala Thr Ala Thr Pro Pro Gly Ser Val Thr Val Pro His Pro Asn Ile
                325                 330                 335

Glu Glu Val Ala Leu Ser Thr Thr Gly Glu Ile Pro Phe Tyr Gly Lys
            340                 345                 350

Ala Ile Pro Leu Glu Ala Ile Lys Gly Gly Arg His Leu Ile Phe Cys
        355                 360                 365

His Ser Lys Lys Lys Cys Asp Glu Leu Ala Ala Lys Leu Val Ala Leu
```

Gly Val Asn Ala Val Ala Tyr Tyr Arg Gly Leu Asp Val Ser Val Ile
385                 390                 395                 400

Pro Ala Ser Gly Asp Val Val Val Ala Thr Asp Ala Leu Met Thr
            405                 410                 415

Gly Phe Thr Gly Asp Phe Asp Ser Val Ile Asp Cys Asn Thr Cys Val
                420                 425                 430

Thr Gln Thr Val Asp Phe Ser Leu Asp Pro Thr Phe Thr Ile Glu Thr
            435                 440                 445

Thr Thr Leu Pro Gln Asp Ala Val Ser Arg Thr Gln Arg Arg Gly Arg
    450                 455                 460

Thr Gly Arg Gly Lys Pro Gly Ile Tyr Arg Phe Val Thr Pro Gly Glu
465                 470                 475                 480

Arg Pro Ser Gly Met Phe Asp Ser Ser Val Leu Cys Glu Cys Tyr Asp
                485                 490                 495

Ala Gly Cys Ala Trp Tyr Glu Leu Thr Pro Ala Glu Thr Thr Val Arg
            500                 505                 510

Leu Arg Ala Tyr Met Asn Thr Pro Gly Leu Pro Val Cys Gln Asp His
    515                 520                 525

Leu Glu Phe Trp Glu Gly Val Phe Thr Gly Leu Thr His Ile Asp Ala
530                 535                 540

His Phe Leu Ser Gln Thr Lys Gln Ser Gly Glu Asn Leu Pro Tyr Leu
545                 550                 555                 560

Val Ala Tyr Gln Ala Thr Val Cys Ala Arg Ala Gln Ala Pro Pro Pro
                565                 570                 575

Ser Trp Asp Gln Met Trp Lys Cys Leu Ile Arg Leu Lys Pro Thr Leu
            580                 585                 590

His Gly Pro Thr Pro Leu Leu Tyr Arg Leu Gly Ala Val Gln Asn Glu
    595                 600                 605

Ile Thr Leu Thr His Pro Ile Thr Lys Tyr Ile Met Thr Cys Met Ser
610                 615                 620

Ala Asp Leu Glu Val Val Thr Gly Ala Val Gln Asn Glu Val Thr
625                 630                 635

<210> SEQ ID NO 13
<211> LENGTH: 209
<212> TYPE: PRT
<213> ORGANISM: Hepatitis C virus

<400> SEQUENCE: 13

Asp Phe Trp Glu Ser Val Phe Thr Gly Leu Thr His Ile Asp Ala His
1               5                   10                  15

Phe Leu Ser Gln Thr Lys Gln Gln Gly Leu Asn Phe Ser Phe Leu Thr
            20                  25                  30

Ala Tyr Gln Ala Thr Val Cys Ala Arg Ala Gln Ala Pro Pro Pro Ser
        35                  40                  45

Trp Asp Glu Met Trp Lys Cys Leu Val Arg Leu Lys Pro Thr Leu His
    50                  55                  60

Gly Pro Thr Pro Leu Leu Tyr Arg Leu Gly Pro Val Gln Asn Glu Ile
65                  70                  75                  80

Cys Leu Thr His Pro Ile Thr Lys Tyr Ile Met Ala Cys Met Ser Ala
                85                  90                  95

Asp Leu Glu Val Thr Thr Ser Thr Trp Val Leu Leu Gly Gly Val Leu
            100                 105                 110

-continued

Ala Ala Leu Ala Ala Tyr Cys Leu Ser Val Gly Cys Val Ile Val
            115                 120                 125

Gly His Ile Glu Leu Gly Gly Lys Pro Ala Ile Val Pro Asp Lys Glu
130                 135                 140

Val Leu Tyr Gln Gln Tyr Asp Glu Met Glu Glu Cys Ser Gln Ala Ala
145                 150                 155                 160

Pro Tyr Ile Glu Gln Ala Gln Val Ile Ala His Gln Phe Lys Glu Lys
            165                 170                 175

Val Leu Gly Leu Leu Gln Arg Ala Thr Gln Gln Ala Val Ile Glu
            180                 185                 190

Pro Ile Val Thr Thr Asn Trp Gln Lys Leu Glu Ala Phe Trp His Lys
            195                 200                 205

His

<210> SEQ ID NO 14
<211> LENGTH: 176
<212> TYPE: PRT
<213> ORGANISM: Epstein Barr virus

<400> SEQUENCE: 14

Met Ala Arg Arg Leu Pro Lys Pro Thr Leu Gln Gly Arg Leu Glu Ala
1               5                   10                  15

Asp Phe Pro Asp Ser Pro Leu Leu Pro Lys Phe Gln Glu Leu Asn Gln
            20                  25                  30

Asn Asn Leu Pro Asn Asp Val Phe Arg Glu Ala Gln Arg Ser Tyr Leu
        35                  40                  45

Val Phe Leu Thr Ser Gln Phe Cys Tyr Glu Glu Tyr Val Gln Arg Thr
50                  55                  60

Phe Gly Val Pro Arg Arg Gln Arg Ala Ile Asp Lys Arg Gln Arg Ala
65                  70                  75                  80

Ser Val Ala Gly Ala Gly Ala His Ala His Leu Gly Gly Ser Ser Ala
                85                  90                  95

Thr Pro Val Gln Gln Ala Gln Ala Ala Ser Ala Gly Thr Gly Ala
            100                 105                 110

Leu Ala Ser Ser Ala Pro Ser Thr Ala Val Ala Gln Ser Ala Thr Pro
        115                 120                 125

Ser Val Ser Ser Ser Ile Ser Ser Leu Arg Ala Ala Thr Ser Gly Ala
130                 135                 140

Thr Ala Ala Ala Ser Ala Ala Ala Val Asp Thr Gly Ser Gly Gly
145                 150                 155                 160

Gly Gly Gln Pro His Asp Thr Ala Pro Arg Gly Ala Arg Lys Lys Gln
                165                 170                 175

<210> SEQ ID NO 15
<211> LENGTH: 1380
<212> TYPE: PRT
<213> ORGANISM: Epstein Barr virus

<400> SEQUENCE: 15

Met Ala Ser Asn Glu Gly Val Glu Asn Arg Pro Phe Pro Tyr Leu Thr
1               5                   10                  15

Val Asp Ala Asp Leu Leu Ser Asn Leu Arg Gln Ser Ala Ala Glu Gly
            20                  25                  30

Leu Phe His Ser Phe Asp Leu Leu Val Gly Lys Asp Ala Arg Glu Ala
        35                  40                  45

Gly Ile Lys Phe Glu Val Leu Leu Gly Val Tyr Thr Asn Ala Ile Gln

```
                50                  55                  60
Tyr Val Arg Phe Leu Glu Thr Ala Leu Ala Val Ser Cys Val Asn Thr
 65                  70                  75                  80

Glu Phe Lys Asp Leu Ser Arg Met Thr Asp Gly Lys Ile Gln Phe Arg
                 85                  90                  95

Ile Ser Val Pro Thr Ile Ala His Gly Asp Gly Arg Arg Pro Ser Lys
                100                 105                 110

Gln Arg Thr Phe Ile Val Val Lys Asn Cys His Lys His His Ile Ser
                115                 120                 125

Thr Glu Met Glu Leu Ser Met Leu Asp Leu Glu Ile Leu His Ser Ile
            130                 135                 140

Pro Glu Thr Pro Val Glu Tyr Ala Glu Tyr Val Gly Ala Val Lys Thr
145                 150                 155                 160

Val Ala Ser Ala Leu Gln Phe Gly Val Asp Ala Leu Glu Arg Gly Leu
                165                 170                 175

Ile Asn Thr Val Leu Ser Val Lys Leu Arg His Ala Pro Pro Met Phe
                180                 185                 190

Ile Leu Gln Thr Leu Ala Asp Pro Thr Phe Thr Glu Arg Gly Phe Ser
                195                 200                 205

Lys Thr Val Lys Ser Asp Leu Ile Ala Met Phe Lys Arg His Leu Leu
210                 215                 220

Glu His Ser Phe Phe Leu Asp Arg Ala Glu Asn Met Gly Ser Gly Phe
225                 230                 235                 240

Ser Gln Tyr Val Arg Ser Arg Leu Ser Glu Met Val Ala Ala Val Ser
                245                 250                 255

Gly Glu Ser Val Leu Lys Gly Val Ser Thr Tyr Thr Thr Ala Lys Gly
                260                 265                 270

Gly Glu Pro Val Gly Gly Val Phe Ile Val Thr Asp Asn Val Leu Arg
                275                 280                 285

Gln Leu Leu Thr Phe Leu Gly Glu Ala Asp Asn Gln Ile Met Gly
            290                 295                 300

Pro Ser Ser Tyr Ala Ser Phe Val Val Arg Gly Glu Asn Leu Val Thr
305                 310                 315                 320

Ala Val Ser Tyr Gly Arg Val Met Arg Thr Phe Glu His Phe Met Ala
                325                 330                 335

Arg Ile Val Asp Ser Pro Glu Lys Ala Gly Ser Thr Lys Ser Asp Leu
                340                 345                 350

Pro Ala Val Ala Ala Gly Val Glu Asp Gln Pro Arg Val Pro Ile Ser
                355                 360                 365

Ala Ala Val Ile Lys Leu Gly Asn His Ala Val Ala Val Glu Ser Leu
                370                 375                 380

Gln Lys Met Tyr Asn Asp Thr Gln Ser Pro Tyr Pro Leu Asn Arg Arg
385                 390                 395                 400

Met Gln Tyr Ser Tyr Tyr Phe Pro Val Gly Leu Phe Met Pro Asn Pro
                405                 410                 415

Lys Tyr Thr Thr Ser Ala Ala Ile Lys Met Leu Asp Asn Pro Thr Gln
                420                 425                 430

Gln Leu Pro Val Glu Ala Trp Ile Val Asn Lys Asn Leu Leu Leu
            435                 440                 445

Ala Phe Asn Leu Gln Asn Ala Leu Lys Val Leu Cys His Pro Arg Leu
                450                 455                 460

His Thr Pro Ala His Thr Leu Asn Ser Leu Asn Ala Ala Pro Ala Pro
465                 470                 475                 480
```

```
Arg Asp Arg Arg Glu Thr Tyr Ser Leu Gln His Arg Arg Pro Asn His
            485                 490                 495

Met Asn Val Leu Val Ile Val Asp Glu Phe Tyr Asp Asn Lys Tyr Ala
            500                 505                 510

Ala Pro Val Thr Asp Ile Ala Leu Lys Cys Gly Leu Pro Thr Glu Asp
            515                 520                 525

Phe Leu His Pro Ser Asn Tyr Asp Leu Leu Arg Leu Glu Leu His Pro
            530                 535                 540

Leu Tyr Asp Ile Tyr Ile Gly Arg Asp Ala Gly Glu Arg Ala Arg His
545                 550                 555                 560

Arg Ala Val His Arg Leu Met Val Gly Asn Leu Pro Thr Pro Leu Ala
                565                 570                 575

Pro Ala Ala Phe Gln Glu Ala Arg Gly Gln Gln Phe Glu Thr Ala Thr
            580                 585                 590

Ser Leu Ala His Val Val Asp Gln Ala Val Ile Glu Thr Val Gln Asp
            595                 600                 605

Thr Ala Tyr Asp Thr Ala Tyr Pro Ala Phe Phe Tyr Val Val Glu Ala
            610                 615                 620

Met Ile His Gly Phe Glu Glu Lys Phe Val Met Asn Val Pro Leu Val
625                 630                 635                 640

Ser Leu Cys Ile Asn Thr Tyr Trp Glu Arg Ala Gly Arg Leu Ala Phe
                645                 650                 655

Val Asn Ser Phe Ser Met Ile Lys Phe Ile Cys Arg His Leu Gly Asn
            660                 665                 670

Asn Ala Ile Ser Lys Glu Ala Tyr Ser Met Tyr Arg Lys Ile Tyr Gly
            675                 680                 685

Glu Leu Ile Ala Leu Glu Gln Ala Leu Met Arg Leu Ala Gly Ser Asp
            690                 695                 700

Val Val Gly Asp Glu Ser Val Gly Gln Tyr Val Cys Ala Leu Leu Asp
705                 710                 715                 720

Pro Asn Leu Leu Pro Pro Val Ala Tyr Thr Asp Ile Phe Thr His Leu
                725                 730                 735

Leu Thr Val Ser Asp Arg Ala Pro Gln Ile Ile Gly Asn Glu Val
            740                 745                 750

Tyr Ala Asp Thr Leu Ala Ala Pro Gln Phe Ile Glu Arg Val Gly Asn
            755                 760                 765

Met Asp Glu Met Ala Ala Gln Phe Val Ala Leu Tyr Gly Tyr Arg Val
770                 775                 780

Asn Gly Asp His Asp His Asp Phe Arg Leu His Leu Gly Pro Tyr Val
785                 790                 795                 800

Asp Glu Gly His Ala Asp Val Leu Glu Lys Ile Phe Tyr Tyr Val Phe
            805                 810                 815

Leu Pro Thr Cys Thr Asn Ala His Met Cys Gly Leu Gly Val Asp Phe
            820                 825                 830

Gln His Val Ala Gln Thr Leu Ala Tyr Asn Gly Pro Ala Phe Ser His
            835                 840                 845

His Phe Thr Arg Asp Glu Asp Ile Leu Asp Asn Leu Glu Asn Gly Thr
850                 855                 860

Leu Arg Asp Leu Leu Glu Ile Ser Asp Leu Arg Pro Thr Val Gly Met
865                 870                 875                 880

Ile Arg Asp Leu Ser Ala Ser Phe Met Thr Cys Pro Thr Phe Thr Arg
                885                 890                 895
```

```
Thr Val Arg Val Ser Val Asp Asn Asp Val Thr Gln Gln Leu Ala Pro
            900                 905                 910

Asn Pro Ala Asp Lys Arg Thr Glu Gln Thr Val Leu Val Asn Gly Leu
        915                 920                 925

Val Ala Phe Ala Phe Ser Glu Arg Thr Arg Ala Val Thr Gln Cys Leu
    930                 935                 940

Phe His Ala Ile Pro Phe His Met Phe Tyr Gly Asp Pro Arg Val Ala
945                 950                 955                 960

Ala Thr Met His Gln Asp Val Ala Thr Phe Val Met Arg Asn Pro Gln
                965                 970                 975

Gln Arg Ala Val Glu Ala Phe Asn Arg Pro Glu Gln Leu Phe Ala Glu
            980                 985                 990

Tyr Arg Glu Trp His Arg Ser Pro Met Gly Lys Tyr Ala Ala Glu Cys
        995                 1000                1005

Leu Pro Ser Leu Val Ser Ile Ser Gly Met Thr Ala Met His Ile
    1010            1015                1020

Lys Met Ser Pro Met Ala Tyr Ile Ala Gln Ala Lys Leu Lys Ile
    1025            1030                1035

His Pro Gly Val Ala Met Thr Val Val Arg Thr Asp Glu Ile Leu
    1040            1045                1050

Ser Glu Asn Ile Leu Phe Ser Ser Arg Ala Ser Thr Ser Met Phe
    1055            1060                1065

Ile Gly Thr Pro Asn Val Ser Arg Arg Glu Ala Arg Val Asp Ala
    1070            1075                1080

Val Thr Phe Glu Val His His Glu Met Ala Ser Ile Asp Thr Gly
    1085            1090                1095

Leu Ser Tyr Ser Ser Thr Met Thr Pro Ala Arg Val Ala Ala Ile
    1100            1105                1110

Thr Thr Asp Met Gly Ile His Thr Gln Asp Phe Phe Ser Val Phe
    1115            1120                1125

Pro Ala Glu Ala Phe Gly Asn Gln Gln Val Asn Asp Tyr Ile Lys
    1130            1135                1140

Ala Lys Val Gly Ala Gln Arg Asn Gly Thr Leu Leu Arg Asp Pro
    1145            1150                1155

Arg Thr Tyr Leu Ala Gly Met Thr Asn Val Asn Gly Ala Pro Gly
    1160            1165                1170

Leu Cys His Gly Gln Gln Ala Thr Cys Glu Ile Ile Val Thr Pro
    1175            1180                1185

Val Thr Ala Asp Val Ala Tyr Phe Gln Lys Ser Asn Ser Pro Arg
    1190            1195                1200

Gly Arg Ala Ala Cys Val Val Ser Cys Glu Asn Tyr Asn Gln Glu
    1205            1210                1215

Val Ala Glu Gly Leu Ile Tyr Asp His Ser Arg Pro Asp Ala Ala
    1220            1225                1230

Tyr Glu Tyr Arg Ser Thr Val Asn Pro Trp Ala Ser Gln Leu Gly
    1235            1240                1245

Ser Leu Gly Asp Ile Met Tyr Asn Ser Ser Tyr Arg Gln Thr Ala
    1250            1255                1260

Val Pro Gly Leu Tyr Ser Pro Cys Arg Ala Phe Phe Asn Lys Glu
    1265            1270                1275

Glu Leu Leu Arg Asn Asn Arg Gly Leu Tyr Asn Met Val Asn Glu
    1280            1285                1290

Tyr Ser Gln Arg Leu Gly Gly His Pro Ala Thr Ser Asn Thr Glu
```

```
                  1295                1300                1305

Val Gln Phe Val Val Ile Ala Gly Thr Asp Val Phe Leu Glu Gln
            1310                1315                1320

Pro Cys Ser Phe Leu Gln Glu Ala Phe Pro Ala Leu Ser Ala Ser
        1325                1330                1335

Ser Arg Ala Leu Ile Asp Glu Phe Met Ser Val Lys Gln Thr His
    1340                1345                1350

Ala Pro Ile His Tyr Gly His Tyr Ile Ile Glu Glu Val Ala Pro
1355                1360                1365

Val Arg Arg Ile Leu Lys Phe Gly Asn Lys Val Val
        1370                1375                1380

<210> SEQ ID NO 16
<211> LENGTH: 641
<212> TYPE: PRT
<213> ORGANISM: Epstein Barr virus

<400> SEQUENCE: 16

Met Ser Asp Glu Gly Pro Gly Thr Gly Pro Gly Asn Gly Leu Gly
1               5                   10                  15

Lys Gly Asp Thr Ser Gly Pro Glu Gly Ser Gly Ser Gly Pro Gln
            20                  25                  30

Arg Arg Gly Gly Asp Asn His Gly Arg Gly Arg Gly Arg Gly Arg
        35                  40                  45

Gly Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile
65                  70                  75                  80

Gly Cys Lys Gly Thr His Gly Gly Thr Gly Ala Gly Ala Gly Ala Gly
                85                  90                  95

Gly Ala Gly Ala Gly Gly Ala Gly Ala Gly Gly Gly Ala Gly Ala Gly
            100                 105                 110

Gly Gly Ala Gly Gly Ala Gly Gly Ala Gly Gly Ala Gly Ala Gly Gly
        115                 120                 125

Gly Ala Gly Ala Gly Gly Gly Ala Gly Gly Ala Gly Gly Ala Gly Ala
    130                 135                 140

Gly Gly Gly Ala Gly Ala Gly Gly Gly Ala Gly Gly Ala Gly Ala Gly
145                 150                 155                 160

Gly Gly Ala Gly Gly Ala Gly Ala Gly Gly Ala Gly Gly Ala Gly Ala Gly
                165                 170                 175

Ala Gly Gly Gly Ala Gly Gly Ala Gly Ala Gly Gly Gly Ala Gly Gly
            180                 185                 190

Ala Gly Gly Ala Gly Ala Gly Gly Gly Ala Gly Ala Gly Gly Ala Gly
        195                 200                 205

Gly Ala Gly Gly Ala Gly Ala Gly Gly Gly Ala Gly Ala Gly Gly Gly Ala
    210                 215                 220

Gly Gly Ala Gly Gly Ala Gly Ala Gly Gly Gly Ala Gly Ala Gly Gly Ala
225                 230                 235                 240

Gly Ala Gly Gly Ala Gly Ala Gly Gly Ala Gly Gly Ala Gly Ala Gly
                245                 250                 255

Gly Ala Gly Gly Ala Gly Ala Gly Gly Ala Gly Gly Ala Gly Ala Gly
            260                 265                 270

Gly Gly Ala Gly Gly Ala Gly Ala Gly Gly Gly Ala Gly Gly Ala Gly
        275                 280                 285
```

```
Ala Gly Gly Ala Gly Gly Ala Gly Gly Ala Gly Gly Ala Gly
    290                 295                 300
Ala Gly Gly Ala Gly Gly Ala Gly Ala Gly Gly Ala Gly Ala Gly
305                 310                 315                 320
Gly Ala Gly Ala Gly Gly Gly Arg Gly Arg Gly Ser Gly Gly
                325                 330                 335
Arg Gly Arg Gly Gly Ser Gly Gly Arg Gly Gly Gly Ser Gly Gly
    340                 345                 350
Arg Arg Gly Arg Gly Arg Glu Arg Ala Arg Gly Gly Ser Arg Glu Arg
            355                 360                 365
Ala Arg Gly Arg Gly Arg Gly Arg Gly Glu Lys Arg Pro Arg Ser Pro
370                 375                 380
Ser Ser Gln Ser Ser Ser Gly Ser Pro Pro Arg Arg Pro Pro Pro
385                 390                 395                 400
Gly Arg Arg Pro Phe Phe His Pro Val Gly Glu Ala Asp Tyr Phe Glu
                405                 410                 415
Tyr His Gln Glu Gly Gly Pro Asp Gly Glu Pro Asp Val Pro Pro Gly
            420                 425                 430
Ala Ile Glu Gln Gly Pro Ala Asp Asp Pro Gly Glu Gly Pro Ser Thr
        435                 440                 445
Gly Pro Arg Gly Gln Gly Asp Gly Gly Arg Arg Lys Lys Gly Gly Trp
    450                 455                 460
Phe Gly Lys His Arg Gly Gln Gly Gly Ser Asn Pro Lys Phe Glu Asn
465                 470                 475                 480
Ile Ala Glu Gly Leu Arg Ala Leu Leu Ala Arg Ser His Val Glu Arg
                485                 490                 495
Thr Thr Asp Glu Gly Thr Trp Val Ala Gly Val Phe Val Tyr Gly Gly
            500                 505                 510
Ser Lys Thr Ser Leu Tyr Asn Leu Arg Arg Gly Thr Ala Leu Ala Ile
        515                 520                 525
Pro Gln Cys Arg Leu Thr Pro Leu Ser Arg Leu Pro Phe Gly Met Ala
    530                 535                 540
Pro Gly Pro Gly Pro Gln Pro Gly Pro Leu Arg Glu Ser Ile Val Cys
545                 550                 555                 560
Tyr Phe Met Val Phe Leu Gln Thr His Ile Phe Ala Glu Val Leu Lys
                565                 570                 575
Asp Ala Ile Lys Asp Leu Val Met Thr Lys Pro Ala Pro Thr Cys Asn
            580                 585                 590
Ile Arg Val Thr Val Cys Ser Phe Asp Asp Gly Val Asp Leu Pro Pro
        595                 600                 605
Trp Phe Pro Pro Met Val Glu Gly Ala Ala Ala Glu Gly Asp Asp Gly
    610                 615                 620
Asp Asp Gly Asp Glu Gly Gly Asp Gly Asp Glu Gly Glu Glu Gly Gln
625                 630                 635                 640

Glu

<210> SEQ ID NO 17
<211> LENGTH: 487
<212> TYPE: PRT
<213> ORGANISM: Epstein Barr virus

<400> SEQUENCE: 17

Met Pro Thr Phe Tyr Leu Ala Leu His Gly Gly Gln Thr Tyr His Leu
1               5                   10                  15
```

-continued

```
Ile Val Asp Thr Asp Ser Leu Gly Asn Pro Ser Leu Ser Val Ile Pro
         20                  25                  30
Ser Asn Pro Tyr Gln Glu Gln Leu Ser Asp Thr Pro Leu Ile Pro Leu
         35                  40                  45
Thr Ile Phe Val Gly Glu Asn Thr Gly Val Pro Pro Pro Leu Pro Pro
         50                  55                  60
Pro Pro Pro Pro Pro Pro Pro Pro Pro Pro Pro Pro Pro Pro Pro Pro
65                  70                  75                  80
Pro Pro Pro Pro Pro Pro Pro Ser Pro Pro Pro Pro Pro Pro Pro Pro
                 85                  90                  95
Pro Pro Pro Pro Gln Arg Arg Asp Ala Trp Thr Gln Glu Pro Ser Pro
            100                 105                 110
Leu Asp Arg Asp Pro Leu Gly Tyr Asp Val Gly His Gly Pro Leu Ala
         115                 120                 125
Ser Ala Met Arg Met Leu Trp Met Ala Asn Tyr Ile Val Arg Gln Ser
         130                 135                 140
Arg Gly Asp Arg Gly Leu Ile Leu Pro Gln Gly Pro Gln Thr Ala Pro
145                 150                 155                 160
Gln Ala Arg Leu Val Gln Pro His Val Pro Pro Leu Arg Pro Thr Ala
             165                 170                 175
Pro Thr Ile Leu Ser Pro Leu Ser Gln Pro Arg Leu Thr Pro Pro Gln
             180                 185                 190
Pro Leu Met Met Pro Pro Arg Pro Thr Pro Thr Pro Leu Pro Pro
             195                 200                 205
Ala Thr Leu Thr Val Pro Pro Arg Pro Thr Arg Pro Thr Thr Leu Pro
210                 215                 220
Pro Thr Pro Leu Leu Thr Val Leu Gln Arg Pro Thr Glu Leu Gln Pro
225                 230                 235                 240
Thr Pro Ser Pro Pro Arg Met His Leu Pro Val Leu His Val Pro Asp
                 245                 250                 255
Gln Ser Met His Pro Leu Thr His Gln Ser Thr Pro Asn Asp Pro Asp
             260                 265                 270
Ser Pro Glu Pro Arg Ser Pro Thr Val Phe Tyr Asn Ile Pro Pro Met
         275                 280                 285
Pro Leu Pro Pro Ser Gln Leu Pro Pro Ala Ala Pro Ala Gln Pro
         290                 295                 300
Pro Pro Gly Val Ile Asn Asp Gln Gln Leu His His Leu Pro Ser Gly
305                 310                 315                 320
Pro Pro Trp Trp Pro Ile Cys Asp Pro Gln Pro Ser Lys Thr
             325                 330                 335
Gln Gly Gln Ser Arg Gly Gln Ser Arg Gly Arg Gly Arg Gly
             340                 345                 350
Arg Gly Arg Gly Lys Gly Lys Ser Arg Asp Lys Gln Arg Lys Pro Gly
             355                 360                 365
Gly Pro Trp Arg Pro Glu Pro Asn Thr Ser Ser Pro Ser Met Pro Glu
         370                 375                 380
Leu Ser Pro Val Leu Gly Leu His Gln Gly Gln Gly Ala Gly Asp Ser
385                 390                 395                 400
Pro Thr Pro Gly Pro Ser Asn Ala Ala Pro Val Cys Arg Asn Ser His
                 405                 410                 415
Thr Ala Thr Pro Asn Val Ser Pro Ile His Glu Pro Glu Ser His Asn
             420                 425                 430
Ser Pro Glu Ala Pro Ile Leu Phe Pro Asp Asp Trp Tyr Pro Pro Ser
```

```
            435                 440                 445
Ile Asp Pro Ala Asp Leu Asp Glu Ser Trp Asp Tyr Ile Phe Glu Thr
        450                 455                 460

Thr Glu Ser Pro Ser Ser Asp Glu Asp Tyr Val Gly Pro Ser Lys
465                 470                 475                 480

Arg Pro Arg Pro Ser Ile Gln
                485

<210> SEQ ID NO 18
<211> LENGTH: 506
<212> TYPE: PRT
<213> ORGANISM: Epstein Barr virus

<400> SEQUENCE: 18

Met Gly Asp Arg Ser Glu Val Pro Gly Pro Ala Arg Pro Gly Pro Pro
1               5                   10                  15

Gly Ile Gly Pro Glu Gly Pro Leu Gly Gln Leu Leu Arg Arg His Arg
                20                  25                  30

Ser Pro Ser Pro Thr Arg Gly Gly Gln Glu Pro Arg Arg Val Arg Arg
            35                  40                  45

Arg Val Leu Val Gln Gln Glu Glu Val Val Ser Gly Ser Pro Ser
50                  55                  60

Gly Pro Arg Gly Asp Arg Ser Glu Val Pro Gly Pro Ala Arg Pro Gly
65                  70                  75                  80

Pro Pro Gly Ile Gly Pro Glu Gly Pro Leu Gly Gln Leu Leu Arg Arg
                85                  90                  95

His Arg Ser Pro Ser Pro Thr Arg Gly Gly Gln Glu Pro Arg Arg Val
                100                 105                 110

Arg Arg Arg Val Leu Val Gln Gln Glu Glu Val Val Ser Gly Ser
            115                 120                 125

Pro Ser Gly Pro Arg Gly Asp Arg Ser Glu Val Pro Gly Pro Ala Arg
130                 135                 140

Pro Gly Pro Pro Gly Ile Gly Pro Glu Gly Pro Leu Gly Gln Leu Leu
145                 150                 155                 160

Arg Arg His Arg Ser Pro Ser Pro Thr Arg Gly Gly Gln Glu Pro Arg
                165                 170                 175

Arg Val Arg Arg Arg Val Leu Val Gln Gln Glu Glu Val Val Ser
            180                 185                 190

Gly Ser Pro Ser Gly Pro Arg Gly Asp Arg Ser Glu Val Pro Gly Pro
        195                 200                 205

Ala Arg Pro Gly Pro Pro Gly Ile Gly Pro Glu Gly Pro Leu Gly Gln
                210                 215                 220

Leu Leu Arg Arg His Arg Ser Pro Ser Pro Thr Arg Gly Gly Gln Glu
225                 230                 235                 240

Pro Arg Arg Val Arg Arg Arg Val Leu Val Gln Gln Glu Glu Val
            245                 250                 255

Val Ser Gly Ser Pro Ser Gly Pro Arg Gly Asp Arg Ser Glu Val Pro
        260                 265                 270

Gly Pro Ala Arg Pro Gly Pro Pro Gly Ile Gly Pro Glu Gly Pro Leu
            275                 280                 285

Gly Gln Leu Leu Arg Arg His Arg Ser Pro Ser Pro Thr Arg Gly Gly
        290                 295                 300

Gln Glu Pro Arg Arg Val Arg Arg Arg Val Leu Val Gln Gln Glu Glu
305                 310                 315                 320
```

```
Glu Val Val Ser Gly Ser Pro Ser Gly Pro Arg Gly Asp Arg Ser Glu
                325                 330                 335

Val Pro Gly Pro Ala Arg Pro Gly Pro Pro Gly Ile Gly Pro Glu Gly
            340                 345                 350

Pro Leu Gly Gln Leu Leu Arg Arg His Arg Ser Pro Ser Pro Thr Arg
        355                 360                 365

Gly Gly Gln Glu Pro Arg Arg Val Arg Arg Val Leu Val Gln Gln
    370                 375                 380

Glu Glu Glu Val Val Ser Gly Ser Pro Ser Pro Arg Gly Asp Arg
385                 390                 395                 400

Ser Glu Val Pro Gly Pro Ala Arg Pro Gly Pro Pro Gly Ile Gly Pro
                405                 410                 415

Glu Gly Pro Leu Gly Gln Leu Leu Arg Arg His Arg Ser Pro Ser Pro
            420                 425                 430

Thr Arg Gly Gly Gln Glu Pro Arg Arg Val Arg Arg Val Leu Val
        435                 440                 445

Gln Gln Glu Glu Glu Val Val Ser Gly Ser Pro Ser Gly Pro Leu Arg
    450                 455                 460

Pro Arg Pro Gln Pro Pro Ala Gln Ser Leu Arg Glu Trp Leu Leu Arg
465                 470                 475                 480

Ile Ser Glu Arg Phe Asp Pro His Pro Val Ala Thr Arg Arg Gln Ser
                485                 490                 495

Val Tyr Ile Glu Glu Glu Asp Glu Asp
                500                 505

<210> SEQ ID NO 19
<211> LENGTH: 375
<212> TYPE: PRT
<213> ORGANISM: Homo sapiens

<400> SEQUENCE: 19

Met Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190
```

Leu Thr Glu Arg Gly Tyr Ser Phe Thr Thr Ala Glu Arg Glu Ile
    195                 200                 205

Val Arg Asp Ile Lys Glu Lys Leu Cys Tyr Val Ala Leu Asp Phe Glu
210                 215                 220

Gln Glu Met Ala Thr Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
                260                 265                 270

Gly Ile His Glu Thr Thr Phe Asn Ser Ile Met Lys Cys Asp Val Asp
            275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
                340                 345                 350

Gln Gln Met Trp Ile Ser Lys Gln Glu Tyr Asp Glu Ser Gly Pro Ser
            355                 360                 365

Ile Val His Arg Lys Cys Phe
370                 375

<210> SEQ ID NO 20
<211> LENGTH: 375
<212> TYPE: PRT
<213> ORGANISM: Homo sapiens

<400> SEQUENCE: 20

Met Glu Glu Glu Ile Ala Ala Leu Val Ile Asp Asn Gly Ser Gly Met
1               5                   10                  15

Cys Lys Ala Gly Phe Ala Gly Asp Asp Ala Pro Arg Ala Val Phe Pro
                20                  25                  30

Ser Ile Val Gly Arg Pro Arg His Gln Gly Val Met Val Gly Met Gly
            35                  40                  45

Gln Lys Asp Ser Tyr Val Gly Asp Glu Ala Gln Ser Lys Arg Gly Ile
        50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile

```
                180                 185                 190
Leu Thr Glu Arg Gly Tyr Ser Phe Thr Thr Ala Glu Arg Glu Ile
            195                 200                 205

Val Arg Asp Ile Lys Glu Lys Leu Cys Tyr Val Ala Leu Asp Phe Glu
        210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
                245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
        275                 280                 285

Ile Arg Lys Asp Leu Tyr Ala Asn Thr Val Leu Ser Gly Gly Thr Thr
    290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
                325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
        355                 360                 365

Ile Val His Arg Lys Cys Phe
    370                 375

<210> SEQ ID NO 21
<211> LENGTH: 444
<212> TYPE: PRT
<213> ORGANISM: Homo sapiens

<400> SEQUENCE: 21

Met Arg Glu Ile Val His Ile Gln Ala Gly Gln Cys Gly Asn Gln Ile
1               5                   10                  15

Gly Ala Lys Phe Trp Glu Val Ile Ser Asp Glu His Gly Ile Asp Pro
            20                  25                  30

Thr Gly Thr Tyr His Gly Asp Ser Asp Leu Gln Leu Asp Arg Ile Ser
        35                  40                  45

Val Tyr Tyr Asn Glu Ala Thr Gly Gly Lys Tyr Val Pro Arg Ala Ile
    50                  55                  60

Leu Val Asp Leu Glu Pro Gly Thr Met Asp Ser Val Arg Ser Gly Pro
65                  70                  75                  80

Phe Gly Gln Ile Phe Arg Pro Asp Asn Phe Val Phe Gly Gln Ser Gly
                85                  90                  95

Ala Gly Asn Asn Trp Ala Lys Gly His Tyr Thr Glu Gly Ala Glu Leu
            100                 105                 110

Val Asp Ser Val Leu Asp Val Val Arg Lys Glu Ala Glu Ser Cys Asp
        115                 120                 125

Cys Leu Gln Gly Phe Gln Leu Thr His Ser Leu Gly Gly Gly Thr Gly
    130                 135                 140

Ser Gly Met Gly Thr Leu Leu Ile Ser Lys Ile Arg Glu Glu Tyr Pro
145                 150                 155                 160

Asp Arg Ile Met Asn Thr Phe Ser Val Val Pro Ser Pro Lys Val Ser
                165                 170                 175
```

Asp Thr Val Val Glu Pro Tyr Asn Ala Thr Leu Ser Val His Gln Leu
            180                 185                 190

Val Glu Asn Thr Asp Glu Thr Tyr Cys Ile Asp Asn Glu Ala Leu Tyr
        195                 200                 205

Asp Ile Cys Phe Arg Thr Leu Lys Leu Thr Thr Pro Thr Tyr Gly Asp
    210                 215                 220

Leu Asn His Leu Val Ser Ala Thr Met Ser Gly Val Thr Thr Cys Leu
225                 230                 235                 240

Arg Phe Pro Gly Gln Leu Asn Ala Asp Leu Arg Lys Leu Ala Val Asn
                245                 250                 255

Met Val Pro Phe Pro Arg Leu His Phe Phe Met Pro Gly Phe Ala Pro
            260                 265                 270

Leu Thr Ser Arg Gly Ser Gln Gln Tyr Arg Ala Leu Thr Val Pro Glu
        275                 280                 285

Leu Thr Gln Gln Val Phe Asp Ala Lys Asn Met Met Ala Ala Cys Asp
    290                 295                 300

Pro Arg His Gly Arg Tyr Leu Thr Val Ala Ala Val Phe Arg Gly Arg
305                 310                 315                 320

Met Ser Met Lys Glu Val Asp Glu Gln Met Leu Asn Val Gln Asn Lys
                325                 330                 335

Asn Ser Ser Tyr Phe Val Glu Trp Ile Pro Asn Asn Val Lys Thr Ala
            340                 345                 350

Val Cys Asp Ile Pro Pro Arg Gly Leu Lys Met Ala Val Thr Phe Ile
        355                 360                 365

Gly Asn Ser Thr Ala Ile Gln Glu Leu Phe Lys Arg Ile Ser Glu Gln
    370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ala Glu Glu
            420                 425                 430

Glu Glu Asp Phe Gly Glu Glu Ala Glu Glu Ala
        435                 440

<210> SEQ ID NO 22
<211> LENGTH: 453
<212> TYPE: PRT
<213> ORGANISM: Homo sapiens

<400> SEQUENCE: 22

Met Ser Ile Val Thr Val Gln Leu Gly Gln Cys Gly Asn Gln Ile Gly
1               5                   10                  15

Phe Glu Val Phe Asp Ala Leu Leu Ser Asp Ser His Ser Ser Gln Gly
            20                  25                  30

Leu Cys Ser Met Arg Glu Asn Glu Ala Tyr Gln Ala Ser Cys Lys Glu
        35                  40                  45

Arg Phe Phe Ser Glu Glu Asn Gly Val Pro Ile Ala Arg Ala Val
    50                  55                  60

Leu Val Asp Met Glu Pro Lys Val Ile Asn Gln Met Leu Ser Lys Ala
65                  70                  75                  80

Ala Gln Ser Gly Gln Trp Lys Tyr Gly Gln His Ala Cys Phe Cys Gln
                85                  90                  95

Lys Gln Gly Ser Gly Asn Asn Trp Ala Tyr Gly Tyr Ser Val His Gly
            100                 105                 110

```
Pro Arg His Glu Glu Ser Ile Met Asn Ile Ile Arg Lys Glu Val Glu
            115                 120                 125

Lys Cys Asp Ser Phe Ser Gly Phe Ile Ile Met Ser Met Ala Gly
        130                 135                 140

Gly Thr Gly Ser Gly Leu Gly Ala Phe Val Thr Gln Asn Leu Glu Asp
145                 150                 155                 160

Gln Tyr Ser Asn Ser Leu Lys Met Asn Gln Ile Ile Trp Pro Tyr Gly
                165                 170                 175

Thr Gly Glu Val Ile Val Gln Asn Tyr Asn Ser Ile Leu Thr Leu Ser
            180                 185                 190

His Leu Tyr Arg Ser Ser Asp Ala Leu Leu His Glu Asn Asp Ala
        195                 200                 205

Ile His Lys Ile Cys Ala Lys Leu Met Asn Ile Lys Gln Ile Ser Phe
210                 215                 220

Ser Asp Ile Asn Gln Val Leu Ala His Gln Leu Gly Ser Val Phe Gln
225                 230                 235                 240

Pro Thr Tyr Ser Ala Glu Ser Ser Phe His Tyr Arg Arg Asn Pro Leu
                245                 250                 255

Gly Asp Leu Met Glu His Leu Val Pro His Pro Glu Phe Lys Met Leu
            260                 265                 270

Ser Val Arg Asn Ile Pro His Met Ser Glu Asn Ser Leu Ala Tyr Thr
        275                 280                 285

Thr Phe Thr Trp Ala Gly Leu Leu Lys His Leu Arg Gln Met Leu Ile
290                 295                 300

Ser Asn Ala Lys Met Glu Glu Gly Ile Asp Arg His Val Trp Pro Pro
305                 310                 315                 320

Leu Ser Gly Leu Pro Pro Leu Ser Lys Met Ser Leu Asn Lys Asp Leu
                325                 330                 335

His Phe Asn Thr Ser Ile Ala Asn Leu Val Ile Leu Arg Gly Lys Asp
            340                 345                 350

Val Gln Ser Ala Asp Val Glu Gly Phe Lys Asp Pro Ala Leu Tyr Thr
        355                 360                 365

Ser Trp Leu Lys Pro Val Asn Ala Phe Asn Val Trp Lys Thr Gln Arg
370                 375                 380

Ala Phe Ser Lys Tyr Glu Lys Ser Ala Val Leu Val Ser Asn Ser Gln
385                 390                 395                 400

Phe Leu Val Lys Pro Leu Asp Met Ile Val Gly Lys Ala Trp Asn Met
                405                 410                 415

Phe Ala Ser Lys Ala Tyr Ile His Gln Tyr Thr Lys Phe Gly Ile Glu
            420                 425                 430

Glu Glu Asp Phe Leu Asp Ser Phe Thr Ser Leu Glu Gln Val Val Ala
        435                 440                 445

Ser Tyr Cys Asn Leu
    450

<210> SEQ ID NO 23
<211> LENGTH: 261
<212> TYPE: PRT
<213> ORGANISM: Homo sapiens

<400> SEQUENCE: 23

Met Ala Ser Pro Asp Trp Gly Tyr Asp Asp Lys Asn Gly Pro Glu Gln
1               5                   10                  15

Trp Ser Lys Leu Tyr Pro Ile Ala Asn Gly Asn Asn Gln Ser Pro Val
```

```
                        20                  25                  30

Asp Ile Lys Thr Ser Glu Thr Lys His Asp Thr Ser Leu Lys Pro Ile
            35                  40                  45

Ser Val Ser Tyr Asn Pro Ala Thr Ala Lys Glu Ile Ile Asn Val Gly
        50                  55                  60

His Ser Phe His Val Asn Phe Glu Asp Asn Asp Asn Arg Ser Val Leu
 65                 70                  75                  80

Lys Gly Gly Pro Phe Ser Asp Ser Tyr Arg Leu Phe Gln Phe His Phe
                85                  90                  95

His Trp Gly Ser Thr Asn Glu His Gly Ser Glu His Thr Val Asp Gly
                100                 105                 110

Val Lys Tyr Ser Ala Glu Leu His Val Ala His Trp Asn Ser Ala Lys
            115                 120                 125

Tyr Ser Ser Leu Ala Glu Ala Ala Ser Lys Ala Asp Gly Leu Ala Val
        130                 135                 140

Ile Gly Val Leu Met Lys Val Gly Glu Ala Asn Pro Lys Leu Gln Lys
145                 150                 155                 160

Val Leu Asp Ala Leu Gln Ala Ile Lys Thr Lys Gly Lys Arg Ala Pro
                165                 170                 175

Phe Thr Asn Phe Asp Pro Ser Thr Leu Leu Pro Ser Ser Leu Asp Phe
                180                 185                 190

Trp Thr Tyr Pro Gly Ser Leu Thr His Pro Pro Leu Tyr Glu Ser Val
            195                 200                 205

Thr Trp Ile Ile Cys Lys Glu Ser Ile Ser Val Ser Ser Glu Gln Leu
        210                 215                 220

Ala Gln Phe Arg Ser Leu Leu Ser Asn Val Glu Gly Asp Asn Ala Val
225                 230                 235                 240

Pro Met Gln His Asn Asn Arg Pro Thr Gln Pro Leu Lys Gly Arg Thr
                245                 250                 255

Val Arg Ala Ser Phe
            260

<210> SEQ ID NO 24
<211> LENGTH: 260
<212> TYPE: PRT
<213> ORGANISM: Homo sapiens

<400> SEQUENCE: 24

Met Ser His His Trp Gly Tyr Gly Lys His Asn Gly Pro Glu His Trp
 1               5                  10                  15

His Lys Asp Phe Pro Ile Ala Lys Gly Glu Arg Gln Ser Pro Val Asp
                20                  25                  30

Ile Asp Thr His Thr Ala Lys Tyr Asp Pro Ser Leu Lys Pro Leu Ser
            35                  40                  45

Val Ser Tyr Asp Gln Ala Thr Ser Leu Arg Ile Leu Asn Asn Gly His
        50                  55                  60

Ala Phe Asn Val Glu Phe Asp Asp Ser Gln Asp Lys Ala Val Leu Lys
 65                 70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
                100                 105                 110

Lys Tyr Ala Ala Glu Leu His Leu Val His Trp Asn Thr Lys Tyr Gly
            115                 120                 125
```

```
Asp Phe Gly Lys Ala Val Gln Gln Pro Asp Gly Leu Ala Val Leu Gly
            130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Ser Phe Lys
            260

<210> SEQ ID NO 25
<211> LENGTH: 308
<212> TYPE: PRT
<213> ORGANISM: Homo sapiens

<400> SEQUENCE: 25

Met Arg Ala Leu Val Leu Leu Ser Leu Phe Leu Leu Gly Gly Gln Gly
1               5                   10                  15

Ala Gln His Val Ser Asp Trp Thr Tyr Ser Glu Gly Ala Leu Asp Glu
                20                  25                  30

Ala His Trp Pro Gln His Tyr Pro Ala Cys Gly Gly Gln Arg Gln Ser
            35                  40                  45

Pro Ile Asn Leu Gln Arg Thr Lys Val Arg Tyr Asn Pro Ser Leu Lys
        50                  55                  60

Gly Leu Asn Met Thr Gly Tyr Glu Thr Gln Ala Gly Glu Phe Pro Met
65                  70                  75                  80

Val Asn Asn Gly His Thr Val Gln Ile Ser Leu Pro Ser Thr Met Arg
                85                  90                  95

Met Thr Val Ala Asp Gly Thr Val Tyr Ile Ala Gln Gln Met His Phe
            100                 105                 110

His Trp Gly Gly Ala Ser Ser Glu Ile Ser Gly Ser Glu His Thr Val
        115                 120                 125

Asp Gly Ile Arg His Val Ile Glu Ile His Ile Val His Tyr Asn Ser
    130                 135                 140

Lys Tyr Lys Ser Tyr Asp Ile Ala Gln Asp Ala Pro Asp Gly Leu Ala
145                 150                 155                 160

Val Leu Ala Ala Phe Val Glu Val Lys Asn Tyr Pro Glu Asn Thr Tyr
                165                 170                 175

Tyr Ser Asn Phe Ile Ser His Leu Ala Asn Ile Lys Tyr Pro Gly Gln
            180                 185                 190

Arg Thr Thr Leu Thr Gly Leu Asp Val Gln Asp Met Leu Pro Arg Asn
        195                 200                 205

Leu Gln His Tyr Tyr Thr Tyr His Gly Ser Leu Thr Thr Pro Pro Cys
    210                 215                 220

Thr Glu Asn Val His Trp Phe Val Leu Ala Asp Phe Val Lys Leu Ser
225                 230                 235                 240
```

-continued

```
Arg Thr Gln Val Trp Lys Leu Glu Asn Ser Leu Leu Asp His Arg Asn
            245                 250                 255

Lys Thr Ile His Asn Asp Tyr Arg Arg Thr Gln Pro Leu Asn His Arg
        260                 265                 270

Val Val Glu Ser Asn Phe Pro Asn Gln Glu Tyr Thr Leu Gly Ser Glu
        275                 280                 285

Phe Gln Phe Tyr Leu His Lys Ile Glu Glu Ile Leu Asp Tyr Leu Arg
        290                 295                 300

Arg Ala Leu Asn
305

<210> SEQ ID NO 26
<211> LENGTH: 312
<212> TYPE: PRT
<213> ORGANISM: Homo sapiens

<400> SEQUENCE: 26

Met Arg Met Leu Leu Ala Leu Leu Ala Leu Ser Ala Ala Arg Pro Ser
1               5                   10                  15

Ala Ser Ala Glu Ser His Trp Cys Tyr Glu Val Gln Ala Glu Ser Ser
            20                  25                  30

Asn Tyr Pro Cys Leu Val Pro Val Lys Trp Gly Gly Asn Cys Gln Lys
        35                  40                  45

Asp Arg Gln Ser Pro Ile Asn Ile Val Thr Thr Lys Ala Lys Val Asp
    50                  55                  60

Lys Lys Leu Gly Arg Phe Phe Phe Ser Gly Tyr Asp Lys Lys Gln Thr
65                  70                  75                  80

Trp Thr Val Gln Asn Asn Gly His Ser Val Met Met Leu Leu Glu Asn
                85                  90                  95

Lys Ala Ser Ile Ser Gly Gly Leu Pro Ala Pro Tyr Gln Ala Lys
            100                 105                 110

Gln Leu His Leu His Trp Ser Asp Leu Pro Tyr Lys Gly Ser Glu His
        115                 120                 125

Ser Leu Asp Gly Glu His Phe Ala Met Glu Met His Ile Val His Glu
    130                 135                 140

Lys Glu Lys Gly Thr Ser Arg Asn Val Lys Glu Ala Gln Asp Pro Glu
145                 150                 155                 160

Asp Glu Ile Ala Val Leu Ala Phe Leu Val Glu Ala Gly Thr Gln Val
                165                 170                 175

Asn Glu Gly Phe Gln Pro Leu Val Glu Ala Leu Ser Asn Ile Pro Lys
            180                 185                 190

Pro Glu Met Ser Thr Thr Met Ala Glu Ser Ser Leu Leu Asp Leu Leu
        195                 200                 205

Pro Lys Glu Glu Lys Leu Arg His Tyr Phe Arg Tyr Leu Gly Ser Leu
    210                 215                 220

Thr Thr Pro Thr Cys Asp Glu Lys Val Val Trp Thr Val Phe Arg Glu
225                 230                 235                 240

Pro Ile Gln Leu His Arg Glu Gln Ile Leu Ala Phe Ser Gln Lys Leu
                245                 250                 255

Tyr Tyr Asp Lys Glu Gln Thr Val Ser Met Lys Asp Asn Val Arg Pro
            260                 265                 270

Leu Gln Gln Leu Gly Gln Arg Thr Val Ile Lys Ser Gly Ala Pro Gly
        275                 280                 285

Arg Pro Leu Pro Trp Ala Leu Pro Ala Leu Leu Gly Pro Met Leu Ala
```

```
                290                 295                 300
Cys Leu Leu Ala Gly Phe Leu Arg
305                 310

<210> SEQ ID NO 27
<211> LENGTH: 609
<212> TYPE: PRT
<213> ORGANISM: Homo sapiens

<400> SEQUENCE: 27

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
    115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
    195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350
```

-continued

```
Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
370                 375                 380

Cys Ala Ala Asp Pro His Glu Cys Tyr Ala Lys Val Phe Asp Glu
385                 390                 395                 400

Phe Lys Pro Leu Val Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
            450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu

<210> SEQ ID NO 28
<211> LENGTH: 147
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 28

Xaa Ser Ala Gly Ala Ser Ala Leu Leu Arg Ser Gly Pro Tyr Met Pro
1               5                   10                  15

Gln Cys Asp Ala Phe Gly Ser Trp Glu Pro Val Gln Cys His Ala Gly
            20                  25                  30

Thr Gly His Cys Trp Cys Val Asp Glu Lys Gly Gly Phe Ile Pro Gly
        35                  40                  45

Ser Leu Thr Ala Arg Ser Leu Gln Ile Pro Gln Cys Pro Thr Thr Cys
    50                  55                  60

Glu Lys Ser Arg Thr Ser Gly Leu Leu Ser Ser Trp Lys Gln Ala Arg
65                  70                  75                  80

Ser Gln Glu Asn Pro Ser Pro Lys Asp Leu Phe Val Pro Ala Cys Leu
                85                  90                  95
```

```
Glu Ala Arg Gly Val Arg Cys His Ser Thr Arg Arg Trp Leu Val
            100                 105                 110

Glu Gln Ser Cys Val Arg Gln Ser Arg Ala Pro Gln Ala Leu Pro Cys
    115                 120                 125

Ser Ser Ala Asn Cys Cys Ala Arg Ala Pro Gly Ala Cys Phe His
    130                 135                 140

Gln Gly His
145

<210> SEQ ID NO 29
<211> LENGTH: 62
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 29

Xaa Ser Asp Met Gly Ser Arg Pro Glu Ser Met Gly Cys Arg Lys Asp
1               5                   10                  15

Thr Val Pro Arg Pro Ala Ser Pro Thr Glu Ala Gly Cys Val Gln Glu
            20                  25                  30

His Ser Phe Cys Gln Leu Ala Glu Ile Thr Glu Ser Ala Ser Leu Tyr
        35                  40                  45

Phe Thr Cys Thr Leu Tyr Pro Glu Ala Gln Val Cys Asp Asp
    50                  55                  60

<210> SEQ ID NO 30
<211> LENGTH: 341
<212> TYPE: PRT
<213> ORGANISM: Porphyromonas gingivalis

<400> SEQUENCE: 30

Met Thr Lys Arg Leu Phe Leu Pro Glu Trp Ala Pro Gln Glu Ala Val
1               5                   10                  15

Gln Leu Thr Trp Pro His Asp Arg Thr Asp Trp Ala Tyr Met Leu Asp
            20                  25                  30

Glu Val Glu Thr Cys Phe Val Arg Ile Ala Thr Ala Ile Leu Arg His
        35                  40                  45

Glu Arg Leu Ile Val Val Cys Pro Asp Arg Lys Arg Val Phe Gly Leu
    50                  55                  60

Leu Pro Pro Glu Leu His His Arg Leu Tyr Cys Phe Glu Leu Pro Ser
65                  70                  75                  80

Asn Asp Thr Trp Ala Arg Asp His Gly Gly Ile Ser Leu Leu Ala Asp
            85                  90                  95

Gly Arg Pro Met Ile Ala Asp Phe Ala Phe Asn Gly Trp Gly Met Lys
            100                 105                 110

Phe Ala Ala His His Asp Asn Leu Ile Thr Arg Arg Leu His Ala Leu
        115                 120                 125

Gly Leu Phe Ala Glu Gly Val Thr Leu Asp Asn Arg Leu Ala Phe Val
    130                 135                 140

Leu Glu Gly Gly Ala Leu Glu Thr Asp Gly Gly Thr Leu Leu Thr
145                 150                 155                 160

Thr Asp Ser Cys Leu Phe Glu Pro Asn Arg Asn Ala Gly Leu Ser Arg
            165                 170                 175

Thr Ala Ile Ile Asp Thr Leu Lys Glu Ser Leu Gly Val Ser Arg Val
```

```
                  180                 185                 190
Leu Ser Leu Arg His Gly Ala Leu Ala Gly Asp Asp Thr Asp Gly His
            195                 200                 205

Ile Asp Thr Leu Ala Arg Phe Val Asp Thr Arg Thr Ile Val Tyr Val
210                 215                 220

Arg Ser Glu Asp Pro Ser Asp Glu His Tyr Ser Asp Leu Thr Ala Met
225                 230                 235                 240

Glu Gln Glu Leu Lys Glu Leu Arg Arg Pro Asp Gly Gln Pro Tyr Arg
            245                 250                 255

Leu Val Pro Leu Pro Met Ala Glu Ala Leu Tyr Asp Gly Ala Asp Arg
            260                 265                 270

Leu Pro Ala Thr Tyr Ala Asn Phe Leu Ile Ile Asn Gly Ala Val Leu
            275                 280                 285

Val Pro Thr Tyr Asp Ser His Leu Asp Ala Val Ala Leu Ser Val Met
            290                 295                 300

Gln Gly Leu Phe Pro Asp Arg Glu Val Ile Gly Ile Asp Cys Arg Pro
305                 310                 315                 320

Leu Val Lys Gln His Gly Ser Leu His Cys Val Thr Met Gln Tyr Pro
            325                 330                 335

Gln Gly Phe Ile Arg
            340

<210> SEQ ID NO 31
<211> LENGTH: 435
<212> TYPE: PRT
<213> ORGANISM: Porphyromonas gingivalis

<400> SEQUENCE: 31

Met Met Arg Ser Ser Lys Ile Gly Phe Arg Ser Leu Ala Val Trp Pro
1               5                   10                  15

Phe Ser Leu Thr Ala Phe Phe Phe Leu Leu His Pro Cys Val Ser
            20                  25                  30

Ala Gln Arg Val Tyr Lys Pro Glu Asp Val Pro Asn Val Gln Leu Ala
            35                  40                  45

Asp Ser Thr Arg Leu Val Thr Asp Glu Ala Gly Leu Leu Ser Asn Ala
        50                  55                  60

Gln Glu Glu Val Met Asn Gly Arg Leu Arg Ala Ile Arg Ser Ser His
65                  70                  75                  80

Ala Val Glu Phe Ala Val Val Thr Leu Pro Ser Ile Gly Asp Ala Pro
                85                  90                  95

Leu Glu Asp Phe Thr Leu Lys Leu Ala Arg Gln Trp Gly Val Gly Asn
            100                 105                 110

Glu Lys Asn Asn Asn Gly Leu Leu Leu Val Leu Val Leu Asp Gln Arg
        115                 120                 125

Arg Val Arg Phe Glu Thr Gly Tyr Gly Leu Glu Gly Tyr Leu Pro Asp
130                 135                 140

Gly Leu Leu Ser Arg Ile Ile His Asp Arg Met Ile Pro His Phe Arg
145                 150                 155                 160

Ser Gly Asn Tyr Ala Glu Gly Leu Ser Glu Gly Val Leu Ala Val Gln
                165                 170                 175

Gln Val Leu Asp Gly Ser Tyr Asp Val Lys Pro Asp Gly Gly Asp Arg
            180                 185                 190

Ser Ala Val Ser Arg Val Ser Trp Gly Thr Ile Phe Ile Phe Tyr Cys
            195                 200                 205
```

```
Phe Phe Met Leu Leu Ala Ser Ala Ser Val Leu Tyr Gln Leu Thr Ser
    210                 215                 220

Tyr Arg Arg Gln Tyr Pro Arg Ala Thr Ala Val Glu Glu Tyr Glu Phe
225                 230                 235                 240

Leu Arg Arg Arg Ile Ser Met Leu Gly Cys Val Phe Leu Leu Leu Phe
                245                 250                 255

Pro Pro Gly Phe Ile Val Val Met Ala Ile Ile Lys Ser Arg Gln Asn
            260                 265                 270

Lys Leu Lys Lys Glu Met Ala Val Cys Pro Cys Cys His Gln His Ser
        275                 280                 285

Val His Leu Leu Asp Gln Ser Leu Glu Glu Asp Arg Tyr Leu Ser Pro
290                 295                 300

Ser Gln Gln Met Glu His Lys Leu Lys Ser Arg Asp Phe Arg Val Tyr
305                 310                 315                 320

Ala Cys Ser Ser Cys Asp His Thr Gln Ile Ile Gly Tyr Asp His Pro
                325                 330                 335

Gly Thr Ser Tyr Lys Arg Cys Pro Asn Cys Gly Thr Val Ala Leu Arg
            340                 345                 350

Tyr Met Gly Glu Lys Arg Val Arg Thr Asp Arg Gly Met Met Ile Arg
        355                 360                 365

Lys Glu Trp Arg Cys Leu Tyr Cys Gly Glu Asn His Thr Gln Glu Tyr
370                 375                 380

Arg Asp Asn Asn Asp Ala Glu Ala Ala Thr Gly Ile Leu Leu Gly
385                 390                 395                 400

Ser Leu Leu Gly Arg Gly Gly Arg Ser Gly Gly Phe Gly Gly Gly Phe
                405                 410                 415

Gly Gly Gly Gly Phe Gly Gly Gly Ser Phe Gly Gly Gly Gly Ala Ser
            420                 425                 430

Gly Gly Trp
        435

<210> SEQ ID NO 32
<211> LENGTH: 498
<212> TYPE: PRT
<213> ORGANISM: Porphyromonas gingivalis

<400> SEQUENCE: 32

Met Lys Leu Asn Lys Met Phe Leu Val Gly Ala Leu Leu Ser Leu Gly
1               5                   10                  15

Phe Ala Ser Cys Ser Lys Glu Gly Asn Gly Pro Ala Pro Asp Ser Ser
                20                  25                  30

Ser Thr Ala Asp Thr His Met Ser Val Ser Met Ser Leu Pro Gln His
            35                  40                  45

Asn Arg Ala Gly Asp Asn Asp Tyr Asn Pro Ile Gly Glu Tyr Gly Gly
        50                  55                  60

Val Asp Lys Ile Asn Asp Leu Thr Val Tyr Val Val Gly Asp Gly Lys
65                  70                  75                  80

Ile Asp Val Arg Lys Leu Ser Thr Ala Asp Leu Gln Val Asn Gln Gly
                85                  90                  95

Ala Ser Thr Thr Ser Ile Val Thr Ala Pro Phe Gln Val Lys Ser Gly
            100                 105                 110

Glu Lys Thr Val Tyr Ala Ile Val Asn Ile Thr Pro Lys Val Glu Ala
        115                 120                 125

Ala Leu Asn Ala Ala Thr Asn Ala Ala Asp Leu Lys Val Ala Tyr Glu
130                 135                 140
```

```
Ala Ala Tyr Ala Ala Phe Ser Asp Gly Ser Glu Ile Ala Thr Leu
145                 150                 155                 160

Val Asn Asn Gln Asp Gln Met Ile Met Ser Gly Lys Pro Val Val Gln
            165                 170                 175

Thr Ile Leu Ala Asn Val Ser Ala Ala Asn Ala Ser Val Gln Asn Lys
        180                 185                 190

Val Pro Ile Ile Val Lys Arg Ala Ala Ile Arg Ala Ser Met Thr Ile
            195                 200                 205

Thr Gln Gln Pro Val Asn Gly Ala Tyr Glu Ile Lys Ala Leu Arg Pro
210                 215                 220

Gly Asn Val Glu Val Gly Ile Ala Thr Val Ser Asp Leu Lys Trp Ala
225                 230                 235                 240

Val Ala Gln Tyr Glu Lys Lys Tyr Tyr Leu Gln Gln Lys Asp Asn Ala
            245                 250                 255

Leu Ser Pro Ala Ala Ser Phe Val Pro Ala Ser Thr Asn Asp Tyr Asn
            260                 265                 270

Gly Ala Asn Gly Ala Met Lys His Tyr Asp Tyr Ser Gln Leu Ala Asn
            275                 280                 285

Arg Ile Thr Val His Gln Leu Asn Ala Pro Tyr Ser Val Thr Asp Val
            290                 295                 300

Pro Asn Val Ala Tyr Lys Tyr Val Ser Glu Thr Thr His Ala Asp Asn
305                 310                 315                 320

Asp Tyr Arg Lys Gly Asn Thr Thr Tyr Ile Leu Val Lys Gly Lys Leu
            325                 330                 335

Lys Pro Val Ala Ala Met Trp Ala Asp Gly Glu Gln Ala Ala Tyr Gln
            340                 345                 350

Glu Gly Gly Asp Leu Phe Leu Gly Leu Val Thr Gly Lys Phe Tyr Ala
            355                 360                 365

Asn Glu Ala Asn Ala Asn Ala Ala Asn Pro Ala Ser Gly Gly Ala Gly
            370                 375                 380

Asn Pro Arg Val Val Thr Tyr Lys Ala Ala Ala Val Tyr Tyr Tyr Ala
385                 390                 395                 400

Trp Leu Asn Pro Asn Thr Leu Asp Pro Thr Thr Trp Thr Met Ser Pro
            405                 410                 415

Ala Arg Arg Asn Asn Ile Tyr Asn Val Asn Ile Ser Lys Phe Arg Asn
            420                 425                 430

Ile Gly Leu Ser Gly Asn Pro Phe Val Pro Thr Asp Pro Asp Pro Asn
            435                 440                 445

Asn Pro Asp Thr Pro Asp Asn Pro Asp Thr Pro Asp Pro Glu Asp Pro
            450                 455                 460

Asp Thr Pro Asn Pro Glu Glu Pro Leu Pro Val Gln Lys Thr Tyr Met
465                 470                 475                 480

Val Val Asp Val Thr Val Thr Pro Trp Thr Leu His Asn Tyr Asp Ile
            485                 490                 495

Glu Phe

<210> SEQ ID NO 33
<211> LENGTH: 237
<212> TYPE: PRT
<213> ORGANISM: Chlamydia trachomatis

<400> SEQUENCE: 33

Met Glu Ser Arg Lys Glu Met Ile Glu Val Phe Met Asn Phe Leu Asp
1               5                   10                  15
```

```
Gln Leu Asp Leu Ile Ile Gln Asn Lys His Met Leu Glu His Thr Phe
                20                  25                  30

Tyr Val Lys Trp Ser Lys Gly Glu Leu Thr Lys Glu Gln Leu Gln Ala
            35                  40                  45

Tyr Ala Lys Asp Tyr Tyr Leu His Ile Lys Ala Phe Pro Lys Tyr Leu
 50                  55                  60

Ser Ala Ile His Ser Arg Cys Asp Asp Leu Glu Ala Arg Lys Leu Leu
 65                  70                  75                  80

Leu Asp Asn Leu Met Asp Glu Glu Asn Gly Tyr Pro Asn His Ile Asp
                 85                  90                  95

Leu Trp Lys Gln Phe Val Phe Ala Leu Gly Val Thr Pro Glu Glu Leu
                100                 105                 110

Glu Ala His Glu Pro Ser Glu Ala Ala Lys Ala Lys Val Ala Thr Phe
            115                 120                 125

Met Arg Trp Cys Thr Gly Asp Ser Leu Ala Ala Gly Val Ala Ala Leu
130                 135                 140

Tyr Ser Tyr Glu Ser Gln Ile Pro Arg Ile Ala Arg Glu Lys Ile Arg
145                 150                 155                 160

Gly Leu Thr Glu Tyr Phe Gly Phe Ser Asn Pro Glu Asp Tyr Ala Tyr
                165                 170                 175

Phe Thr Glu His Glu Glu Ala Asp Val Arg His Ala Arg Glu Glu Lys
                180                 185                 190

Ala Leu Ile Glu Met Leu Leu Lys Asp Asp Ala Asp Lys Val Leu Glu
            195                 200                 205

Ala Ser Gln Glu Val Thr Gln Ser Leu Tyr Gly Phe Leu Asp Ser Phe
210                 215                 220

Leu Asp Pro Gly Thr Cys Cys Ser Cys His Gln Ser Tyr
225                 230                 235

<210> SEQ ID NO 34
<211> LENGTH: 264
<212> TYPE: PRT
<213> ORGANISM: Chlamydia trachomatis

<400> SEQUENCE: 34

Met Gly Asn Ser Gly Phe Tyr Leu Tyr Asn Thr Gln Asn Cys Val Phe
1               5                   10                  15

Ala Asp Asn Ile Lys Val Gly Gln Met Thr Glu Pro Leu Lys Asp Gln
                20                  25                  30

Gln Ile Ile Leu Gly Thr Thr Ser Thr Pro Val Ala Ala Lys Met Thr
            35                  40                  45

Ala Ser Asp Gly Ile Ser Leu Thr Val Ser Asn Asn Pro Ser Thr Asn
 50                  55                  60

Ala Ser Ile Thr Ile Gly Leu Asp Ala Glu Lys Ala Tyr Gln Leu Ile
 65                  70                  75                  80

Leu Glu Lys Leu Gly Asp Gln Ile Leu Gly Gly Ile Ala Asp Thr Ile
                 85                  90                  95

Val Asp Ser Thr Val Gln Asp Ile Leu Asp Lys Ile Thr Thr Asp Pro
                100                 105                 110

Ser Leu Gly Leu Leu Lys Ala Phe Asn Asn Phe Pro Ile Thr Asn Lys
            115                 120                 125

Ile Gln Cys Asn Gly Leu Phe Thr Pro Arg Asn Ile Glu Thr Leu Leu
130                 135                 140

Gly Gly Thr Glu Ile Gly Lys Phe Thr Val Thr Pro Lys Ser Ser Gly
```

-continued

```
            145                 150                 155                 160

Ser Met Phe Leu Val Ser Ala Asp Ile Ile Ala Ser Arg Met Glu Gly
                165                 170                 175

Gly Val Val Leu Ala Leu Val Arg Glu Gly Asp Ser Lys Pro Tyr Ala
                180                 185                 190

Ile Ser Tyr Gly Tyr Ser Ser Gly Val Pro Asn Leu Cys Ser Leu Arg
                195                 200                 205

Thr Arg Ile Ile Asn Thr Gly Leu Thr Pro Thr Thr Tyr Ser Leu Arg
                210                 215                 220

Val Gly Gly Leu Glu Ser Gly Val Val Trp Val Asn Ala Leu Ser Asn
225                 230                 235                 240

Gly Asn Asp Ile Leu Gly Ile Thr Asn Thr Ser Asn Val Ser Phe Leu
                245                 250                 255

Glu Val Ile Pro Gln Thr Asn Ala
                260

<210> SEQ ID NO 35
<211> LENGTH: 601
<212> TYPE: PRT
<213> ORGANISM: Chlamydia trachomatis

<400> SEQUENCE: 35

Met Lys Met Asn Arg Ile Trp Leu Leu Leu Thr Phe Ser Ser Ala
1               5                   10                  15

Ile His Ser Pro Val Gln Gly Glu Ser Leu Val Cys Lys Asn Ala Leu
                20                  25                  30

Gln Asp Leu Ser Phe Leu Glu His Leu Leu Gln Val Lys Tyr Ala Pro
                35                  40                  45

Lys Thr Trp Lys Glu Gln Tyr Leu Gly Trp Asp Leu Val Gln Ser Ser
                50                  55                  60

Val Ser Ala Gln Gln Lys Leu Arg Thr Gln Glu Asn Pro Ser Thr Ser
65                  70                  75                  80

Phe Cys Gln Gln Val Leu Ala Asp Phe Ile Gly Gly Leu Asn Asp Phe
                85                  90                  95

His Ala Gly Val Thr Phe Phe Ala Ile Glu Ser Ala Tyr Leu Pro Tyr
                100                 105                 110

Thr Val Gln Lys Ser Ser Asp Gly Arg Phe Tyr Phe Val Asp Ile Met
                115                 120                 125

Thr Phe Ser Ser Glu Ile Arg Val Gly Asp Glu Leu Leu Glu Val Asp
                130                 135                 140

Gly Ala Pro Val Gln Asp Val Leu Ala Thr Leu Tyr Gly Ser Asn His
145                 150                 155                 160

Lys Gly Thr Ala Ala Glu Glu Ser Ala Ala Leu Arg Thr Leu Phe Ser
                165                 170                 175

Arg Met Ala Ser Leu Gly His Lys Val Pro Ser Gly Arg Thr Thr Leu
                180                 185                 190

Lys Ile Arg Arg Pro Phe Gly Thr Thr Arg Glu Val Arg Val Lys Trp
                195                 200                 205

Arg Tyr Val Pro Glu Gly Val Gly Asp Leu Ala Thr Ile Ala Pro Ser
                210                 215                 220

Ile Arg Ala Pro Gln Leu Gln Lys Ser Met Arg Ser Phe Phe Pro Lys
225                 230                 235                 240

Lys Asp Asp Ala Phe His Arg Ser Ser Ser Leu Phe Tyr Ser Pro Met
                245                 250                 255
```

-continued

```
Val Pro His Phe Trp Ala Glu Leu Arg Asn His Tyr Ala Thr Ser Gly
            260                 265                 270

Leu Lys Ser Gly Tyr Asn Ile Gly Ser Thr Asp Gly Phe Leu Pro Val
        275                 280                 285

Ile Gly Pro Val Ile Trp Glu Ser Glu Gly Leu Phe Arg Ala Tyr Ile
    290                 295                 300

Ser Ser Val Thr Asp Gly Asp Gly Lys Ser His Lys Val Gly Phe Leu
305                 310                 315                 320

Arg Ile Pro Thr Tyr Ser Trp Gln Asp Met Glu Asp Phe Asp Pro Ser
                325                 330                 335

Gly Pro Pro Pro Trp Glu Glu Phe Ala Lys Ile Ile Gln Val Phe Ser
            340                 345                 350

Ser Asn Thr Glu Ala Leu Ile Ile Asp Gln Thr Asn Asn Pro Gly Gly
        355                 360                 365

Ser Val Leu Tyr Leu Tyr Ala Leu Leu Ser Met Leu Thr Asp Arg Pro
    370                 375                 380

Leu Glu Leu Pro Lys His Arg Met Ile Leu Thr Gln Asp Glu Val Val
385                 390                 395                 400

Asp Ala Leu Asp Trp Leu Thr Leu Leu Glu Asn Val Asp Thr Asn Val
                405                 410                 415

Glu Ser Arg Leu Ala Leu Gly Asp Asn Met Glu Gly Tyr Thr Val Asp
            420                 425                 430

Leu Gln Val Ala Glu Tyr Leu Lys Ser Phe Gly Arg Gln Val Leu Asn
        435                 440                 445

Cys Trp Ser Lys Gly Asp Ile Glu Leu Ser Thr Pro Ile Pro Leu Phe
    450                 455                 460

Gly Phe Glu Lys Ile His Pro His Pro Arg Val Gln Tyr Ser Lys Pro
465                 470                 475                 480

Ile Cys Val Leu Ile Asn Glu Gln Asp Phe Ser Cys Ala Asp Phe Phe
                485                 490                 495

Pro Val Val Leu Lys Asp Asn Asp Arg Ala Leu Ile Val Gly Thr Arg
            500                 505                 510

Thr Ala Gly Ala Gly Gly Phe Val Phe Asn Val Gln Phe Pro Asn Arg
        515                 520                 525

Thr Gly Ile Lys Thr Cys Ser Leu Thr Gly Ser Leu Ala Val Arg Glu
    530                 535                 540

His Gly Ala Phe Ile Glu Asn Ile Gly Val Glu Pro His Ile Asp Leu
545                 550                 555                 560

Pro Phe Thr Ala Asn Asp Ile Arg Tyr Lys Gly Tyr Ser Glu Tyr Leu
                565                 570                 575

Asp Lys Val Lys Lys Leu Val Cys Gln Leu Ile Asn Asn Asp Gly Thr
            580                 585                 590

Ile Ile Leu Ala Glu Asp Gly Ser Phe
        595                 600
```

<210> SEQ ID NO 36
<211> LENGTH: 111
<212> TYPE: PRT
<213> ORGANISM: Borrelia bugdorferi

<400> SEQUENCE: 36

```
Met Gln Asn Asn Thr Ile Gly Leu Gly Leu Asn Leu Leu Ser Ser Leu
1               5                   10                  15

Thr Asn Ile Ala Lys Thr Asp Thr Asn Ile Asp His Asn Tyr Ile Asn
            20                  25                  30
```

```
Thr Phe Ser Lys Val Ile Asp Phe Phe Tyr Lys Thr Tyr Ile Ser Thr
            35                  40                  45

Leu Lys Ser Met Glu Thr Ala Glu Ser Thr Lys Ile Phe Glu Glu Ile
 50                  55                  60

Gln Asp Ile Leu Lys Tyr Asn Ile Glu Ile Glu Ala Ile Ser Thr
 65                  70                  75                  80

Asp Lys Ser Lys Arg Ile Ile Thr Ser Leu Lys Ser Thr Arg Asn Lys
                85                  90                  95

Ile Met Lys Glu Tyr Ile Lys Ile Leu Lys Arg Gly Glu Asn Ala
            100                 105                 110

<210> SEQ ID NO 37
<211> LENGTH: 160
<212> TYPE: PRT
<213> ORGANISM: Borrelia bugdorferi

<400> SEQUENCE: 37

Met Arg Asn Lys Asn Ile Phe Lys Leu Phe Ala Ser Met Leu Phe
 1               5                  10                  15

Val Met Ala Cys Lys Ala Tyr Val Glu Glu Lys Lys Glu Ile Asp Ser
            20                  25                  30

Leu Met Glu Asp Val Leu Ala Leu Val Asn Asp Ser Ser Gly Gly Lys
            35                  40                  45

Phe Lys Asp Tyr Lys Asp Lys Ile Asn Glu Leu Lys Glu Asn Leu Lys
 50                  55                  60

Asp Ile Gly Asn Ala Glu Leu Lys Glu Lys Leu Leu Asn Leu Gln Asn
 65                  70                  75                  80

Ser Phe Gln Asp Lys Leu Ala Ala Lys Leu Ala Ala Leu Lys Ala Ala
                85                  90                  95

Lys Asn Thr Ile Glu Asn Ile Thr Asp Lys Asp Gln Asp Ile Ser Lys
            100                 105                 110

Arg Lys Ile Trp Ser Glu Ala Lys Leu Val Gly Val Thr Val Pro Leu
            115                 120                 125

Leu Gly Ser Asn Thr Pro Gly Asn Gly Asp Lys Met Ser Lys Asn Ala
130                 135                 140

Val Glu Gln Ile Asp Lys Ile Ile Lys Phe Leu Glu Glu Gly Thr Asn
145                 150                 155                 160

<210> SEQ ID NO 38
<211> LENGTH: 76
<212> TYPE: PRT
<213> ORGANISM: Borrelia bugdorferi

<400> SEQUENCE: 38

Met Glu Lys Ile Lys Asn Ser Leu Lys Gln Leu Phe Ser Ile Arg Lys
 1               5                  10                  15

Phe Phe Ser Thr Ser Ile Lys Gln Ile Leu Leu Asp Tyr Gln Lys Asn
            20                  25                  30

Thr Asn Ser Ile Lys Thr Glu Asp Ser Lys Leu Glu Glu Tyr Leu Asp
            35                  40                  45

Thr Ile Leu Asn Gln Phe Asn Glu Lys Asn Lys Glu Val Gly Asn Leu
 50                  55                  60

Lys Asn Thr Ile Leu Ser Ile Pro Ile Pro Thr Leu
 65                  70                  75

<210> SEQ ID NO 39
```

<211> LENGTH: 931
<212> TYPE: PRT
<213> ORGANISM: Varicella zoster virus

<400> SEQUENCE: 39

```
Met Ser Pro Cys Gly Tyr Tyr Ser Lys Trp Arg Asn Arg Asp Arg Pro
1               5                   10                  15

Glu Tyr Arg Arg Asn Leu Arg Phe Arg Arg Phe Phe Ser Ser Ile His
            20                  25                  30

Pro Asn Ala Ala Ala Gly Ser Gly Phe Asn Gly Pro Gly Val Phe Ile
        35                  40                  45

Thr Ser Val Thr Gly Val Trp Leu Cys Phe Leu Cys Ile Phe Ser Met
    50                  55                  60

Phe Val Thr Ala Val Val Ser Val Ser Pro Ser Ser Phe Tyr Glu Ser
65                  70                  75                  80

Leu Gln Val Glu Pro Thr Gln Ser Glu Asp Ile Thr Arg Ser Ala His
                85                  90                  95

Leu Gly Asp Gly Asp Glu Ile Arg Glu Ala Ile His Lys Ser Gln Asp
            100                 105                 110

Ala Glu Thr Lys Pro Thr Phe Tyr Val Cys Pro Pro Pro Thr Gly Ser
        115                 120                 125

Thr Ile Val Arg Leu Glu Pro Pro Arg Thr Cys Pro Asp Tyr His Leu
    130                 135                 140

Gly Lys Asn Phe Thr Glu Gly Ile Ala Val Val Tyr Lys Glu Asn Ile
145                 150                 155                 160

Ala Ala Tyr Lys Phe Lys Ala Thr Val Tyr Tyr Lys Asp Val Ile Val
                165                 170                 175

Ser Thr Ala Trp Ala Gly Ser Ser Tyr Thr Gln Ile Thr Asn Arg Tyr
            180                 185                 190

Ala Asp Arg Val Pro Ile Pro Val Ser Glu Ile Thr Asp Thr Ile Asp
        195                 200                 205

Lys Phe Gly Lys Cys Ser Ser Lys Ala Thr Tyr Val Arg Asn Asn His
    210                 215                 220

Lys Val Glu Ala Phe Asn Glu Asp Lys Asn Pro Gln Asp Met Pro Leu
225                 230                 235                 240

Ile Ala Ser Lys Tyr Asn Ser Val Gly Ser Lys Ala Trp His Thr Thr
                245                 250                 255

Asn Asp Thr Tyr Met Val Ala Gly Thr Pro Gly Thr Tyr Arg Thr Gly
            260                 265                 270

Thr Ser Val Asn Cys Ile Ile Glu Glu Val Glu Ala Arg Ser Ile Phe
        275                 280                 285

Pro Tyr Asp Ser Phe Gly Leu Ser Thr Gly Asp Ile Ile Tyr Met Ser
    290                 295                 300

Pro Phe Phe Gly Leu Arg Asp Gly Ala Tyr Arg Glu His Ser Asn Tyr
305                 310                 315                 320

Ala Met Asp Arg Phe His Gln Phe Glu Gly Tyr Arg Gln Arg Asp Leu
                325                 330                 335

Asp Thr Arg Ala Leu Leu Glu Pro Ala Ala Arg Asn Phe Leu Val Thr
            340                 345                 350

Pro His Leu Thr Val Gly Trp Asn Trp Lys Pro Lys Arg Thr Glu Val
        355                 360                 365

Cys Ser Leu Val Lys Trp Arg Glu Val Glu Asp Val Val Arg Asp Glu
    370                 375                 380

Tyr Ala His Asn Phe Arg Phe Thr Met Lys Thr Leu Ser Thr Thr Phe
```

-continued

```
385                 390                 395                 400
Ile Ser Glu Thr Asn Glu Phe Asn Leu Asn Gln Ile His Leu Ser Gln
                405                 410                 415

Cys Val Lys Glu Glu Ala Arg Ala Ile Ile Asn Arg Ile Tyr Thr Thr
                420                 425                 430

Arg Tyr Asn Ser Ser His Val Arg Thr Gly Asp Ile Gln Thr Tyr Leu
                435                 440                 445

Ala Arg Gly Gly Phe Val Val Phe Gln Pro Leu Leu Ser Asn Ser
            450                 455                 460

Leu Ala Arg Leu Tyr Leu Gln Glu Leu Val Arg Glu Asn Thr Asn His
465                 470                 475                 480

Ser Pro Gln Lys His Pro Thr Arg Asn Thr Arg Ser Arg Arg Ser Val
                485                 490                 495

Pro Val Glu Leu Arg Ala Asn Arg Thr Ile Thr Thr Thr Ser Ser Val
                500                 505                 510

Glu Phe Ala Met Leu Gln Phe Thr Tyr Asp His Ile Gln Glu His Val
                515                 520                 525

Asn Glu Met Leu Ala Arg Ile Ser Ser Ser Trp Cys Gln Leu Gln Asn
                530                 535                 540

Arg Glu Arg Ala Leu Trp Ser Gly Leu Phe Pro Ile Asn Pro Ser Ala
545                 550                 555                 560

Leu Ala Ser Thr Ile Leu Asp Gln Arg Val Lys Ala Arg Ile Leu Gly
                565                 570                 575

Asp Val Ile Ser Val Ser Asn Cys Pro Glu Leu Gly Ser Asp Thr Arg
                580                 585                 590

Ile Ile Leu Gln Asn Ser Met Arg Val Ser Gly Ser Thr Thr Arg Cys
                595                 600                 605

Tyr Ser Arg Pro Leu Ile Ser Ile Val Ser Leu Asn Gly Ser Gly Thr
                610                 615                 620

Val Glu Gly Gln Leu Gly Thr Asp Asn Glu Leu Ile Met Ser Arg Asp
625                 630                 635                 640

Leu Leu Glu Pro Cys Val Ala Asn His Lys Arg Tyr Phe Leu Phe Gly
                645                 650                 655

His His Tyr Val Tyr Glu Asp Tyr Arg Tyr Val Arg Glu Ile Ala
                660                 665                 670

Val His Asp Val Gly Met Ile Ser Thr Tyr Val Asp Leu Asn Leu Thr
                675                 680                 685

Leu Leu Lys Asp Arg Glu Phe Met Pro Leu Gln Val Tyr Thr Arg Asp
                690                 695                 700

Glu Leu Arg Asp Thr Gly Leu Leu Asp Tyr Ser Glu Ile Gln Arg Arg
705                 710                 715                 720

Asn Gln Met His Ser Leu Arg Phe Tyr Asp Ile Asp Lys Val Val Gln
                725                 730                 735

Tyr Asp Ser Gly Thr Ala Ile Met Gln Gly Met Ala Gln Phe Phe Gln
                740                 745                 750

Gly Leu Gly Thr Ala Gly Gln Ala Val Gly His Val Val Leu Gly Ala
                755                 760                 765

Thr Gly Ala Leu Leu Ser Thr His Gly Phe Thr Thr Phe Leu Ser
            770                 775                 780

Asn Pro Phe Gly Ala Leu Ala Val Gly Leu Leu Val Leu Ala Gly Leu
785                 790                 795                 800

Val Ala Ala Phe Phe Ala Tyr Arg Tyr Val Leu Lys Leu Lys Thr Ser
                805                 810                 815
```

-continued

```
Pro Met Lys Ala Leu Tyr Pro Leu Thr Thr Lys Gly Leu Lys Gln Leu
            820                 825                 830

Pro Glu Gly Met Asp Pro Phe Ala Glu Lys Pro Asn Ala Thr Asp Thr
        835                 840                 845

Pro Ile Glu Glu Ile Gly Asp Ser Gln Asn Thr Glu Pro Ser Val Asn
    850                 855                 860

Ser Gly Phe Asp Pro Asp Lys Phe Arg Glu Ala Gln Glu Met Ile Lys
865                 870                 875                 880

Tyr Met Thr Leu Val Ser Ala Ala Glu Arg Gln Glu Ser Lys Ala Arg
                885                 890                 895

Lys Lys Asn Lys Thr Ser Ala Leu Leu Thr Ser Arg Leu Thr Gly Leu
            900                 905                 910

Ala Leu Arg Asn Arg Arg Gly Tyr Ser Arg Val Arg Thr Glu Asn Val
        915                 920                 925

Thr Gly Val
    930

<210> SEQ ID NO 40
<211> LENGTH: 102
<212> TYPE: PRT
<213> ORGANISM: Varicella zoster virus

<400> SEQUENCE: 40

Met Ala Gly Gln Asn Thr Met Glu Gly Glu Ala Val Ala Leu Leu Met
1               5                   10                  15

Glu Ala Val Val Thr Pro Arg Ala Gln Pro Asn Asn Thr Thr Ile Thr
            20                  25                  30

Ala Ile Gln Pro Ser Arg Ser Ala Glu Lys Cys Tyr Tyr Ser Asp Ser
        35                  40                  45

Glu Asn Glu Thr Ala Asp Glu Phe Leu Arg Arg Ile Gly Lys Tyr Gln
    50                  55                  60

His Lys Ile Tyr His Arg Lys Lys Phe Cys Tyr Ile Thr Leu Ile Ile
65                  70                  75                  80

Val Phe Val Phe Ala Met Thr Gly Ala Ala Phe Ala Leu Gly Tyr Ile
                85                  90                  95

Thr Ser Gln Phe Val Gly
            100

<210> SEQ ID NO 41
<211> LENGTH: 108
<212> TYPE: PRT
<213> ORGANISM: Varicella zoster virus

<400> SEQUENCE: 41

Met Ser Arg Val Ser Glu Tyr Gly Val Pro Glu Gly Val Arg Glu Ser
1               5                   10                  15

Asp Ser Asp Thr Asp Ser Val Phe Met Tyr Gln His Thr Glu Leu Met
            20                  25                  30

Gln Asn Asn Ala Ser Pro Leu Val Arg Ala Arg Pro Pro Ala Val
        35                  40                  45

Leu Ile Pro Leu Val Asp Val Pro Arg Pro Arg Ser Arg Arg Lys Ala
    50                  55                  60

Ser Ala Gln Leu Lys Met Gln Met Asp Arg Leu Cys Asn Val Leu Gly
65                  70                  75                  80

Val Val Leu Gln Met Ala Thr Leu Ala Leu Val Thr Tyr Ile Ala Phe
                85                  90                  95
```

```
Val Val His Thr Arg Ala Thr Ser Cys Lys Arg Glu
            100                 105

<210> SEQ ID NO 42
<211> LENGTH: 117
<212> TYPE: PRT
<213> ORGANISM: Hepatitis C virus

<400> SEQUENCE: 42

Arg Cys Phe Asp Ser Thr Val Thr Glu His Asp Ile Arg Thr Glu Glu
1               5                   10                  15

Glu Ile Tyr Gln Cys Cys Asp Leu Glu Pro Glu Ala Arg Lys Ala Ile
            20                  25                  30

Ser Ala Leu Thr Glu Arg Leu Tyr Ile Gly Gly Pro Met Tyr Asn Ser
            35                  40                  45

Lys Gly Leu Gln Cys Gly Tyr Arg Arg Cys Arg Ala Ser Gly Val Leu
        50                  55                  60

Pro Thr Ser Phe Gly Asn Thr Ile Thr Cys Tyr Ile Lys Ala Thr Ala
65                  70                  75                  80

Ala Ser Arg Ala Ala Gly Leu Lys Asp Pro Ser Phe Leu Val Cys Gly
                85                  90                  95

Asp Asp Leu Val Val Ile Ala Glu Ser Cys Gly Val Glu Glu Asp Arg
            100                 105                 110

Ala Ala Leu Arg Ala
            115

<210> SEQ ID NO 43
<211> LENGTH: 74
<212> TYPE: PRT
<213> ORGANISM: Hepatitis C virus

<400> SEQUENCE: 43

Ile Tyr Gln Cys Cys Asn Leu Glu Pro Glu Ala Arg Lys Val Ile Ser
1               5                   10                  15

Ser Leu Thr Glu Arg Leu Tyr Cys Gly Gly Pro Met Phe Asn Ser Lys
            20                  25                  30

Gly Ala Gln Cys Gly Tyr Arg Arg Cys Arg Ala Ser Gly Val Leu Pro
            35                  40                  45

Thr Ser Phe Gly Asn Thr Ile Thr Cys Tyr Ile Lys Ala Thr Ala Ala
        50                  55                  60

Cys Lys Ala Ala Gly Leu Arg Asn Pro Asp
65                  70

<210> SEQ ID NO 44
<211> LENGTH: 82
<212> TYPE: PRT
<213> ORGANISM: Hepatitis C virus

<400> SEQUENCE: 44

Arg Val Glu Glu Glu Ile Tyr Gln Cys Cys Asn Leu Glu Pro Glu Ala
1               5                   10                  15

Arg Lys Val Ile Ser Ser Leu Thr Glu Arg Leu Tyr Cys Gly Gly Pro
            20                  25                  30

Met Phe Asn Ser Lys Gly Ala Gln Cys Gly Tyr Arg Arg Cys Arg Ala
            35                  40                  45

Ser Gly Val Leu Pro Thr Ser Phe Gly Asn Thr Ile Thr Cys Tyr Ile
        50                  55                  60
```

```
Lys Ala Thr Ala Ala Ala Lys Ala Ser Gly Leu Arg Asn Pro Asp Phe
 65                  70                  75                  80

Leu Val

<210> SEQ ID NO 45
<211> LENGTH: 115
<212> TYPE: PRT
<213> ORGANISM: Hepatitis C virus

<400> SEQUENCE: 45

Gly Gly Lys Tyr Val Gln Met Met Leu Leu Thr Leu Gly Arg Trp Thr
  1               5                  10                  15

Gly Thr Tyr Ile Tyr Asp His Leu Thr Pro Leu Arg Asp Trp Ala His
                 20                  25                  30

Glu Gly Leu Arg Asp Leu Ala Val Ala Val Glu Pro Val Val Phe Ser
             35                  40                  45

Asp Met Glu Thr Lys Ile Ile Thr Trp Gly Ala Asp Thr Ala Ala Cys
 50                  55                  60

Gly Asp Ile Ile Leu Gly Leu Pro Val Ser Ala Arg Lys Gly Arg Glu
 65                  70                  75                  80

Ile Phe Leu Gly Pro Ala Asp Ser Leu Glu Gly Gln Gly Trp Arg Leu
                 85                  90                  95

Leu Ala Pro Ile Thr Ala Tyr Ser Gln Gln Thr Arg Gly Leu Leu Gly
            100                 105                 110

Cys Ile Val
        115

<210> SEQ ID NO 46
<211> LENGTH: 217
<212> TYPE: PRT
<213> ORGANISM: Hepatitis C virus

<400> SEQUENCE: 46

Met Asp Arg Glu Met Ala Pro Ser Cys Gly Gly Met Val Phe Leu Gly
  1               5                  10                  15

Leu Val Leu Leu Thr Leu Ser Pro His Tyr Lys Val Phe Leu Ala Arg
                 20                  25                  30

Leu Ile Arg Trp Leu Gln Tyr Phe Leu Thr Ile Ala Glu Ala His Leu
             35                  40                  45

Gln Val Trp Val Ser Pro Leu Asn Ile Arg Gly Gly Arg Asp Ala Val
 50                  55                  60

Ile Leu Leu Thr Cys Val Ile His Pro Gly Leu Ile Phe Asp Ile Thr
 65                  70                  75                  80

Lys Leu Leu Leu Ala Thr Leu Gly Pro Leu Leu Val Leu Gln Ala Gly
                 85                  90                  95

Ile Ala Arg Val Pro Tyr Phe Val Arg Ala His Gly Leu Ile Arg Ala
            100                 105                 110

Cys Met Leu Leu Arg Lys Val Ala Gly Gly His Tyr Val Gln Met Ala
            115                 120                 125

Leu Met Lys Leu Ala Ala Leu Thr Gly Thr Tyr Leu Tyr Asp His Leu
130                 135                 140

Ala Pro Leu Gln Tyr Trp Ala His Ala Gly Leu Arg Asp Leu Ala Val
145                 150                 155                 160

Ala Val Glu Pro Val Ile Phe Ser Asp Met Glu Ile Lys Ile Ile Thr
                165                 170                 175

Trp Gly Ala Asp Thr Ala Ala Cys Gly Asp Ile Ile Gln Gly Leu Pro
```

```
                      180             185                 190
Val Ser Ala Arg Arg Gly Arg Glu Ile Leu Leu Gly Pro Ala Asp Ser
                195                 200                 205

Leu Asp Gly Gln Gly Trp Arg Leu Leu
            210                 215

<210> SEQ ID NO 47
<211> LENGTH: 70
<212> TYPE: PRT
<213> ORGANISM: Hepatitis C virus

<400> SEQUENCE: 47

Ala Ala Trp Tyr Ile Lys Gly Arg Leu Val Pro Gly Ala Ala Tyr Ala
1               5                   10                  15

Leu Tyr Gly Val Trp Pro Leu Leu Leu Leu Leu Ala Leu Pro Pro Pro
                20                  25                  30

Arg Ala Tyr Ala Met Asp Arg Glu Met Ala Ala Ser Cys Gly Gly Val
            35                  40                  45

Val Phe Ala Gly Leu Val Phe Leu Thr Leu Ser Pro Tyr Tyr Lys Val
    50                  55                  60

Leu Leu Ala Lys Leu Ile
65                  70

<210> SEQ ID NO 48
<211> LENGTH: 514
<212> TYPE: PRT
<213> ORGANISM: Helicobacter pylori

<400> SEQUENCE: 48

Met Ser Phe Arg Ile Asn Thr Asn Ile Ala Ala Leu Thr Ser His Ala
1               5                   10                  15

Val Gly Val Gln Asn Asn Arg Asp Leu Ser Ser Ser Leu Glu Lys Leu
                20                  25                  30

Ser Ser Gly Leu Arg Ile Asn Lys Ala Ala Asp Asp Ser Ser Gly Met
            35                  40                  45

Ala Ile Ala Asp Ser Leu Arg Ser Gln Ser Ala Asn Leu Gly Gln Ala
    50                  55                  60

Ile Arg Asn Ala Asn Asp Ala Ile Gly Met Val Gln Thr Ala Asp Lys
65                  70                  75                  80

Ala Met Asp Glu Gln Ile Lys Ile Leu Asp Thr Ile Lys Thr Lys Ala
                85                  90                  95

Val Gln Ala Ala Gln Asp Gly Gln Thr Leu Glu Ser Arg Arg Ala Leu
            100                 105                 110

Gln Ser Asp Ile Gln Arg Leu Leu Glu Glu Leu Asp Asn Ile Ala Asn
        115                 120                 125

Thr Thr Ser Phe Asn Gly Gln Gln Met Leu Ser Gly Ser Phe Ser Asn
    130                 135                 140

Lys Glu Phe Gln Ile Gly Ala Tyr Ser Asn Ala Thr Val Lys Ala Ser
145                 150                 155                 160

Ile Gly Ser Thr Ser Ser Asp Lys Ile Gly His Val Arg Met Glu Thr
                165                 170                 175

Ser Ser Phe Ser Gly Ala Gly Met Leu Ala Ser Ala Ala Gln Asn
            180                 185                 190

Leu Thr Glu Val Gly Leu Asn Phe Lys Gln Val Asn Gly Val Asn Asp
        195                 200                 205

Tyr Lys Ile Glu Thr Val Arg Ile Ser Thr Ser Ala Gly Thr Gly Ile
```

Gly Ala Leu Ser Glu Ile Ile Asn Arg Phe Ser Asn Thr Leu Gly Val
225                 230                 235                 240

Arg Ala Ser Tyr Asn Val Met Ala Thr Gly Gly Thr Pro Val Gln Ser
                245                 250                 255

Gly Thr Val Arg Glu Leu Thr Ile Asn Gly Val Glu Ile Gly Thr Val
            260                 265                 270

Asn Asp Val His Lys Asn Asp Ala Asp Gly Arg Leu Thr Asn Ala Ile
        275                 280                 285

Asn Ser Val Lys Asp Arg Thr Gly Val Glu Ala Ser Leu Asp Ile Gln
    290                 295                 300

Gly Arg Ile Asn Leu His Ser Ile Asp Gly Arg Ala Ile Ser Val His
305                 310                 315                 320

Ala Ala Ser Ala Ser Gly Gln Val Phe Gly Gly Asn Phe Ala Gly
                325                 330                 335

Ile Ser Gly Thr Gln His Ala Val Ile Gly Arg Leu Thr Leu Thr Arg
            340                 345                 350

Thr Asp Ala Arg Asp Ile Ile Val Ser Gly Val Asn Phe Ser His Val
        355                 360                 365

Gly Phe His Ser Ala Gln Gly Val Ala Glu Tyr Thr Val Asn Leu Arg
    370                 375                 380

Ala Val Arg Gly Ile Phe Asp Ala Asn Val Ala Ser Ala Gly Ala
385                 390                 395                 400

Asn Ala Asn Gly Ala Gln Ala Glu Thr Asn Ser Gln Gly Ile Gly Ala
                405                 410                 415

Gly Val Thr Ser Leu Lys Gly Ala Met Ile Val Met Asp Met Ala Asp
            420                 425                 430

Ser Ala Arg Thr Gln Leu Asp Lys Ile Arg Ser Asp Met Gly Ser Val
        435                 440                 445

Gln Met Glu Leu Val Thr Thr Ile Asn Asn Ile Ser Val Thr Gln Val
    450                 455                 460

Asn Val Lys Ala Ala Glu Ser Gln Ile Arg Asp Val Asp Phe Ala Glu
465                 470                 475                 480

Glu Ser Ala Asn Phe Ser Lys Tyr Asn Ile Leu Ala Gln Ser Gly Ser
                485                 490                 495

Phe Ala Met Ala Gln Ala Asn Ala Val Gln Gln Asn Val Leu Arg Leu
            500                 505                 510

Leu Gln

<210> SEQ ID NO 49
<211> LENGTH: 510
<212> TYPE: PRT
<213> ORGANISM: Helicobacter pylori

<400> SEQUENCE: 49

Met Ala Phe Gln Val Asn Thr Asn Ile Asn Ala Met Asn Ala His Val
1               5                   10                  15

Gln Ser Ala Leu Thr Gln Asn Ala Leu Lys Thr Ser Leu Glu Arg Leu
            20                  25                  30

Ser Ser Gly Leu Arg Ile Asn Lys Ala Ala Asp Asp Ala Ser Gly Met
        35                  40                  45

Thr Val Ala Asp Ser Leu Arg Ser Gln Ala Ser Ser Leu Gly Gln Ala
    50                  55                  60

Ile Ala Asn Thr Asn Asp Gly Met Gly Ile Ile Gln Val Ala Asp Lys

-continued

```
                65                  70                  75                  80
Ala Met Asp Glu Gln Leu Lys Ile Leu Asp Thr Val Lys Val Lys Ala
                    85                  90                  95

Thr Gln Ala Ala Gln Asp Gly Gln Thr Thr Glu Ser Arg Lys Ala Ile
                100                 105                 110

Gln Ser Asp Ile Val Arg Leu Ile Gln Gly Leu Asp Asn Ile Gly Asn
                115                 120                 125

Thr Thr Thr Tyr Asn Gly Gln Ala Leu Leu Ser Gly Gln Phe Thr Asn
            130                 135                 140

Lys Glu Phe Gln Val Gly Ala Tyr Ser Asn Gln Ser Ile Lys Ala Ser
145                 150                 155                 160

Ile Gly Ser Thr Thr Ser Asp Lys Ile Gly Gln Val Arg Ile Ala Thr
                    165                 170                 175

Gly Ala Leu Ile Thr Ala Ser Gly Asp Ile Ser Leu Thr Phe Lys Gln
                180                 185                 190

Val Asp Gly Val Asn Asp Val Thr Leu Glu Ser Val Lys Val Ser Ser
                195                 200                 205

Ser Ala Gly Thr Gly Ile Gly Val Leu Ala Glu Val Ile Asn Lys Asn
            210                 215                 220

Ser Asn Arg Thr Gly Val Lys Ala Tyr Ala Ser Val Ile Thr Thr Ser
225                 230                 235                 240

Asp Val Ala Val Gln Ser Gly Ser Leu Ser Asn Leu Thr Leu Asn Gly
                    245                 250                 255

Ile His Leu Gly Asn Ile Ala Asp Ile Lys Lys Asn Asp Ser Asp Gly
                260                 265                 270

Arg Leu Val Ala Ala Ile Asn Ala Val Thr Ser Glu Thr Gly Val Glu
            275                 280                 285

Ala Tyr Thr Asp Gln Lys Gly Arg Leu Asn Leu Arg Ser Ile Asp Gly
            290                 295                 300

Arg Gly Ile Glu Ile Lys Thr Asp Ser Val Ser Asn Gly Pro Ser Ala
305                 310                 315                 320

Leu Thr Met Val Asn Gly Gly Gln Asp Leu Thr Lys Gly Ser Thr Asn
                    325                 330                 335

Tyr Gly Arg Leu Ser Leu Thr Arg Leu Asp Ala Lys Ser Ile Asn Val
                340                 345                 350

Val Ser Ala Ser Asp Ser Gln His Leu Gly Phe Thr Ala Ile Gly Phe
            355                 360                 365

Gly Glu Ser Gln Val Ala Glu Thr Thr Val Asn Leu Arg Asp Val Thr
            370                 375                 380

Gly Asn Phe Asn Ala Asn Val Lys Ser Ala Ser Gly Ala Asn Tyr Asn
385                 390                 395                 400

Ala Val Ile Ala Ser Gly Asn Gln Ser Leu Gly Ser Gly Val Thr Thr
                    405                 410                 415

Leu Arg Gly Ala Met Val Val Ile Asp Ile Ala Glu Ser Ala Met Lys
                420                 425                 430

Met Leu Asp Lys Val Arg Ser Asp Leu Gly Ser Val Gln Asn Gln Met
            435                 440                 445

Ile Ser Thr Val Asn Asn Ile Ser Ile Thr Gln Val Asn Val Lys Ala
            450                 455                 460

Ala Glu Ser Gln Ile Arg Asp Val Asp Phe Ala Glu Glu Ser Ala Asn
465                 470                 475                 480

Phe Asn Lys Asn Asn Ile Leu Ala Gln Ser Gly Ser Tyr Ala Met Ser
                    485                 490                 495
```

```
Gln Ala Asn Thr Val Gln Gln Asn Ile Leu Arg Leu Leu Thr
                500                 505                 510

<210> SEQ ID NO 50
<211> LENGTH: 342
<212> TYPE: PRT
<213> ORGANISM: Helicobacter pylori

<400> SEQUENCE: 50

Met Lys Arg Val Phe Leu Tyr Leu Ile Phe Val Leu Ala Phe His Lys
1               5                   10                  15

Leu Leu Ala Glu Lys Ile Gly Asp Ile Ala Ser Val Val Gly Val Arg
            20                  25                  30

Asp Asn Gln Leu Ile Gly Tyr Gly Leu Val Ile Gly Leu Asn Gly Thr
        35                  40                  45

Gly Asp Lys Ser Gly Ser Lys Phe Thr Met Gln Ser Ile Ser Asn Met
    50                  55                  60

Leu Glu Ser Val Asn Val Lys Ile Ser Ala Asp Asp Ile Lys Ser Lys
65                  70                  75                  80

Asn Val Ala Ala Val Met Ile Thr Ala Ser Leu Pro Pro Phe Ala Arg
                85                  90                  95

Gln Gly Asp Lys Ile Asp Ile His Ile Ser Ser Ile Gly Asp Ala Lys
            100                 105                 110

Ser Ile Gln Gly Gly Thr Leu Val Met Thr Pro Leu Asn Ala Val Asp
        115                 120                 125

Gly Asn Ile Tyr Ala Leu Ala Gln Gly Ala Ile Thr Ser Gly Asn Ser
    130                 135                 140

Asn Asn Leu Leu Ser Ala Asn Ile Ile Asn Gly Ala Thr Ile Glu Arg
145                 150                 155                 160

Glu Val Ser Tyr Asp Leu Phe His Lys Asn Ala Met Val Leu Ser Leu
                165                 170                 175

Lys Ser Pro Asn Phe Lys Asn Ala Ile Gln Val Gln Asn Thr Leu Asn
            180                 185                 190

Lys Val Phe Gly Asn Lys Val Ala Ile Ala Leu Asp Pro Lys Thr Ile
        195                 200                 205

Gln Ile Thr Arg Pro Glu Arg Phe Ser Met Val Glu Phe Leu Ala Leu
    210                 215                 220

Val Gln Glu Ile Pro Ile Asn Tyr Ser Ala Lys Asn Lys Ile Ile Val
225                 230                 235                 240

Asp Glu Lys Ser Gly Thr Ile Val Ser Gly Val Asp Ile Met Val His
                245                 250                 255

Pro Ile Val Val Thr Ser Gln Asp Ile Thr Leu Lys Ile Thr Lys Glu
            260                 265                 270

Pro Leu Asn Asp Ser Lys Asn Thr Gln Asp Leu Asp Asn Asn Met Ser
        275                 280                 285

Leu Asp Thr Ala His Asn Thr Leu Ser Ser Asn Gly Lys Ser Ile Thr
    290                 295                 300

Ile Ala Gly Val Val Lys Ala Leu Gln Lys Ile Gly Val Ser Ala Lys
305                 310                 315                 320

Gly Met Val Ser Ile Leu Gln Ala Leu Lys Lys Ser Gly Ala Ile Ser
                325                 330                 335

Ala Glu Met Glu Ile Leu
            340
```

```
<210> SEQ ID NO 51
<211> LENGTH: 1063
<212> TYPE: PRT
<213> ORGANISM: Rubella virus

<400> SEQUENCE: 51

Met Ala Ser Thr Thr Pro Ile Thr Met Glu Asp Leu Gln Lys Ala Leu
1               5                   10                  15

Glu Ala Gln Ser Arg Ala Leu Arg Ala Glu Leu Ala Ala Gly Ala Ser
            20                  25                  30

Gln Ser Arg Arg Pro Arg Pro Pro Arg Gln Arg Asp Ser Ser Thr Ser
        35                  40                  45

Gly Asp Asp Ser Gly Arg Asp Ser Gly Gly Pro Arg Arg Arg Arg Gly
    50                  55                  60

Asn Arg Gly Arg Gly Gln Arg Arg Asp Trp Ser Arg Ala Pro Pro Pro
65                  70                  75                  80

Pro Glu Glu Arg Gln Glu Thr Arg Ser Gln Thr Pro Ala Pro Lys Pro
                85                  90                  95

Ser Arg Ala Pro Pro Gln Gln Pro Gln Pro Pro Arg Met Gln Thr Gly
            100                 105                 110

Arg Gly Gly Ser Ala Pro Arg Pro Glu Leu Gly Pro Pro Thr Asn Pro
        115                 120                 125

Phe Gln Ala Ala Val Ala Arg Gly Leu Arg Pro Pro Leu His Asp Pro
    130                 135                 140

Asp Thr Glu Ala Pro Thr Glu Ala Cys Val Thr Ser Trp Leu Trp Ser
145                 150                 155                 160

Glu Gly Glu Gly Ala Val Phe Tyr Arg Val Asp Leu His Phe Thr Asn
                165                 170                 175

Leu Gly Thr Pro Pro Leu Asp Glu Asp Gly Arg Trp Asp Pro Ala Leu
            180                 185                 190

Met Tyr Asn Pro Cys Gly Pro Glu Pro Pro Ala His Val Val Arg Ala
        195                 200                 205

Tyr Asn Gln Pro Ala Gly Asp Val Arg Gly Val Trp Gly Lys Gly Glu
    210                 215                 220

Arg Thr Tyr Ala Glu Gln Asp Phe Arg Val Gly Gly Thr Arg Trp His
225                 230                 235                 240

Arg Leu Leu Arg Met Pro Val Arg Gly Leu Asp Gly Asp Ser Ala Pro
                245                 250                 255

Leu Pro Pro His Thr Thr Glu Arg Ile Glu Thr Arg Ser Ala Arg His
            260                 265                 270

Pro Trp Arg Ile Arg Phe Gly Ala Pro Gln Ala Phe Leu Ala Gly Leu
        275                 280                 285

Leu Leu Ala Thr Val Ala Val Gly Thr Ala Arg Ala Gly Leu Gln Pro
    290                 295                 300

Arg Ala Asp Met Ala Ala Pro Pro Thr Leu Pro Gln Pro Pro Cys Ala
305                 310                 315                 320

His Gly Gln His Tyr Gly His His His Gln Leu Pro Phe Leu Gly
                325                 330                 335

His Asp Gly His His Gly Gly Thr Leu Arg Val Gly Gln His Tyr Arg
            340                 345                 350

Asn Ala Ser Asp Val Leu Pro Gly His Trp Leu Gln Gly Gly Trp Gly
        355                 360                 365

Cys Tyr Asn Leu Ser Asp Trp His Gln Gly Thr His Val Cys His Thr
    370                 375                 380
```

```
Lys His Met Asp Phe Trp Cys Val Glu His Asp Arg Pro Pro Ala
385                 390                 395                 400

Thr Pro Thr Pro Leu Thr Thr Ala Ala Asn Ser Thr Thr Ala Ala Thr
                405                 410                 415

Pro Ala Thr Ala Pro Ala Pro Cys His Ala Gly Leu Asn Asp Ser Cys
            420                 425                 430

Gly Gly Phe Leu Ser Gly Cys Gly Pro Met Arg Leu Arg His Gly Ala
        435                 440                 445

Asp Thr Arg Cys Gly Arg Leu Ile Cys Gly Leu Ser Thr Thr Ala Gln
    450                 455                 460

Tyr Pro Pro Thr Arg Phe Gly Cys Ala Met Arg Trp Gly Leu Pro Pro
465                 470                 475                 480

Trp Glu Leu Val Val Leu Thr Ala Arg Pro Glu Asp Gly Trp Thr Cys
                485                 490                 495

Arg Gly Val Pro Ala His Pro Gly Ala Arg Cys Pro Glu Leu Val Ser
            500                 505                 510

Pro Met Gly Arg Ala Thr Cys Ser Pro Ala Ser Ala Leu Trp Leu Ala
        515                 520                 525

Thr Ala Asn Ala Leu Ser Leu Asp His Ala Leu Ala Ala Phe Val Leu
530                 535                 540

Leu Val Pro Trp Val Leu Ile Phe Met Val Cys Arg Arg Ala Cys Arg
545                 550                 555                 560

Arg Arg Gly Ala Ala Ala Ala Leu Thr Ala Val Val Leu Gln Gly Tyr
                565                 570                 575

Asn Pro Pro Ala Tyr Gly Glu Glu Ala Phe Thr Tyr Leu Cys Thr Ala
            580                 585                 590

Pro Gly Cys Ala Thr Gln Ala Pro Val Pro Val Arg Leu Ala Gly Val
        595                 600                 605

Arg Phe Glu Ser Lys Ile Val Asp Gly Gly Cys Phe Ala Pro Trp Asp
610                 615                 620

Leu Glu Ala Thr Gly Ala Cys Ile Cys Glu Ile Pro Thr Asp Val Ser
625                 630                 635                 640

Cys Glu Gly Leu Gly Ala Trp Val Pro Ala Ala Pro Cys Ala Arg Ile
                645                 650                 655

Trp Asn Gly Thr Gln Arg Ala Cys Thr Phe Trp Ala Val Asn Ala Tyr
            660                 665                 670

Ser Ser Gly Gly Tyr Ala Gln Leu Ala Ser Tyr Phe Asn Pro Gly Gly
        675                 680                 685

Ser Tyr Tyr Lys Gln Tyr His Pro Thr Ala Cys Glu Val Glu Pro Ala
690                 695                 700

Phe Gly His Ser Asp Ala Ala Cys Trp Gly Phe Pro Thr Asp Thr Val
705                 710                 715                 720

Met Ser Val Phe Ala Leu Ala Ser Tyr Val Gln His Pro His Lys Thr
                725                 730                 735

Val Arg Val Lys Phe His Thr Glu Thr Arg Thr Val Trp Gln Leu Ser
            740                 745                 750

Val Ala Gly Val Ser Cys Asn Val Thr Thr Glu His Pro Phe Cys Asn
        755                 760                 765

Thr Pro His Gly Gln Leu Glu Val Gln Val Pro Pro Asp Pro Gly Asp
    770                 775                 780

Leu Val Glu Tyr Ile Met Asn Tyr Thr Gly Asn Gln Gln Ser Arg Trp
785                 790                 795                 800

Gly Leu Gly Ser Pro Asn Cys His Gly Pro Asp Trp Ala Ser Pro Val
```

```
                805                 810                 815
Cys Gln Arg His Ser Pro Asp Cys Ser Arg Leu Val Gly Ala Thr Pro
            820                 825                 830
Glu Arg Pro Arg Leu Arg Leu Val Asp Ala Asp Pro Leu Leu Arg
            835                 840                 845
Thr Ala Pro Gly Pro Gly Glu Val Trp Val Thr Pro Val Ile Gly Ser
850                 855                 860
Gln Ala Arg Lys Cys Gly Leu His Ile Arg Ala Gly Pro Tyr Gly His
865                 870                 875                 880
Ala Thr Val Glu Met Pro Glu Trp Ile His Ala His Thr Thr Ser Asp
            885                 890                 895
Pro Trp His Pro Pro Gly Pro Leu Gly Leu Lys Phe Lys Thr Val Arg
            900                 905                 910
Pro Val Ala Leu Pro Arg Thr Leu Ala Pro Pro Arg Asn Val Arg Val
            915                 920                 925
Thr Gly Cys Tyr Gln Cys Gly Thr Pro Ala Leu Val Glu Gly Leu Ala
            930                 935                 940
Pro Gly Gly Gly Asn Cys His Leu Thr Val Asn Gly Glu Asp Leu Gly
945                 950                 955                 960
Ala Val Pro Pro Gly Lys Phe Val Thr Ala Ala Leu Leu Asn Thr Pro
                965                 970                 975
Pro Pro Tyr Gln Val Ser Cys Gly Gly Glu Ser Asp Arg Ala Thr Ala
            980                 985                 990
Arg Val Ile Asp Pro Ala Ala Gln Ser Phe Thr Gly Val Val Tyr Gly
            995                 1000                1005
Thr His Thr Thr Ala Val Ser Glu Thr Arg Gln Thr Trp Ala Glu
    1010                1015                1020
Trp Ala Ala Ala His Trp Trp Gln Leu Thr Leu Gly Ala Ile Cys
    1025                1030                1035
Ala Leu Pro Leu Ala Gly Leu Leu Ala Cys Cys Ala Lys Cys Leu
    1040                1045                1050
Tyr Tyr Leu Arg Gly Ala Ile Ala Pro Arg
    1055                1060

<210> SEQ ID NO 52
<211> LENGTH: 2116
<212> TYPE: PRT
<213> ORGANISM: Rubella virus

<400> SEQUENCE: 52

Met Glu Lys Leu Leu Asp Glu Val Leu Ala Pro Gly Gly Pro Tyr Asn
1               5                   10                  15
Leu Thr Val Gly Ser Trp Val Arg Asp His Val Arg Ser Ile Val Glu
            20                  25                  30
Gly Ala Trp Glu Val Arg Asp Val Val Thr Ala Ala Gln Lys Arg Ala
        35                  40                  45
Ile Val Ala Val Ile Pro Arg Pro Val Phe Thr Gln Met Gln Val Ser
    50                  55                  60
Asp His Pro Ala Leu His Ala Ile Ser Arg Tyr Thr Arg Arg His Trp
65                  70                  75                  80
Ile Glu Trp Gly Pro Lys Glu Ala Leu His Val Leu Ile Asp Pro Ser
                85                  90                  95
Pro Gly Leu Leu Arg Glu Val Ala Arg Val Glu Arg Arg Trp Val Ala
            100                 105                 110
```

```
Leu Cys Leu His Arg Thr Ala Arg Lys Leu Ala Thr Ala Leu Ala Glu
        115                 120                 125

Thr Ala Ser Glu Ala Trp His Ala Asp Tyr Val Cys Ala Leu Arg Gly
130                 135                 140

Ala Pro Ser Gly Pro Phe Tyr Val His Pro Glu Asp Val Pro His Gly
145                 150                 155                 160

Gly Arg Ala Val Ala Asp Arg Cys Leu Leu Tyr Tyr Thr Pro Met Gln
                165                 170                 175

Met Cys Glu Leu Met Arg Thr Ile Asp Ala Thr Leu Leu Val Ala Val
            180                 185                 190

Asp Leu Trp Pro Val Ala Leu Ala Ala His Val Gly Asp Asp Trp Asp
        195                 200                 205

Asp Leu Gly Ile Ala Trp His Leu Asp His Asp Gly Gly Cys Pro Ala
        210                 215                 220

Asp Cys Arg Gly Ala Gly Ala Gly Pro Thr Pro Gly Tyr Thr Arg Pro
225                 230                 235                 240

Cys Thr Thr Arg Ile Tyr Gln Val Leu Pro Asp Thr Ala His Pro Gly
                245                 250                 255

Arg Leu Tyr Arg Cys Gly Pro Arg Leu Trp Thr Arg Asp Cys Ala Val
            260                 265                 270

Ala Glu Leu Ser Trp Glu Val Ala Gln His Cys Gly His Gln Ala Arg
        275                 280                 285

Val Arg Ala Val Arg Cys Thr Leu Pro Ile Arg His Val Arg Ser Leu
        290                 295                 300

Gln Pro Ser Ala Arg Val Arg Leu Pro Asp Leu Val His Leu Ala Glu
305                 310                 315                 320

Val Gly Arg Trp Arg Trp Phe Ser Leu Pro Arg Pro Val Phe Gln Arg
                325                 330                 335

Met Leu Ser Tyr Cys Lys Thr Leu Ser Pro Asp Ala Tyr Tyr Ser Glu
            340                 345                 350

Arg Val Phe Lys Phe Lys Asn Ala Leu Ser His Ser Ile Thr Leu Ala
        355                 360                 365

Gly Asn Val Leu Gln Glu Gly Trp Lys Gly Thr Cys Ala Glu Glu Asp
        370                 375                 380

Ala Leu Cys Ala Tyr Val Ala Phe Arg Ala Trp Gln Ser Asn Ala Arg
385                 390                 395                 400

Leu Ala Gly Ile Met Lys Ser Ala Lys Arg Cys Ala Ala Asp Ser Leu
                405                 410                 415

Ser Val Ala Gly Trp Leu Asp Thr Ile Trp Asp Ala Ile Lys Arg Phe
            420                 425                 430

Phe Gly Ser Val Pro Leu Ala Glu Arg Met Glu Glu Trp Glu Gln Asp
        435                 440                 445

Ala Ala Val Ala Ala Phe Asp Arg Gly Pro Leu Glu Asp Gly Gly Arg
        450                 455                 460

His Leu Asp Thr Val Gln Pro Gln Ser Pro Pro Arg Pro Glu Ile
465                 470                 475                 480

Ala Ala Thr Trp Ile Val His Ala Ala Ser Ala Asp Arg His Cys Ala
                485                 490                 495

Cys Ala Pro Arg Cys Asp Val Pro Arg Glu Arg Pro Ser Ala Pro Ala
            500                 505                 510

Gly Pro Pro Asp Asp Glu Ala Leu Ile Pro Pro Trp Leu Phe Ala Glu
        515                 520                 525

Arg Arg Ala Leu Arg Cys Arg Glu Trp Asp Phe Glu Ala Leu Arg Ala
```

-continued

```
                530                 535                 540
Arg Ala Asp Thr Ala Ala Ala Pro Ala Pro Leu Ala Pro Arg Pro Ala
545                 550                 555                 560

Arg Tyr Pro Thr Val Leu Tyr Arg His Pro Ala His His Gly Pro Trp
                565                 570                 575

Leu Thr Leu Asp Glu Pro Gly Glu Ala Asp Ala Ala Leu Val Leu Cys
                580                 585                 590

Asp Pro Leu Gly Gln Pro Leu Arg Gly Pro Glu Cys His Phe Ala Ala
                595                 600                 605

Gly Ala His Met Cys Ala Gln Ala Arg Gly Leu Gln Ala Phe Val Arg
                610                 615                 620

Val Val Pro Pro Glu Arg Pro Trp Ala Asp Gly Gly Ala Arg Ala
625                 630                 635                 640

Trp Ala Lys Phe Phe Arg Gly Cys Ala Arg Ala Gln Arg Leu Leu Gly
                645                 650                 655

Glu Pro Ala Val Met His Leu Pro Tyr Thr Asp Gly Asp Val Pro Gln
                660                 665                 670

Leu Ile Ala Leu Ala Leu Arg Thr Leu Ala Gln Gln Gly Ala Ala Leu
                675                 680                 685

Ala Leu Ser Val Arg Asp Leu Pro Gly Gly Ala Ala Phe Asp Ala Asn
                690                 695                 700

Ala Val Thr Ala Ala Val Arg Ala Gly Pro Gly Gln Pro Ala Ala Thr
705                 710                 715                 720

Ser Pro Pro Pro Gly Asp Pro Pro Pro Arg Arg Ala Arg Arg Ser
                725                 730                 735

Gln Arg His Ser Asp Ala Arg Gly Thr Pro Pro Ala Pro Ala Arg
                740                 745                 750

Asp Pro Pro Pro Ala Pro Ser Pro Ala Pro Arg Ala Gly
                755                 760                 765

Asp Pro Val Pro Pro Thr Ser Ala Gly Pro Ala Asp Arg Ala Arg Asp
                770                 775                 780

Ala Glu Leu Glu Val Ala Tyr Glu Pro Ser Gly Pro Pro Thr Ser Thr
785                 790                 795                 800

Lys Ala Asp Pro Asp Ser Asp Ile Val Glu Ser Tyr Ala Arg Ala Ala
                805                 810                 815

Gly Pro Val His Leu Arg Val Arg Asp Ile Met Asp Pro Pro Gly
                820                 825                 830

Cys Lys Val Val Val Asn Ala Ala Asn Glu Gly Leu Leu Ala Gly Ser
                835                 840                 845

Gly Val Cys Gly Ala Ile Phe Ala Asn Ala Thr Ala Ala Leu Ala Ala
850                 855                 860

Asp Cys Arg Arg Leu Ala Pro Cys Pro Thr Gly Glu Ala Val Ala Thr
865                 870                 875                 880

Pro Gly His Gly Cys Gly Tyr Thr His Ile Ile His Ala Val Ala Pro
                885                 890                 895

Arg Arg Pro Arg Asp Pro Ala Ala Leu Glu Glu Gly Glu Ala Leu Leu
                900                 905                 910

Glu Arg Ala Tyr Arg Ser Ile Val Ala Leu Ala Ala Arg Arg Trp
                915                 920                 925

Ala Cys Val Ala Cys Pro Leu Leu Gly Ala Gly Val Tyr Gly Trp Ser
                930                 935                 940

Ala Ala Glu Ser Leu Arg Ala Ala Leu Ala Ala Thr Arg Thr Glu Pro
945                 950                 955                 960
```

```
Ala Glu Arg Val Ser Leu His Ile Cys His Pro Asp Arg Ala Thr Leu
            965                 970                 975

Thr His Ala Ser Val Leu Val Gly Ala Gly Leu Ala Ala Arg Arg Val
            980                 985                 990

Ser Pro Pro Pro Thr Glu Pro Leu  Ala Ser Cys Pro Ala  Gly Asp Pro
            995                1000               1005

Gly Arg  Pro Ala Gln Arg Ser  Ala Ser Pro Pro Ala  Thr Pro Leu
         1010               1015                1020

Gly Asp  Ala Thr Ala Pro Glu  Pro Arg Gly Cys Gln  Gly Cys Glu
         1025               1030                1035

Leu Cys  Arg Cys Thr Arg Val  Thr Asn Asp Arg Ala  Tyr Val Asn
         1040               1045                1050

Leu Trp  Leu Glu Arg Asp Arg  Gly Ala Thr Ser Trp  Ala Met Arg
         1055               1060                1065

Ile Pro  Glu Val Val Val Tyr  Gly Pro Glu His Leu  Ala Thr His
         1070               1075                1080

Phe Pro  Leu Asn His Tyr Ser  Val Leu Lys Pro Ala  Glu Val Arg
         1085               1090                1095

Pro Pro  Arg Gly Met Cys Gly  Ser Asp Met Trp Arg  Cys Arg Gly
         1100               1105                1110

Trp Gln  Gly Met Pro Gln Val  Arg Cys Thr Pro Ser  Asn Ala His
         1115               1120                1125

Ala Ala  Leu Cys Arg Thr Gly  Val Pro Pro Arg Val  Ser Thr Arg
         1130               1135                1140

Gly Gly  Glu Leu Asp Pro Asn  Thr Cys Trp Leu Arg  Ala Ala Ala
         1145               1150                1155

Asn Val  Ala Gln Ala Ala Arg  Ala Cys Gly Ala Tyr  Thr Ser Ala
         1160               1165                1170

Gly Cys  Pro Lys Cys Ala Tyr  Gly Arg Ala Leu Ser  Glu Ala Arg
         1175               1180                1185

Thr Arg  Glu Asp Phe Ala Ala  Leu Ser Gln Arg Trp  Ser Ala Ser
         1190               1195                1200

His Ala  Asp Ala Ser Pro Asp  Gly Thr Gly Asp Pro  Leu Asp Pro
         1205               1210                1215

Leu Met  Glu Thr Val Gly Cys  Ala Cys Ser Arg Val  Trp Val Gly
         1220               1225                1230

Ser Glu  His Glu Ala Pro Pro  Asp His Leu Leu Val  Ser Leu His
         1235               1240                1245

Arg Ala  Pro Asn Gly Pro Trp  Gly Val Val Leu Glu  Val Arg Ala
         1250               1255                1260

Arg Pro  Glu Gly Gly Asn Pro  Thr Gly His Phe Val  Cys Ala Val
         1265               1270                1275

Gly Gly  Gly Pro Arg Arg Val  Ser Asp Arg Pro His  Leu Trp Leu
         1280               1285                1290

Ala Val  Pro Leu Ser Arg Gly  Gly Gly Thr Cys Ala  Ala Thr Asp
         1295               1300                1305

Glu Gly  Leu Ala Gln Ala Tyr  Tyr Asp Asp Leu Glu  Val Arg Arg
         1310               1315                1320

Leu Gly  Asp Asp Ala Met Ala  Arg Ala Ala Leu Ala  Ser Val Gln
         1325               1330                1335

Arg Pro  Arg Lys Gly Pro Tyr  Asn Ile Arg Val Trp  Asn Met Ala
         1340               1345                1350
```

-continued

```
Ala Gly Ala Gly Lys Thr Thr Arg Ile Leu Ala Ala Phe Thr Arg
    1355            1360                1365

Glu Asp Leu Tyr Val Cys Pro Thr Asn Ala Leu Leu His Glu Ile
    1370            1375                1380

Gln Ala Lys Leu Arg Ala Arg Asp Ile Asp Ile Lys Asn Ala Ala
    1385            1390                1395

Thr Tyr Glu Arg Ala Leu Thr Lys Pro Leu Ala Ala Tyr Arg Arg
    1400            1405                1410

Ile Tyr Ile Asp Glu Ala Phe Thr Leu Gly Gly Glu Tyr Cys Ala
    1415            1420                1425

Phe Val Ala Ser Gln Thr Thr Ala Glu Val Ile Cys Val Gly Asp
    1430            1435                1440

Arg Asp Gln Cys Gly Pro His Tyr Ala Asn Asn Cys Arg Thr Pro
    1445            1450                1455

Val Pro Asp Arg Trp Pro Thr Glu Arg Ser Arg His Thr Trp Arg
    1460            1465                1470

Phe Pro Asp Cys Trp Ala Ala Arg Leu Arg Ala Gly Leu Asp Tyr
    1475            1480                1485

Asp Ile Glu Gly Glu Arg Thr Gly Thr Phe Ala Cys Asn Leu Trp
    1490            1495                1500

Asp Gly Arg Gln Val Asp Leu His Leu Ala Phe Ser Arg Glu Thr
    1505            1510                1515

Val Arg Arg Leu His Glu Ala Gly Ile Arg Ala Tyr Thr Val Arg
    1520            1525                1530

Glu Ala Gln Gly Met Ser Val Gly Thr Ala Cys Ile His Val Gly
    1535            1540                1545

Arg Asp Gly Thr Asp Val Ala Leu Ala Leu Thr Arg Asp Leu Ala
    1550            1555                1560

Ile Val Ser Leu Thr Arg Ala Ser Asp Ala Leu Tyr Leu His Glu
    1565            1570                1575

Leu Glu Asp Gly Ser Leu Arg Ala Ala Gly Leu Ser Ala Phe Leu
    1580            1585                1590

Asp Ala Gly Ala Leu Ala Glu Leu Lys Glu Val Pro Ala Gly Ile
    1595            1600                1605

Asp Arg Val Val Ala Val Glu Gln Ala Pro Pro Leu Pro Pro
    1610            1615                1620

Ala Asp Gly Ile Pro Glu Ala Gln Asp Val Pro Pro Phe Cys Pro
    1625            1630                1635

Arg Thr Leu Glu Glu Leu Val Phe Gly Arg Ala Gly His Pro His
    1640            1645                1650

Tyr Ala Asp Leu Asn Arg Val Thr Glu Gly Glu Arg Glu Val Arg
    1655            1660                1665

Tyr Met Arg Ile Ser Arg His Leu Leu Asn Lys Asn His Thr Glu
    1670            1675                1680

Met Pro Gly Thr Glu Arg Val Leu Ser Ala Val Cys Ala Val Arg
    1685            1690                1695

Arg Tyr Arg Ala Gly Glu Asp Gly Ser Thr Leu Arg Thr Ala Val
    1700            1705                1710

Ala Arg Gln His Pro Arg Pro Phe Arg Gln Ile Pro Pro Pro Arg
    1715            1720                1725

Val Thr Ala Gly Val Ala Gln Glu Trp Arg Met Thr Tyr Leu Arg
    1730            1735                1740

Glu Arg Ile Asp Leu Thr Asp Val Tyr Thr Gln Met Gly Val Ala
```

```
               1745                1750                1755

Ala Arg Glu Leu Thr Asp Arg Tyr Ala Arg Arg Tyr Pro Glu Ile
           1760                1765                1770

Phe Ala Gly Met Cys Thr Ala Gln Ser Leu Ser Val Pro Ala Phe
           1775                1780                1785

Leu Lys Ala Thr Leu Lys Cys Val Asp Ala Ala Leu Gly Pro Arg
           1790                1795                1800

Asp Thr Glu Asp Cys His Ala Ala Gln Gly Lys Ala Gly Leu Glu
           1805                1810                1815

Ile Arg Ala Trp Ala Lys Glu Trp Val Gln Val Met Ser Pro His
           1820                1825                1830

Phe Arg Ala Ile Gln Lys Ile Ile Met Arg Ala Leu Arg Pro Gln
           1835                1840                1845

Phe Leu Val Ala Ala Gly His Thr Glu Pro Glu Val Asp Ala Trp
           1850                1855                1860

Trp Gln Ala His Tyr Thr Thr Asn Ala Ile Glu Val Asp Phe Thr
           1865                1870                1875

Glu Phe Asp Met Asn Gln Thr Leu Ala Thr Arg Asp Val Glu Leu
           1880                1885                1890

Glu Ile Ser Ala Ala Leu Leu Gly Leu Pro Cys Ala Glu Asp Tyr
           1895                1900                1905

Arg Ala Leu Arg Ala Gly Ser Tyr Cys Thr Leu Arg Glu Leu Gly
           1910                1915                1920

Ser Thr Glu Thr Gly Cys Glu Arg Thr Ser Gly Glu Pro Ala Thr
           1925                1930                1935

Leu Leu His Asn Thr Thr Val Ala Met Cys Met Ala Met Arg Met
           1940                1945                1950

Val Pro Lys Gly Val Arg Trp Ala Gly Ile Phe Gln Gly Asp Asp
           1955                1960                1965

Met Val Ile Phe Leu Pro Glu Gly Ala Arg Ser Ala Ala Leu Lys
           1970                1975                1980

Trp Thr Pro Ala Glu Val Gly Leu Phe Gly Phe His Ile Pro Val
           1985                1990                1995

Lys His Val Ser Thr Pro Thr Pro Ser Phe Cys Gly His Val Gly
           2000                2005                2010

Thr Ala Ala Gly Leu Phe His Asp Val Met His Gln Ala Ile Lys
           2015                2020                2025

Val Leu Cys Arg Arg Phe Asp Pro Asp Val Leu Glu Glu Gln Gln
           2030                2035                2040

Val Ala Leu Leu Asp Arg Leu Arg Gly Val Tyr Ala Ala Leu Pro
           2045                2050                2055

Asp Thr Val Ala Ala Asn Ala Ala Tyr Tyr Asp Tyr Ser Ala Glu
           2060                2065                2070

Arg Val Leu Ala Ile Val Arg Glu Leu Thr Ala Tyr Ala Arg Gly
           2075                2080                2085

Arg Gly Leu Asp His Pro Ala Thr Ile Gly Ala Leu Glu Glu Ile
           2090                2095                2100

Gln Thr Pro Tyr Ala Arg Ala Asn Leu His Asp Ala Asp
           2105                2110                2115

<210> SEQ ID NO 53
<211> LENGTH: 617
<212> TYPE: PRT
<213> ORGANISM: Measles virus
```

<400> SEQUENCE: 53

```
Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
```

-continued

```
                405                 410                 415
Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
            435                 440                 445

Asn Asn Val Tyr Trp Leu Thr Ile Pro Pro Met Lys Asn Leu Ala Leu
            450                 455                 460

Gly Val Ile Asn Thr Leu Glu Trp Ile Pro Arg Phe Lys Val Ser Pro
465                 470                 475                 480

Tyr Leu Phe Asn Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
            515                 520                 525

Tyr Asp Thr Ser Arg Val Glu His Ala Val Val Tyr Tyr Val Tyr Ser
            530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Glu Gly Met Gly Val Ser Cys Thr Val
            595                 600                 605

Thr Arg Glu Asp Gly Thr Asn Arg Arg
            610                 615

<210> SEQ ID NO 54
<211> LENGTH: 299
<212> TYPE: PRT
<213> ORGANISM: Measles virus

<400> SEQUENCE: 54

Met Ala Glu Glu Gln Ala Arg His Val Lys Asn Gly Leu Glu Cys Ile
1               5                   10                  15

Arg Ala Leu Lys Ala Glu Pro Ile Gly Ser Leu Ala Ile Glu Glu Ala
            20                  25                  30

Met Ala Ala Trp Ser Glu Ile Ser Asp Asn Pro Gly Gln Glu Arg Ala
        35                  40                  45

Thr Cys Arg Glu Glu Lys Ala Gly Ser Ser Gly Leu Ser Lys Pro Cys
50                  55                  60

Leu Ser Ala Ile Gly Ser Thr Glu Gly Gly Ala Pro Arg Ile Arg Gly
65                  70                  75                  80

Gln Gly Pro Gly Glu Ser Asp Asp Ala Glu Thr Leu Gly Ile Pro
                85                  90                  95

Pro Arg Asn Leu Gln Ala Ser Ser Thr Gly Leu Gln Cys Tyr Tyr Val
            100                 105                 110

Tyr Asp His Ser Gly Glu Ala Val Lys Gly Ile Gln Asp Ala Asp Ser
            115                 120                 125

Ile Met Val Gln Ser Gly Leu Asp Gly Asp Ser Thr Leu Ser Gly Gly
        130                 135                 140

Asp Asn Glu Ser Glu Asn Ser Asp Val Asp Ile Gly Glu Pro Asp Thr
145                 150                 155                 160
```

```
Glu Gly Tyr Ala Ile Thr Asp Arg Gly Ser Ala Pro Ile Ser Met Gly
                165                 170                 175

Phe Arg Ala Ser Asp Val Glu Thr Ala Glu Gly Gly Glu Ile His Glu
            180                 185                 190

Leu Leu Arg Leu Gln Ser Arg Gly Asn Asn Phe Pro Lys Leu Gly Lys
        195                 200                 205

Thr Leu Asn Val Pro Pro Pro Asp Pro Gly Arg Ala Ser Thr Ser
    210                 215                 220

Glu Thr Pro Ile Lys Lys Gly His Arg Arg Glu Ile Ser Leu Ile Trp
225                 230                 235                 240

Asn Gly Asp Arg Val Phe Ile Asp Arg Trp Cys Asn Pro Met Cys Ser
                245                 250                 255

Lys Val Thr Leu Gly Thr Ile Arg Ala Arg Cys Thr Cys Gly Glu Cys
            260                 265                 270

Pro Arg Val Cys Glu Gln Cys Arg Thr Asp Thr Gly Val Asp Thr Arg
        275                 280                 285

Ile Trp Tyr His Asn Leu Pro Glu Ile Pro Glu
    290                 295

<210> SEQ ID NO 55
<211> LENGTH: 335
<212> TYPE: PRT
<213> ORGANISM: Measles virus

<400> SEQUENCE: 55

Met Thr Glu Ile Tyr Asp Phe Asp Lys Ser Ala Trp Asp Ile Lys Gly
1               5                   10                  15

Ser Ile Ala Pro Ile Gln Pro Thr Thr Tyr Ser Asp Gly Arg Leu Val
                20                  25                  30

Pro Gln Val Arg Val Ile Asp Pro Gly Leu Gly Asp Arg Lys Asp Glu
            35                  40                  45

Cys Phe Met Tyr Met Phe Leu Leu Gly Val Val Glu Asp Ser Asp Pro
        50                  55                  60

Leu Gly Pro Pro Ile Gly Arg Ala Phe Gly Ser Leu Pro Leu Gly Val
65                  70                  75                  80

Gly Arg Ser Thr Ala Lys Pro Glu Glu Leu Leu Lys Glu Ala Thr Glu
                85                  90                  95

Leu Asp Ile Val Val Arg Arg Thr Ala Gly Leu Asn Glu Lys Leu Val
            100                 105                 110

Phe Tyr Asn Asn Thr Pro Leu Thr Leu Leu Thr Pro Trp Arg Lys Val
        115                 120                 125

Leu Thr Thr Gly Ser Val Phe Asn Ala Asn Gln Val Cys Asn Ala Val
130                 135                 140

Asn Leu Ile Pro Leu Asp Thr Pro Gln Arg Phe Arg Val Val Tyr Met
145                 150                 155                 160

Ser Ile Thr Arg Leu Ser Asp Asn Gly Tyr Tyr Thr Val Pro Arg Arg
                165                 170                 175

Met Leu Glu Phe Arg Ser Val Asn Ala Val Ala Phe Asn Leu Leu Val
            180                 185                 190

Thr Leu Arg Ile Asp Lys Ala Ile Gly Pro Gly Lys Ile Ile Asp Asn
        195                 200                 205

Ala Glu Gln Leu Pro Glu Ala Thr Phe Met Val His Ile Gly Asn Phe
    210                 215                 220

Arg Arg Lys Lys Ser Glu Val Tyr Ser Ala Asp Tyr Cys Lys Met Lys
225                 230                 235                 240
```

```
Ile Glu Lys Met Gly Leu Val Phe Ala Leu Gly Gly Ile Gly Gly Thr
                245                 250                 255

Ser Leu His Ile Arg Ser Thr Gly Lys Met Ser Lys Thr Leu His Ala
            260                 265                 270

Gln Leu Gly Phe Lys Lys Thr Leu Cys Tyr Pro Leu Met Asp Ile Asn
        275                 280                 285

Glu Asp Leu Asn Arg Leu Leu Trp Arg Ser Arg Cys Lys Ile Val Arg
    290                 295                 300

Ile Gln Ala Val Leu Gln Pro Ser Val Pro Gln Glu Phe Arg Ile Tyr
305                 310                 315                 320

Asp Asp Val Ile Ile Asn Asp Asp Gln Gly Leu Phe Lys Val Leu
                325                 330                 335

<210> SEQ ID NO 56
<211> LENGTH: 186
<212> TYPE: PRT
<213> ORGANISM: Measles virus

<400> SEQUENCE: 56

Met Ser Lys Thr Asp Trp Asn Ala Ser Gly Leu Ser Arg Pro Ser Pro
1               5                   10                  15

Ser Ala His Trp Pro Ser Arg Lys Leu Trp Gln His Gly Gln Lys Tyr
            20                  25                  30

Gln Thr Thr Gln Asp Arg Ser Glu Pro Pro Ala Gly Lys Arg Arg Gln
        35                  40                  45

Ala Val Arg Val Ser Ala Asn His Ala Ser Gln Gln Leu Asp Gln Leu
    50                  55                  60

Lys Ala Val His Leu Ala Ser Ala Val Arg Asp Leu Glu Arg Ala Met
65                  70                  75                  80

Thr Thr Leu Lys Leu Trp Glu Ser Pro Gln Glu Ile Ser Arg His Gln
                85                  90                  95

Ala Leu Gly Tyr Ser Val Ile Met Phe Met Ile Thr Ala Val Lys Arg
            100                 105                 110

Leu Arg Glu Ser Lys Met Leu Thr Leu Ser Trp Phe Asn Gln Ala Leu
        115                 120                 125

Met Val Ile Ala Pro Tyr Gln Glu Glu Thr Met Asn Leu Lys Thr Ala
    130                 135                 140

Met Trp Ile Leu Ala Asn Leu Ile Pro Arg Asp Met Leu Ser Leu Thr
145                 150                 155                 160

Gly Asp Leu Leu Pro Ser Leu Trp Gly Ser Gly Leu Leu Met Leu Lys
                165                 170                 175

Leu Gln Lys Glu Gly Arg Ser Thr Ser Ser
            180                 185

<210> SEQ ID NO 57
<211> LENGTH: 226
<212> TYPE: PRT
<213> ORGANISM: Hepatitis B virus

<400> SEQUENCE: 57

Met Glu Asn Thr Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ala His Thr Cys
        35                  40                  45
```

```
Pro Gly Gln Asn Ser Gln Ser Pro Ser Ser Asn His Ser Pro Thr Ser
    50                  55                  60

Cys Pro Pro Ile Cys Pro Gly Tyr Arg Trp Met Tyr Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Leu Pro Gly
            100                 105                 110

Thr Ser Thr Thr Ser Thr Gly Pro Cys Lys Thr Cys Thr Ile Pro Ala
            115                 120                 125

Gln Gly Thr Ser Met Phe Pro Ser Cys Cys Cys Thr Lys Pro Ser Asp
    130                 135                 140

Gly Asn Cys Thr Cys Ile Pro Ile Pro Ser Ser Trp Ala Phe Ala Arg
145                 150                 155                 160

Phe Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Asn Ile
        195                 200                 205

Leu Ser Pro Phe Leu Pro Leu Leu Pro Ile Phe Phe Cys Leu Trp Val
    210                 215                 220

Tyr Val
225

<210> SEQ ID NO 58
<211> LENGTH: 183
<212> TYPE: PRT
<213> ORGANISM: Hepatitis B virus

<400> SEQUENCE: 58

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
```

180

<210> SEQ ID NO 59
<211> LENGTH: 382
<212> TYPE: PRT
<213> ORGANISM: Homo sapiens

<400> SEQUENCE: 59

```
Met Gly Leu Leu Leu Pro Leu Ala Leu Cys Ile Leu Val Leu Cys Cys
1               5                   10                  15

Gly Ala Met Ser Pro Pro Gln Leu Ala Leu Asn Pro Ser Ala Leu Leu
            20                  25                  30

Ser Arg Gly Cys Asn Asp Ser Asp Val Leu Ala Val Ala Gly Phe Ala
        35                  40                  45

Leu Arg Asp Ile Asn Lys Asp Arg Lys Asp Gly Tyr Val Leu Arg Leu
    50                  55                  60

Asn Arg Val Asn Asp Ala Gln Glu Tyr Arg Arg Gly Leu Gly Gly Ser
65                  70                  75                  80

Leu Phe Tyr Leu Thr Leu Asp Val Leu Glu Thr Asp Cys His Val Leu
                85                  90                  95

Arg Lys Lys Ala Trp Gln Asp Cys Gly Met Arg Ile Phe Phe Glu Ser
            100                 105                 110

Val Tyr Gly Gln Cys Lys Ala Ile Phe Tyr Met Asn Asn Pro Ser Arg
        115                 120                 125

Val Leu Tyr Leu Ala Ala Tyr Asn Cys Thr Leu Arg Pro Val Ser Lys
    130                 135                 140

Lys Lys Ile Tyr Met Thr Cys Pro Asp Cys Pro Ser Ser Ile Pro Thr
145                 150                 155                 160

Asp Ser Ser Asn His Gln Val Leu Glu Ala Ala Thr Glu Ser Leu Ala
                165                 170                 175

Lys Tyr Asn Asn Glu Asn Thr Ser Lys Gln Tyr Ser Leu Phe Lys Val
            180                 185                 190

Thr Arg Ala Ser Ser Gln Trp Val Val Gly Pro Ser Tyr Phe Val Glu
        195                 200                 205

Tyr Leu Ile Lys Glu Ser Pro Cys Thr Lys Ser Gln Ala Ser Ser Cys
    210                 215                 220

Ser Leu Gln Ser Ser Asp Ser Val Pro Val Gly Leu Cys Lys Gly Ser
225                 230                 235                 240

Leu Thr Arg Thr His Trp Glu Lys Phe Val Ser Val Thr Cys Asp Phe
                245                 250                 255

Phe Glu Ser Gln Ala Pro Ala Thr Gly Ser Glu Asn Ser Ala Val Asn
            260                 265                 270

Gln Lys Pro Thr Asn Leu Pro Lys Val Glu Glu Ser Gln Gln Lys Asn
        275                 280                 285

Thr Pro Pro Thr Asp Ser Pro Ser Lys Ala Gly Pro Arg Gly Ser Val
    290                 295                 300

Gln Tyr Leu Pro Asp Leu Asp Asp Lys Asn Ser Gln Glu Lys Gly Pro
305                 310                 315                 320

Gln Glu Ala Phe Pro Val His Leu Asp Leu Thr Thr Asn Pro Gln Gly
                325                 330                 335

Glu Thr Leu Asp Ile Ser Phe Leu Phe Leu Glu Pro Met Glu Glu Lys
            340                 345                 350

Leu Val Val Leu Pro Phe Pro Lys Glu Lys Ala Arg Thr Ala Glu Cys
        355                 360                 365
```

```
Pro Gly Pro Ala Gln Asn Ala Ser Pro Leu Val Leu Pro Pro
        370                 375                 380

<210> SEQ ID NO 60
<211> LENGTH: 561
<212> TYPE: PRT
<213> ORGANISM: Cytomegalovirus

<400> SEQUENCE: 60

Met Glu Ser Arg Gly Arg Cys Pro Glu Met Ile Ser Val Leu Gly
1               5                   10                  15

Pro Ile Ser Gly His Val Leu Lys Ala Val Phe Ser Arg Gly Asp Thr
            20                  25                  30

Pro Val Leu Pro His Glu Thr Arg Leu Leu Gln Thr Gly Ile His Val
        35                  40                  45

Arg Val Ser Gln Pro Ser Leu Ile Leu Val Ser Gln Tyr Thr Pro Asp
    50                  55                  60

Ser Thr Pro Cys His Arg Gly Asp Asn Gln Leu Gln Val Gln His Thr
65                  70                  75                  80

Tyr Phe Thr Gly Ser Glu Val Glu Asn Val Ser Val Asn Val His Asn
                85                  90                  95

Pro Thr Gly Arg Ser Ile Cys Pro Ser Gln Glu Pro Met Ser Ile Tyr
            100                 105                 110

Val Tyr Ala Leu Pro Leu Lys Met Leu Asn Ile Pro Ser Ile Asn Val
        115                 120                 125

His His Tyr Pro Ser Ala Ala Glu Arg Lys His Arg His Leu Pro Val
    130                 135                 140

Ala Asp Ala Val Ile His Ala Ser Gly Lys Gln Met Trp Gln Ala Arg
145                 150                 155                 160

Leu Thr Val Ser Gly Leu Ala Trp Thr Arg Gln Gln Asn Gln Trp Lys
                165                 170                 175

Glu Pro Asp Val Tyr Tyr Thr Ser Ala Phe Val Phe Pro Thr Lys Asp
            180                 185                 190

Val Ala Leu Arg His Val Val Cys Ala His Glu Leu Val Cys Ser Met
        195                 200                 205

Glu Asn Thr Arg Ala Thr Lys Met Gln Val Ile Gly Asp Gln Tyr Val
    210                 215                 220

Lys Val Tyr Leu Glu Ser Phe Cys Glu Asp Val Pro Ser Gly Lys Leu
225                 230                 235                 240

Phe Met His Val Thr Leu Gly Ser Asp Val Glu Glu Asp Leu Thr Met
                245                 250                 255

Thr Arg Asn Pro Gln Pro Phe Met Arg Pro His Glu Arg Asn Gly Phe
            260                 265                 270

Thr Val Leu Cys Pro Lys Asn Met Ile Ile Lys Pro Gly Lys Ile Ser
        275                 280                 285

His Ile Met Leu Asp Val Ala Phe Thr Ser His Glu His Phe Gly Leu
    290                 295                 300

Leu Cys Pro Lys Ser Ile Pro Gly Leu Ser Ile Ser Gly Asn Leu Leu
305                 310                 315                 320

Met Asn Gly Gln Gln Ile Phe Leu Glu Val Gln Ala Ile Arg Glu Thr
                325                 330                 335

Val Glu Leu Arg Gln Tyr Asp Pro Val Ala Ala Leu Phe Phe Phe Asp
            340                 345                 350

Ile Asp Leu Leu Leu Gln Arg Gly Pro Gln Tyr Ser Glu His Pro Thr
        355                 360                 365
```

-continued

```
Phe Thr Ser Gln Tyr Arg Ile Gln Gly Lys Leu Glu Tyr Arg His Thr
    370                 375                 380

Trp Asp Arg His Asp Glu Gly Ala Ala Gln Gly Asp Asp Asp Val Trp
385                 390                 395                 400

Thr Ser Gly Ser Asp Ser Asp Glu Glu Leu Val Thr Thr Glu Arg Lys
                405                 410                 415

Thr Pro Arg Val Thr Gly Gly Ala Met Ala Gly Ala Ser Thr Ser Ser
                420                 425                 430

Ala Gly Arg Lys Arg Lys Ser Ala Ser Ser Ala Thr Ala Cys Thr Ser
                435                 440                 445

Gly Val Met Thr Arg Gly Arg Leu Lys Ala Glu Ser Thr Val Ala Pro
            450                 455                 460

Glu Glu Asp Thr Asp Glu Asp Ser Asp Asn Glu Ile His Asn Pro Ala
465                 470                 475                 480

Val Phe Thr Trp Pro Pro Trp Gln Ala Gly Ile Leu Ala Arg Asn Leu
                485                 490                 495

Val Pro Met Val Ala Thr Val Gln Gly Gln Asn Leu Lys Tyr Gln Glu
                500                 505                 510

Phe Phe Trp Asp Ala Asn Asp Ile Tyr Arg Ile Phe Ala Glu Leu Glu
            515                 520                 525

Gly Val Trp Gln Pro Ala Ala Gln Pro Lys Arg Arg Arg His Arg Gln
            530                 535                 540

Asp Ala Leu Pro Gly Pro Cys Ile Ala Ser Thr Pro Lys Lys His Arg
545                 550                 555                 560

Gly

<210> SEQ ID NO 61
<211> LENGTH: 356
<212> TYPE: PRT
<213> ORGANISM: Homo sapiens

<400> SEQUENCE: 61

Met Leu Ala Arg Ala Ala Arg Gly Thr Gly Ala Leu Leu Leu Arg Gly
1               5                   10                  15

Ser Leu Leu Ala Ser Gly Arg Ala Pro Arg Arg Ala Ser Ser Gly Leu
                20                  25                  30

Pro Arg Asn Thr Val Val Leu Phe Val Pro Gln Gln Glu Ala Trp Val
            35                  40                  45

Val Glu Arg Met Gly Arg Phe His Arg Ile Leu Glu Pro Gly Leu Asn
50                  55                  60

Ile Leu Ile Pro Val Leu Asp Arg Ile Arg Tyr Val Gln Ser Leu Lys
65                  70                  75                  80

Glu Ile Val Ile Asn Val Pro Glu Gln Ser Ala Val Thr Leu Asp Asn
                85                  90                  95

Val Thr Leu Gln Ile Asp Gly Val Leu Tyr Leu Arg Ile Met Asp Pro
            100                 105                 110

Tyr Lys Ala Ser Tyr Gly Val Glu Asp Pro Glu Tyr Ala Val Thr Gln
        115                 120                 125

Leu Ala Gln Thr Thr Met Arg Ser Glu Leu Gly Lys Leu Ser Leu Asp
    130                 135                 140

Lys Val Phe Arg Glu Arg Glu Ser Leu Asn Ala Ser Ile Val Asp Ala
145                 150                 155                 160

Ile Asn Gln Ala Ala Asp Cys Trp Gly Ile Arg Cys Leu Arg Tyr Glu
                165                 170                 175
```

```
Ile Lys Asp Ile His Val Pro Pro Arg Val Lys Glu Ser Met Gln Met
            180                 185                 190

Gln Val Glu Ala Glu Arg Arg Lys Arg Ala Thr Val Leu Glu Ser Glu
            195                 200                 205

Gly Thr Arg Glu Ser Ala Ile Asn Val Ala Glu Gly Lys Lys Gln Ala
            210                 215                 220

Gln Ile Leu Ala Ser Glu Ala Glu Lys Ala Glu Gln Ile Asn Gln Ala
225                 230                 235                 240

Ala Gly Glu Ala Ser Ala Val Leu Ala Lys Ala Lys Ala Lys Ala Glu
            245                 250                 255

Ala Ile Arg Ile Leu Ala Ala Ala Leu Thr Gln His Asn Gly Asp Ala
            260                 265                 270

Ala Ala Ser Leu Thr Val Ala Glu Gln Tyr Val Ser Ala Phe Ser Lys
            275                 280                 285

Leu Ala Lys Asp Ser Asn Thr Ile Leu Leu Pro Ser Asn Pro Gly Asp
            290                 295                 300

Val Thr Ser Met Val Ala Gln Ala Met Gly Val Tyr Gly Ala Leu Thr
305                 310                 315                 320

Lys Ala Pro Val Pro Gly Thr Pro Asp Ser Leu Ser Gly Ser Ser
            325                 330                 335

Arg Asp Val Gln Gly Thr Asp Ala Ser Leu Asp Glu Glu Leu Asp Arg
            340                 345                 350

Val Lys Met Ser
            355

<210> SEQ ID NO 62
<211> LENGTH: 1147
<212> TYPE: PRT
<213> ORGANISM: Helicobacter pylori

<400> SEQUENCE: 62

Met Thr Asn Glu Thr Ile Asp Gln Gln Pro Gln Thr Glu Ala Ala Phe
1               5                   10                  15

Asn Pro Gln Gln Phe Ile Asn Asn Leu Gln Val Ala Phe Leu Lys Val
            20                  25                  30

Asp Asn Ala Val Ala Ser Tyr Asp Pro Asp Gln Lys Pro Ile Val Asp
            35                  40                  45

Lys Asn Asp Arg Asp Asn Arg Gln Ala Phe Glu Gly Ile Ser Gln Leu
        50                  55                  60

Arg Glu Glu Tyr Ser Asn Lys Ala Ile Lys Asn Pro Thr Lys Lys Asn
65                  70                  75                  80

Gln Tyr Phe Ser Asp Phe Ile Asn Lys Ser Asn Asp Leu Ile Asn Lys
            85                  90                  95

Asp Asn Leu Ile Asp Val Glu Ser Ser Thr Lys Ser Phe Gln Lys Phe
            100                 105                 110

Gly Asp Gln Arg Tyr Arg Ile Phe Thr Ser Trp Val Ser His Gln Asn
            115                 120                 125

Asp Pro Ser Lys Ile Asn Thr Arg Ser Ile Arg Asn Phe Met Glu Asn
            130                 135                 140

Ile Ile Gln Pro Pro Ile Leu Asp Asp Lys Glu Lys Ala Glu Phe Leu
145                 150                 155                 160

Lys Ser Ala Lys Gln Ser Phe Ala Gly Ile Ile Ile Gly Asn Gln Ile
            165                 170                 175

Arg Thr Asp Gln Lys Phe Met Gly Val Phe Asp Glu Ser Leu Lys Glu
```

```
                180                 185                 190
Arg Gln Glu Ala Glu Lys Asn Gly Glu Pro Thr Gly Gly Asp Trp Leu
                195                 200                 205

Asp Ile Phe Leu Ser Phe Ile Phe Asp Lys Lys Gln Ser Ser Asp Val
            210                 215                 220

Lys Glu Ala Ile Asn Gln Glu Pro Val Pro His Val Gln Pro Asp Ile
225                 230                 235                 240

Ala Thr Thr Thr Thr Asp Ile Gln Gly Leu Pro Pro Glu Ala Arg Asp
                245                 250                 255

Leu Leu Asp Glu Arg Gly Asn Phe Ser Lys Phe Thr Leu Gly Asp Met
            260                 265                 270

Glu Met Leu Asp Val Glu Gly Val Ala Asp Ile Asp Pro Asn Tyr Lys
        275                 280                 285

Phe Asn Gln Leu Leu Ile His Asn Asn Ala Leu Ser Ser Val Leu Met
    290                 295                 300

Gly Ser His Asn Gly Ile Glu Pro Glu Lys Val Ser Leu Leu Tyr Gly
305                 310                 315                 320

Gly Asn Gly Gly Pro Gly Ala Arg His Asp Trp Asn Ala Thr Val Gly
                325                 330                 335

Tyr Lys Asp Gln Gln Gly Asn Asn Val Ala Thr Ile Ile Asn Val His
            340                 345                 350

Met Lys Asn Gly Ser Gly Leu Val Ile Ala Gly Gly Glu Lys Gly Ile
        355                 360                 365

Asn Asn Pro Ser Phe Tyr Leu Tyr Lys Glu Asp Gln Leu Thr Gly Ser
    370                 375                 380

Gln Arg Ala Leu Ser Gln Glu Ile Gln Asn Lys Ile Asp Phe Met
385                 390                 395                 400

Glu Phe Leu Ala Gln Asn Asn Ala Lys Leu Asp Asn Leu Ser Glu Lys
                405                 410                 415

Glu Lys Glu Lys Phe Arg Thr Glu Ile Lys Asp Phe Gln Lys Asp Ser
            420                 425                 430

Lys Ala Tyr Leu Asp Ala Leu Gly Asn Asp Arg Ile Ala Phe Val Ser
        435                 440                 445

Lys Lys Asp Thr Lys His Ser Ala Leu Ile Thr Glu Phe Gly Asn Gly
    450                 455                 460

Asp Leu Ser Tyr Thr Leu Lys Asp Tyr Gly Lys Lys Ala Asp Lys Ala
465                 470                 475                 480

Leu Asp Arg Glu Lys Asn Val Thr Leu Gln Gly Ser Leu Lys His Asp
                485                 490                 495

Gly Val Met Phe Val Asp Tyr Ser Asn Phe Lys Tyr Thr Asn Ala Ser
            500                 505                 510

Lys Asn Pro Asn Lys Gly Val Gly Val Thr Asn Gly Val Ser His Leu
        515                 520                 525

Glu Val Gly Phe Asn Lys Val Ala Ile Phe Asn Leu Pro Asp Leu Asn
    530                 535                 540

Asn Leu Ala Ile Thr Ser Phe Val Arg Arg Asn Leu Glu Asp Lys Leu
545                 550                 555                 560

Thr Thr Lys Gly Leu Ser Pro Gln Glu Ala Asn Lys Leu Ile Lys Asp
                565                 570                 575

Phe Leu Ser Ser Asn Lys Glu Leu Val Gly Lys Thr Leu Asn Phe Asn
            580                 585                 590

Lys Ala Val Ala Asp Ala Lys Asn Thr Gly Asn Tyr Asp Glu Val Lys
        595                 600                 605
```

```
Lys Ala Gln Lys Asp Leu Glu Lys Ser Leu Arg Lys Arg Glu His Leu
    610                 615                 620
Glu Lys Glu Val Glu Lys Leu Glu Ser Lys Ser Gly Asn Lys Asn
625                 630                 635                 640
Lys Met Glu Ala Lys Ala Gln Ala Asn Ser Gln Lys Asp Glu Ile Phe
                645                 650                 655
Ala Leu Ile Asn Lys Glu Ala Asn Arg Asp Ala Arg Ala Ile Ala Tyr
            660                 665                 670
Ala Gln Asn Leu Lys Gly Ile Lys Arg Glu Leu Ser Asp Lys Leu Glu
            675                 680                 685
Asn Val Asn Lys Asn Leu Lys Asp Phe Asp Lys Ser Phe Asp Glu Phe
    690                 695                 700
Lys Asn Gly Lys Asn Lys Asp Phe Ser Lys Ala Glu Glu Thr Leu Lys
705                 710                 715                 720
Ala Leu Lys Gly Ser Val Lys Asp Leu Gly Ile Asn Pro Glu Trp Ile
                725                 730                 735
Ser Lys Val Glu Asn Leu Asn Ala Ala Leu Asn Glu Phe Lys Asn Gly
            740                 745                 750
Lys Asn Lys Asp Phe Ser Lys Val Thr Gln Ala Lys Ser Asp Leu Glu
    755                 760                 765
Asn Ser Val Lys Asp Val Ile Ile Asn Gln Lys Val Thr Asp Lys Val
770                 775                 780
Asp Asn Leu Asn Gln Ala Val Ser Val Ala Lys Ala Thr Gly Asp Phe
785                 790                 795                 800
Ser Arg Val Glu Gln Ala Leu Ala Asp Leu Lys Asn Phe Ser Lys Glu
                805                 810                 815
Gln Leu Ala Gln Gln Ala Gln Lys Asn Glu Ser Leu Asn Ala Arg Lys
            820                 825                 830
Lys Ser Glu Ile Tyr Gln Ser Val Lys Asn Gly Val Asn Gly Thr Leu
            835                 840                 845
Val Gly Asn Gly Leu Ser Gln Ala Glu Ala Thr Thr Leu Ser Lys Asn
    850                 855                 860
Phe Ser Asp Ile Lys Lys Glu Leu Asn Ala Lys Leu Gly Asn Phe Asn
865                 870                 875                 880
Asn Asn Asn Asn Asn Gly Leu Lys Asn Glu Pro Ile Tyr Ala Lys Val
                885                 890                 895
Asn Lys Lys Lys Ala Gly Gln Ala Ala Ser Leu Glu Glu Pro Ile Tyr
            900                 905                 910
Ala Gln Val Ala Lys Lys Val Asn Ala Lys Ile Asp Arg Leu Asn Gln
            915                 920                 925
Ile Ala Ser Gly Leu Gly Val Val Gly Gln Ala Ala Gly Phe Pro Leu
    930                 935                 940
Lys Arg His Asp Lys Val Asp Asp Leu Ser Lys Val Gly Leu Ser Arg
945                 950                 955                 960
Asn Gln Glu Leu Ala Gln Lys Ile Asp Asn Leu Asn Gln Ala Val Ser
                965                 970                 975
Glu Ala Lys Ala Gly Phe Phe Gly Asn Leu Glu Gln Thr Ile Asp Lys
            980                 985                 990
Leu Lys Asp Ser Thr Lys His Asn Pro Met Asn Leu Trp Val Glu Ser
            995                 1000                1005
Ala Lys Lys Val Pro Ala Ser Leu Ser Ala Lys Leu Asp Asn Tyr
    1010                1015                1020
```

-continued

Ala Thr Asn Ser His Ile Arg Ile Asn Ser Asn Ile Lys Asn Gly
    1025                1030                1035

Ala Ile Asn Glu Lys Ala Thr Gly Met Leu Thr Gln Lys Asn Pro
    1040                1045                1050

Glu Trp Leu Lys Leu Val Asn Asp Lys Ile Val Ala His Asn Val
    1055                1060                1065

Gly Ser Val Pro Leu Ser Glu Tyr Asp Lys Ile Gly Phe Asn Gln
    1070                1075                1080

Lys Asn Met Lys Asp Tyr Ser Asp Ser Phe Lys Phe Ser Thr Lys
    1085                1090                1095

Leu Asn Asn Ala Val Lys Asp Thr Asn Ser Gly Phe Thr Gln Phe
    1100                1105                1110

Leu Thr Asn Ala Phe Ser Thr Ala Ser Tyr Tyr Cys Leu Ala Arg
    1115                1120                1125

Glu Asn Ala Glu His Gly Ile Lys Asn Val Asn Thr Lys Gly Gly
    1130                1135                1140

Phe Gln Lys Ser
    1145

<210> SEQ ID NO 63
<211> LENGTH: 1287
<212> TYPE: PRT
<213> ORGANISM: Helicobacter pylori

<400> SEQUENCE: 63

Met Glu Ile Gln Gln Thr His Arg Lys Ile Asn Arg Pro Leu Val Ser
1               5                   10                  15

Leu Ala Leu Val Gly Ala Leu Val Ser Ile Thr Pro Gln Gln Ser His
                20                  25                  30

Ala Ala Phe Phe Thr Thr Val Ile Pro Ala Ile Val Gly Gly Ile
                35                  40                  45

Ala Thr Gly Thr Ala Val Gly Thr Val Ser Gly Leu Leu Gly Trp Gly
        50                  55                  60

Leu Lys Gln Ala Glu Glu Ala Asn Lys Thr Pro Asp Lys Pro Asp Lys
65                  70                  75                  80

Val Trp Arg Ile Gln Ala Gly Lys Gly Phe Asn Glu Phe Pro Asn Lys
                85                  90                  95

Glu Tyr Asp Leu Tyr Lys Ser Leu Leu Ser Ser Lys Ile Asp Gly Gly
                100                 105                 110

Trp Asp Trp Gly Asn Ala Ala Thr His Tyr Trp Ile Lys Gly Gly Gln
            115                 120                 125

Trp Asn Lys Leu Glu Val Asp Met Lys Asp Ala Val Gly Thr Tyr Lys
        130                 135                 140

Leu Ser Gly Leu Arg Asn Phe Thr Gly Gly Asp Leu Asp Val Asn Met
145                 150                 155                 160

Gln Lys Ala Thr Leu Arg Leu Gly Gln Phe Asn Gly Asn Ser Phe Thr
                165                 170                 175

Ser Tyr Lys Asp Ser Ala Asp Arg Thr Thr Arg Val Asp Phe Asn Ala
                180                 185                 190

Lys Asn Ile Leu Ile Asp Asn Phe Leu Glu Ile Asn Asn Arg Val Gly
            195                 200                 205

Ser Gly Ala Gly Arg Lys Ala Ser Ser Thr Val Leu Thr Leu Gln Ala
        210                 215                 220

Ser Glu Gly Ile Thr Ser Ser Lys Asn Ala Glu Ile Ser Leu Tyr Asp
225                 230                 235                 240

-continued

Gly Ala Thr Leu Asn Leu Ala Ser Asn Ser Val Lys Leu Asn Gly Asn
                245                 250                 255

Val Trp Met Gly Arg Leu Gln Tyr Val Gly Ala Tyr Leu Ala Pro Ser
            260                 265                 270

Tyr Ser Thr Ile Asn Thr Ser Lys Val Thr Gly Glu Val Asn Phe Asn
        275                 280                 285

His Leu Thr Val Gly Asp His Asn Ala Ala Gln Ala Gly Ile Ile Ala
    290                 295                 300

Ser Asn Lys Thr His Ile Gly Thr Leu Asp Leu Trp Gln Ser Ala Gly
305                 310                 315                 320

Leu Asn Ile Ile Ala Pro Pro Glu Gly Gly Tyr Lys Asp Lys Pro Asn
                325                 330                 335

Asn Thr Pro Ser Gln Ser Gly Ala Lys Asn Asp Lys Gln Glu Ser Ser
            340                 345                 350

Gln Asn Asn Ser Asn Thr Gln Val Ile Asn Pro Pro Asn Ser Thr Gln
        355                 360                 365

Lys Thr Glu Val Gln Pro Thr Gln Val Ile Asp Gly Pro Phe Ala Gly
    370                 375                 380

Gly Lys Asp Thr Val Val Asn Ile Asp Arg Ile Asn Thr Lys Ala Asp
385                 390                 395                 400

Gly Thr Ile Lys Val Gly Gly Phe Lys Ala Ser Leu Thr Thr Asn Ala
                405                 410                 415

Ala His Leu Asn Ile Gly Lys Gly Gly Val Asn Leu Ser Asn Gln Ala
            420                 425                 430

Ser Gly Arg Thr Leu Leu Val Glu Asn Leu Thr Gly Asn Ile Thr Val
        435                 440                 445

Asp Gly Pro Leu Arg Val Asn Asn Gln Val Gly Gly Tyr Ala Leu Ala
    450                 455                 460

Gly Ser Ser Ala Asn Phe Glu Phe Lys Ala Gly Val Asp Thr Lys Asn
465                 470                 475                 480

Gly Thr Ala Thr Phe Asn Asn Asp Ile Ser Leu Gly Arg Phe Val Asn
                485                 490                 495

Leu Lys Val Asp Ala His Thr Ala Asn Phe Lys Gly Ile Asp Thr Gly
            500                 505                 510

Asn Gly Gly Phe Asn Thr Leu Asp Phe Ser Gly Val Thr Asn Lys Val
        515                 520                 525

Asn Ile Asn Lys Leu Ile Thr Ala Ser Thr Asn Val Ala Val Lys Asn
    530                 535                 540

Phe Asn Ile Asn Glu Leu Ile Val Lys Thr Asn Gly Val Ser Val Gly
545                 550                 555                 560

Glu Tyr Thr His Phe Ser Glu Asp Ile Gly Ser Gln Ser Arg Ile Asn
                565                 570                 575

Thr Val Arg Leu Glu Thr Gly Thr Arg Ser Ile Phe Ser Gly Gly Val
            580                 585                 590

Lys Phe Lys Ser Gly Glu Lys Leu Val Ile Asp Glu Phe Tyr Tyr Ser
        595                 600                 605

Pro Trp Asn Tyr Phe Asp Ala Arg Asn Ile Lys Asn Val Glu Ile Thr
    610                 615                 620

Arg Lys Phe Ala Ser Ser Thr Pro Glu Asn Pro Trp Gly Thr Ser Lys
625                 630                 635                 640

Leu Met Phe Asn Asn Leu Thr Leu Gly Gln Asn Ala Val Met Asp Tyr
                645                 650                 655

```
Ser Gln Phe Ser Asn Leu Thr Ile Gln Gly Asp Phe Ile Asn Asn Gln
                660                 665                 670

Gly Thr Ile Asn Tyr Leu Val Arg Gly Lys Val Ala Thr Leu Asn
            675                 680                 685

Val Gly Asn Ala Ala Met Met Phe Asn Asn Asp Ile Asp Ser Ala
690                 695                 700

Thr Gly Phe Tyr Lys Pro Leu Ile Lys Ile Asn Ser Ala Gln Asp Leu
705                 710                 715                 720

Ile Lys Asn Thr Glu His Val Leu Leu Lys Ala Lys Ile Ile Gly Tyr
                725                 730                 735

Gly Asn Val Ser Thr Gly Thr Asn Gly Ile Ser Asn Val Asn Leu Glu
            740                 745                 750

Glu Gln Phe Lys Glu Arg Leu Ala Leu Tyr Asn Asn Asn Asn Arg Met
            755                 760                 765

Asp Thr Cys Val Val Arg Asn Thr Asp Asp Ile Lys Ala Cys Gly Met
        770                 775                 780

Ala Ile Gly Asn Gln Ser Met Val Asn Asn Pro Asp Asn Tyr Lys Tyr
785                 790                 795                 800

Leu Ile Gly Lys Ala Trp Lys Asn Ile Gly Ile Ser Lys Thr Ala Asn
                805                 810                 815

Gly Ser Lys Ile Ser Val Tyr Tyr Leu Gly Asn Ser Thr Pro Thr Glu
            820                 825                 830

Asn Gly Gly Asn Thr Thr Asn Leu Pro Thr Asn Thr Thr Asn Asn Ala
            835                 840                 845

Arg Phe Ala Ser Tyr Ala Leu Ile Lys Asn Ala Pro Phe Ala His Ser
    850                 855                 860

Ala Thr Pro Asn Leu Val Ala Ile Asn Gln His Asp Phe Gly Thr Ile
865                 870                 875                 880

Glu Ser Val Phe Glu Leu Ala Asn Arg Ser Lys Asp Ile Asp Thr Leu
                885                 890                 895

Tyr Ala Asn Ser Gly Ala Gln Gly Arg Asp Leu Leu Gln Thr Leu Leu
            900                 905                 910

Ile Asp Ser His Asp Ala Gly Tyr Ala Arg Thr Met Ile Asp Ala Thr
            915                 920                 925

Ser Ala Asn Glu Ile Thr Lys Gln Leu Asn Thr Ala Thr Thr Thr Leu
930                 935                 940

Asn Asn Ile Ala Ser Leu Glu His Lys Thr Ser Ser Leu Gln Thr Leu
945                 950                 955                 960

Ser Leu Ser Asn Ala Met Ile Leu Asn Ser Arg Leu Val Asn Leu Ser
                965                 970                 975

Arg Arg His Thr Asn Asn Ile Asp Ser Phe Ala Lys Arg Leu Gln Ala
            980                 985                 990

Leu Lys Asp Gln Arg Phe Ala Ser  Leu Glu Ser Ala Ala  Glu Val Leu
        995                 1000                1005

Tyr Gln  Phe Ala Pro Lys Tyr  Glu Lys Pro Thr Asn  Val Trp Ala
        1010                1015                1020

Asn Ala  Ile Gly Gly Ala Ser  Leu Asn Asn Gly Gly  Asn Ala Ser
        1025                1030                1035

Leu Tyr  Gly Thr Ser Ala Gly  Val Asp Ala Tyr Leu  Asn Gly Gln
        1040                1045                1050

Val Glu  Ala Ile Val Gly Gly  Phe Gly Ser Tyr Gly  Tyr Ser Ser
        1055                1060                1065

Phe Asn  Asn Gln Ala Asn Ser  Leu Asn Ser Gly Ala  Asn Asn Thr
```

```
                    1070                1075                1080

Asn Phe Gly Val Tyr Ser Arg Ile Phe Ala Asn Gln His Glu Phe
        1085                1090                1095

Asp Phe Glu Ala Gln Gly Ala Leu Gly Ser Asp Gln Ser Ser Leu
        1100                1105                1110

Asn Phe Lys Ser Ala Leu Leu Arg Asp Leu Asn Gln Ser Tyr Asn
        1115                1120                1125

Tyr Leu Ala Tyr Ser Ala Ala Thr Arg Ala Ser Tyr Gly Tyr Asp
        1130                1135                1140

Phe Ala Phe Phe Arg Asn Ala Leu Val Leu Lys Pro Ser Val Gly
        1145                1150                1155

Val Ser Tyr Asn His Leu Gly Ser Thr Asn Phe Lys Ser Asn Ser
        1160                1165                1170

Thr Asn Lys Val Ala Leu Ser Asn Gly Ser Ser Gln His Leu
        1175                1180                1185

Phe Asn Ala Ser Ala Asn Val Glu Ala Arg Tyr Tyr Tyr Gly Asp
        1190                1195                1200

Thr Ser Tyr Phe Tyr Met Asn Ala Gly Val Leu Gln Glu Phe Ala
        1205                1210                1215

Asn Phe Gly Ser Ser Asn Ala Val Ser Leu Asn Thr Phe Lys Val
        1220                1225                1230

Asn Ala Thr Arg Asn Pro Leu Asn Thr His Ala Arg Val Met Met
        1235                1240                1245

Gly Gly Glu Leu Lys Leu Ala Lys Glu Val Phe Leu Asn Leu Gly
        1250                1255                1260

Val Val Tyr Leu His Asn Leu Ile Ser Asn Ile Gly His Phe Ala
        1265                1270                1275

Ser Asn Leu Gly Met Arg Tyr Ser Phe
        1280                1285

<210> SEQ ID NO 64
<211> LENGTH: 280
<212> TYPE: PRT
<213> ORGANISM: Helicobacter pylori

<400> SEQUENCE: 64

Met Leu Val Asp Ala Ile Arg Ile Asn Ala Asn Asp Leu Gly Ile Ala
1               5                   10                  15

Leu Phe Lys Leu Ile Thr Phe Gln Ile Phe Pro Thr Ile Thr Ile Val
                20                  25                  30

Met Phe Val Val Ala Phe Val Val Ile Val Ile Cys Ile Gln Asn Phe
        35                  40                  45

Ser Ser Ile Met Leu Ser Gly Asp Gly Tyr Lys Leu Ile Asp Pro Ser
    50                  55                  60

Lys Val Leu Ser Ser Lys Glu Asn Gln Ile His Arg Leu Leu Leu Glu
65                  70                  75                  80

Leu Leu Glu Glu Ala Lys Leu His Phe Glu Pro Lys Leu Tyr Ile Ile
                85                  90                  95

Asn Ala Pro Tyr Met Asn Ala Phe Ala Ser Gly Trp Asp Glu Ser Asn
                100                 105                 110

Ser Leu Ile Ala Leu Thr Ser Ala Leu Ile Glu Arg Leu Asp Arg Asp
        115                 120                 125

Glu Leu Lys Ala Val Ile Ala His Glu Leu Ser His Ile Arg His Asn
    130                 135                 140
```

```
Asp Ile Arg Leu Thr Met Cys Val Gly Ile Leu Ser Asn Ile Met Leu
145                 150                 155                 160

Leu Val Ala Asn Phe Ser Val Tyr Phe Phe Met Gly Asn Arg Lys Asn
                165                 170                 175

Ser Gly Ala Asn Leu Ala Arg Met Ile Leu Leu Leu Gln Ile Val
            180                 185                 190

Leu Pro Phe Leu Thr Leu Ile Leu Gln Met Tyr Leu Ser Arg Thr Arg
        195                 200                 205

Glu Tyr Met Ala Asp Ser Gly Ala Ala Phe Leu Met His Asp Asn Lys
        210                 215                 220

Pro Met Ile Arg Ala Leu Gln Lys Ile Ser Asn Asp Tyr Thr Asn Asn
225                 230                 235                 240

Asp Tyr Lys Glu Ile Asp Lys Asn Ser Thr Arg Ser Ala Ala Tyr Leu
                245                 250                 255

Phe Asn Ala Glu Met Phe Ser Thr His Pro Ser Ile Lys Asn Arg Ile
                260                 265                 270

Gln Ser Leu Ser Arg Arg Met Ile
            275                 280

<210> SEQ ID NO 65
<211> LENGTH: 238
<212> TYPE: PRT
<213> ORGANISM: Helicobacter pylori

<400> SEQUENCE: 65

Met Lys Leu Thr Pro Lys Glu Leu Asp Lys Leu Met Leu His Tyr Ala
1               5                   10                  15

Gly Glu Leu Ala Lys Lys Arg Lys Glu Lys Gly Ile Lys Leu Asn Tyr
            20                  25                  30

Val Glu Ala Val Ala Leu Ile Ser Ala His Ile Met Glu Glu Ala Arg
        35                  40                  45

Ala Gly Lys Lys Thr Ala Ala Glu Leu Met Gln Glu Gly Arg Thr Leu
    50                  55                  60

Leu Lys Pro Asp Asp Val Met Asp Gly Val Ala Ser Met Ile His Glu
65                  70                  75                  80

Val Gly Ile Glu Ala Met Phe Pro Asp Gly Thr Lys Leu Val Thr Val
                85                  90                  95

His Thr Pro Ile Glu Ala Asn Gly Lys Leu Val Pro Gly Glu Leu Phe
            100                 105                 110

Leu Lys Asn Glu Asp Ile Thr Ile Asn Glu Gly Lys Lys Ala Val Ser
        115                 120                 125

Val Lys Val Lys Asn Val Gly Asp Arg Pro Val Gln Ile Gly Ser His
130                 135                 140

Phe His Phe Phe Glu Val Asn Arg Cys Leu Asp Phe Asp Arg Glu Lys
145                 150                 155                 160

Thr Phe Gly Lys Arg Leu Asp Ile Ala Ser Gly Thr Ala Val Arg Phe
                165                 170                 175

Glu Pro Gly Glu Glu Lys Ser Val Glu Leu Ile Asp Ile Gly Gly Asn
            180                 185                 190

Arg Arg Ile Phe Gly Phe Asn Ala Leu Val Asp Arg Gln Ala Asp Asn
        195                 200                 205

Glu Ser Lys Lys Ile Ala Leu His Arg Ala Lys Glu Arg Gly Phe His
    210                 215                 220

Gly Ala Lys Ser Asp Asp Asn Tyr Val Lys Thr Ile Lys Glu
225                 230                 235
```

```
<210> SEQ ID NO 66
<211> LENGTH: 569
<212> TYPE: PRT
<213> ORGANISM: Helicobacter pylori

<400> SEQUENCE: 66

Met Lys Lys Ile Ser Arg Lys Glu Tyr Val Ser Met Tyr Gly Pro Thr
1               5                   10                  15

Thr Gly Asp Lys Val Arg Leu Gly Asp Thr Asp Leu Ile Ala Glu Val
            20                  25                  30

Glu His Asp Tyr Thr Ile Tyr Gly Glu Leu Lys Phe Gly Gly Gly
        35                  40                  45

Lys Thr Leu Arg Glu Gly Met Ser Gln Ser Asn Asn Pro Ser Lys Glu
    50                  55                  60

Glu Leu Asp Leu Ile Ile Thr Asn Ala Leu Ile Val Asp Tyr Thr Gly
65                  70                  75                  80

Ile Tyr Lys Ala Asp Ile Gly Ile Lys Asp Gly Lys Ile Ala Gly Ile
                85                  90                  95

Gly Lys Gly Gly Asn Lys Asp Met Gln Asp Gly Val Lys Asn Asn Leu
            100                 105                 110

Ser Val Gly Pro Ala Thr Glu Ala Leu Ala Gly Glu Gly Leu Ile Val
        115                 120                 125

Thr Ala Gly Gly Ile Asp Thr His Ile His Phe Ile Ser Pro Gln Gln
130                 135                 140

Ile Pro Thr Ala Phe Ala Ser Gly Val Thr Thr Met Ile Gly Gly Gly
145                 150                 155                 160

Thr Gly Pro Ala Asp Gly Thr Asn Ala Thr Thr Ile Thr Pro Gly Arg
                165                 170                 175

Arg Asn Leu Lys Trp Met Leu Arg Ala Ala Glu Glu Tyr Ser Met Asn
            180                 185                 190

Leu Gly Phe Leu Ala Lys Gly Asn Ala Ser Asn Asp Ala Ser Leu Ala
        195                 200                 205

Asp Gln Ile Glu Ala Gly Ala Ile Gly Phe Lys Ile His Glu Asp Trp
210                 215                 220

Gly Thr Thr Pro Ser Ala Ile Asn His Ala Leu Asp Val Ala Asp Lys
225                 230                 235                 240

Tyr Asp Val Gln Val Ala Ile His Thr Asp Thr Leu Asn Glu Ala Gly
                245                 250                 255

Cys Val Glu Asp Thr Met Ala Ala Ile Ala Gly Arg Thr Met His Thr
            260                 265                 270

Phe His Thr Glu Gly Ala Gly Gly Gly His Ala Pro Asp Ile Ile Lys
        275                 280                 285

Val Ala Gly Glu His Asn Ile Leu Pro Ala Ser Thr Asn Pro Thr Ile
290                 295                 300

Pro Phe Thr Val Asn Thr Glu Ala Glu His Met Asp Met Leu Met Val
305                 310                 315                 320

Cys His His Leu Asp Lys Ser Ile Lys Glu Asp Val Gln Phe Ala Asp
                325                 330                 335

Ser Arg Ile Arg Pro Gln Thr Ile Ala Ala Glu Asp Thr Leu His Asp
            340                 345                 350

Met Gly Ile Phe Ser Ile Thr Ser Ser Asp Ser Gln Ala Met Gly Arg
        355                 360                 365

Val Gly Glu Val Ile Thr Arg Thr Trp Gln Thr Ala Asp Lys Asn Lys
370                 375                 380
```

-continued

```
Lys Glu Phe Gly Arg Leu Lys Glu Glu Lys Gly Asp Asn Asp Asn Phe
385                 390                 395                 400

Arg Ile Lys Arg Tyr Leu Ser Lys Tyr Thr Ile Asn Pro Ala Ile Ala
                405                 410                 415

His Gly Ile Ser Glu Tyr Val Gly Ser Val Glu Val Gly Lys Val Ala
            420                 425                 430

Asp Leu Val Leu Trp Ser Pro Ala Phe Phe Gly Val Lys Pro Asn Met
        435                 440                 445

Ile Ile Lys Gly Gly Phe Ile Ala Leu Ser Gln Met Gly Asp Ala Asn
    450                 455                 460

Ala Ser Ile Pro Thr Pro Gln Pro Val Tyr Tyr Arg Glu Met Phe Ala
465                 470                 475                 480

His His Gly Lys Ala Lys Tyr Asp Ala Asn Ile Thr Phe Val Ser Gln
            485                 490                 495

Ala Ala Tyr Asp Lys Gly Ile Lys Glu Glu Leu Gly Leu Glu Arg Gln
            500                 505                 510

Val Leu Pro Val Lys Asn Cys Arg Asn Ile Thr Lys Lys Asp Met Gln
        515                 520                 525

Phe Asn Asp Thr Thr Ala His Ile Glu Val Asn Pro Glu Thr Tyr His
        530                 535                 540

Val Phe Val Asp Gly Lys Glu Val Thr Ser Lys Pro Ala Asn Lys Val
545                 550                 555                 560

Ser Leu Ala Gln Leu Phe Ser Ile Phe
                565
```

PROTEIN MICROARRAY FOR CHARACTERIZING THE SPECIFICITY OF THE MONOCLONAL IMMUNOGLOBULINS OF MGUS OR MYELOMA PATIENTS

The present invention concerns materials and methods for characterizing monoclonal immunoglobulin specificity of a Monoclonal Gammopathy of Undetermined Significance (MGUS) or myeloma patients using a protein microarray. In particular said protein microarray may be used in methods to improve diagnostic and for the prognosis of the outcome of multiple myeloma or preventing transformation of MGUS toward myeloma or treating MGUS or myeloma.

BACKGROUND OF THE INVENTION

Myeloma is a malignant proliferation of plasma cells, which produce a monoclonal immunoglobulin (mc Ig). Myeloma is probably a multi-event disease, with the classical three step-development observed in cancer: initiation, promotion and progression. It is now established that all myeloma derive from a chronic state called Monoclonal Gammopathy of Undetermined Significance (MGUS). The risk of transformation of MGUS into myeloma is estimated at 1% per year per patient. Every year in Europe 20000 new cases of myeloma are diagnosed, and 3-5% of the UE population over 50 (close to 21 millions) present with MGUS. Yet numerous differences can be observed between myeloma and MGUS and healthy patients: variable isotype of monoclonal immunoglobulin (mc Ig), chronic infection, genetic lesions, and epigenetic changes.

Despite extensive biological and clinical research and numerous clinical trials, the etiopathology of MGUS and its evolution in myeloma remain largely unanswered questions. Different disease profiles may explain different disease evolutions and different treatment responses. Although numerous biological, clinical, therapeutic studies have been performed in the past decades yet the median survival in myeloma remains short (5 years), suggesting that new approaches to the MGUS and myeloma pathogenesis are still necessary.

Hence, it becomes urgent to find novel biomarkers useful to improve diagnosis and prognosis, and extend therapeutic options for this group of diseases. A promising approach is that MGUS and subsequently, myeloma result from antigen (Ag)-driven clonal proliferation, a pathogenic mechanism well established in other B-cell lineage malignancies but surprisingly neglected in myeloma and MGUS. Clonal myeloma plasma cells synthesize large amounts of Immunoglobulin (Ig) known as monoclonal immunoglobulin (mc Ig), but the role played by mc Ig production has not been investigated.

Patients with MGUS are currently not treated and not monitored for the risk of progression to myeloma. Heterogeneity of myeloma patients is acknowledged but the current efforts of patient stratification in regard of disease progression and response to treatment is limited to cytogenetic and genomic abnormalities, which are often secondary events in myeloma.

In current practice, mc Ig from patients diagnosed with myeloma or MGUS are assumed not to have functional antibody activity and their specificity is not studied.

Monoclonal gammopathy presenting patients are currently diagnosed by performing electrophoresis of patient plasma. However, those techniques remain insufficiently sensitive and do not take into account the specificity of mc Ig.

A previous study investigated the humoral immune status of patients with MGUS or myeloma in relation to common infectious agents (Karlsson et al. 2011 *Clin Vaccine Immunol.* 2011 June; 18(6):969-77. doi: 10.1128/CV1.00021-11). However, the determination of the humoral immune status of patients was done by testing serum samples, and the inventors have demonstrated that the reactivity of a serum sample is not indicative of the specificity of the mc Ig contained in the serum sample.

The inventors previously disclosed in a case report, the description of a patient suffering from plasma cell leukemia and having a mc Ig directed against the core protein of hepatitis C virus (HCV) (Hermouet S. et al., 2003 *N Engl J Med;* 348:178-179). Moreover, the inventors described 10 additional HCV-positive patients identified in a cohort of 700 patients presenting with a mc Ig. Mc Ig was purified for 7/10 patients and in 6/7 cases, the mc Ig was directed against HCV antigens and notably against HCV core protein and NS-4 protein (E. Bigot-Corbel E. et al., 2008 *Blood.* November 15; 112(10):4357-8).

No systematic study of the specificity of mc Ig has ever been done because screening mc Ig for a panel of Ag using classical assays such as ELISAs required purification of mc Ig and large quantities of purified mc Ig, usually not available. Other assays such as epitope reconstruction or epitope mediated antigen prediction (E-MAP) have proved disappointing because their technical complexity makes them difficult to use in clinical practice, and results obtained by these techniques need to be confirmed by other methods after purification of mc Ig.

In addition, these techniques are of indicative different value only and it is necessary to study the specificity of mc Ig with other assays.

BRIEF SUMMARY OF THE INVENTION

The invention concerns a protein microarray or a multiplexed infectious protein (MIP) microarray comprising (a) a substrate, (b) antigens immobilized on said substrate, wherein said antigens comprise (i) at least one infectious agent antigen and/or (ii) at least one self antigen.

The invention also concerns a method for producing a protein microarray, which method comprises:
(a) providing antigens, wherein said antigens are an infectious agent antigen and/or a self-antigen.
(b) contacting a substrate with said antigens, and
(c) immobilizing said antigens on the substrate.

Also provided is a method for determining whether a Monoclonal Gammopathy of Undetermined Significance (MGUS) or Myeloma patient carries monoclonal immunoglobulin (mc Ig) specific for an infectious agent or for a self antigen, wherein said method comprises a protein microarray assay comprising the steps of:
a) incubating a biological sample of the MGUS or myeloma patient with a protein microarray comprising (a) a substrate, (b) antigens immobilized on said substrate, wherein said antigens are selected from the group consisting of at least one infectious agent antigen and/or at least one self-antigen,
b) detecting if said monoclonal immunoglobulin is bound to said antigens.

The invention further provides methods of prognosing the outcome of myeloma, of prognosing the potential of a monoclonal gammopathy of undetermined significance (MGUS) to progress to myeloma and of diagnosing a relapse of a myeloma patient or a therapy refractory myeloma patient, and of monitoring the response to a therapy in a myeloma patient wherein said method comprises the step of determining whether a mc Ig of said patient is specific for an infectious agent or for a self antigen using the method according to the invention.

The invention further provides use of a protein microarray for characterizing the specificity of mc Ig from MGUS or myeloma patients wherein said protein microarray comprises (a) a substrate, (b) antigens immobilized on said substrate, wherein said antigens are selected from the group consisting of at least one infectious agent antigen and/or at least one self-antigen.

The invention also concerns a method for treating a MGUS patient or improving the treatment of myeloma patients or preventing myeloma in a patient having an MGUS comprising (a) the method of determining whether the mc Ig of a patient is specific for an infectious agent or for a self antigen according to the invention and (b) the step of treating the patient with complementary adequate drugs such as anti-infectious or immunosuppressive drugs.

DETAILED DESCRIPTION OF THE INVENTION

The inventors hypothesize that the MGUS state reflects an abnormal response to chronic antigen stimulation that may eventually progress toward malignant myeloma, and that chronic Ag stimulation is implicated in MGUS and myeloma pathogenesis. Thus, diagnosis and treatment of a chronic infection or an autoimmune disease in a MGUS or myeloma patient and its treatment may be of use for prognosing, preventing and/or treating MGUS or myeloma. The inventors have shown that mc Ig specific for antigens of chronic infectious agents such as HCV, Epstein-Barr virus (EBV) and *Helicobacter Pylori* (*H. Pylori*), can be detected in serum from at least 20% of MGUS and myeloma patients, after mc Ig purification, using a microarray format. Such protein microarrays allow efficient diagnosis with a higher sensitivity than the methods of the prior art.

The invention therefore provides a multiplexed infectious protein (MIP) microarray comprising (a) a substrate, (b) antigens immobilized on said substrate, wherein said antigens comprise (i) at least one infectious agent antigen and/or (ii) at least one self antigen.

Preferably, the invention provides a protein microarray comprising
  (a) a substrate,
  (b) antigens immobilized on said substrate, wherein said antigens comprise infectious agent antigens which comprise at least one HCV specific antigen, at least one EBV specific antigen and at least one *H. pylori* specific antigen and optionally at least one self antigen,
  (c) optionally a control sample.

The invention further provides a method for producing a protein microarray, which method comprises:
  (a) providing antigens, wherein said antigens comprise at least one infectious agent antigen and/or at least one self antigen,
  (b) contacting a substrate with said antigens, and
  (c) immobilizing said antigens on the substrate.

Preferably, the invention provides a method for producing a protein microarray, which method comprises:
  (a) providing antigens, wherein said antigens comprise at least one infectious agent antigens which comprise at least one HCV specific antigen, at least one EBV specific antigen and at least one *H. pylori* specific antigen and optionally at least one self antigen,
  (b) contacting a substrate with said antigens, and
  (c) immobilizing said antigens on the substrate.

Substrates for use in the invention can be any support or matrix suitable for attaching proteins. Suitable substrates include, but are not limited to, silicon, nitrocellulose, diazocellulose, glass, polystyrene (including microtitre plates), polyvinylchloride, polypropylene, polyethylene, polyvinylidenedifluoride (PVDF), dextran, sepharose, agar, starch, nylon, and metal. The substrate can be in any form or configuration, including chips, plates, beads, filters, membranes, sheets, frits, plugs, columns, and the like. The substrate can also include multi-well tubes or plates, such as 12-well plates, 24-well plates, 48-well plates, 96-well plates, and 384-well plates. Preferred beads are made of glass, latex, or a magnetic material (magnetic, paramagnetic, or superparamagnetic beads).

According to the invention the antigens are immobilized directly on the substrate using routine methods known in the art. Indeed, the antigen according to the invention can be applied, printed, or spotted onto the substrate using photolithography, pipetting, drop-touch methods, piezoelectric (ink-jet) methods, electric methods, robotic methods, and other methods known in the art. The antigen can be immobilized on a particular substrate by noncovalent or covalent interactions. In this regard, polypeptide sequences can be noncovalently immobilized on a glass slide coated with, for example, either poly-L-lysine or aminopropyltri-ethoxysilane. However, the polypeptides preferably are immobilized on the substrate via covalent interactions. In this regard, for example, proteins can be spotted on glass slides coated with aminosilane, poly-L-lysine, or agarose film, and immobilized on the slides by the Schiff base aldehyde-amine chemistry. Protein microarray fabrication, immobilization, and analysis are further described in, for example, H. Zhu, M. Snyder, Protein chip technology, Curr Opin Chem Biol. 7 (2003) 55-63; R. Wiese, Y. Belosludtsev, T. Powdrill, P. Thompson, M. Hogan, Simultaneous multianalyte ELISA performed on a microarray platform, Clin Chem. 47 (2001) 1451-1457.

The peptide or polypeptide or protein or protein variants or fragments may be synthesized and/or purified from lysates before being attached to the substrate. Alternatively they can be synthesized in-situ and directly attached to the substrate. The peptide or polypeptide or protein or protein variants or fragments can be synthesized through biosynthesis, cell-free DNA expression or chemical synthesis. In-situ synthesis is possible with the latter two.

In this embodiment, preferably at least one antigen is applied to the same location on the substrate. One of ordinary skill in the art will appreciate that more than one location (or "spot") on the substrate can contain two or more (e.g., 2, 5, 10, 20, 100, or more) antigens. The first and second antigen can be applied to the substrate using any suitable method described herein. For example if the antigens are two polypeptides, the first and second polypeptides are preferably different. Alternatively the substrate can contain the same location, two or more (e.g., 2, 5, 10, 20, 100, or more) polypeptide sequences and/or two or more (e.g., 2, 5, 10, 20, 100, or more) infectious agent lysates and/or one or more (e.g., 2, 5, 10, 20, 100, or more) polypeptide(s) with one or more (e.g., 2, 5, 10, 20, 100, or more) infectious agent lysate(s).

As used herein, an "antigen" relates to any substance or compound that triggers the production of an antibody by the immune system in an animal, including a human. Antigen refers also to a substance which is a ligand of an antibody to which it binds. The term "epitope" as used herein means the portion of the antigen which interacts with an antibody. When the antigen is a protein, said portion may be a specific amino acid sequence, a modified amino acid sequence, or a protein secondary or tertiary structure. The antigen of the invention may be for example, infectious agent antigen or self antigen.

The term "self antigen" refers to an endogenous body constituent, usually a protein or a peptide that stimulates the production of autoantibodies and an autoimmune reaction. For example, a self antigen may be a polypeptide selected from the group consisting of the Actin 1 (ACC No P60709, Checksum 6AFD05CA94E360E2, SEQ ID NO: 19), the Actin 2 (or cytoplasmic 2) (ACC No P63261, Checksum 54D08F986964EFD5, SEQ ID NO: 20), the tubulin beta chain (ACC No P07437, Checksum 1E6CD0A36773A103, SEQ ID NO: 21), the tubulin delta chain (Q9UJT1, Checksum 2D78AB3D9EEB9158, SEQ ID NO: 22), the carbonic anhydrase 1 (ACC No P00915, Checksum 4959E5FA25E374F8, SEQ ID NO: 23), the carbonic anhydrase 2 (ACC No P00918, Checksum 2EC2BB7548F10558, SEQ ID NO: 24), the carbonic anhydrase 6 (ACC No P23280, Checksum 6EBFF15085E7112D, SEQ ID NO: 25), the carbonic anhydrase 4 (ACC No P22748, Checksum EF5F182474ABE9B0, SEQ ID NO: 26), the human Serum albumin (ACC No P02768, Checksum F88FF61DD242E818, SEQ ID NO: 27), the human thyroglobulin (ACC No P01266; Checksum 69A87D935F1BAA72), the human Fetuin-B (ACC No Q9UGM5, Checksum C73977793A30AF8A, SEQ ID NO: 59), the paratarg-7 (pP-7) which has an amino acid sequence identical to the Stomatin-like protein 2 (ACC No Q9UJZ1, Checksum 672331B57C82654E, SEQ ID NO: 61) or a variant or fragment thereof. A self antigen may further be a polypeptide comprising a fragment of the human thyroglobulin such as for example a polypeptide having the sequence SEQ ID NO: 28 (ACC No H0YB42, Checksum 571B96BF1B06BB78) or SEQ ID NO: 29 (ACC No H0YBC5, Checksum B975F7CFD81F28AE) or a variant or fragment thereof.

An "Infectious agent antigen" means, according to the invention, an antigen which is specific for an infectious agent. Said antigen may be a purified or a synthetic antigen or a lysate of said infectious agent. "Infectious agent" means any microorganism capable of producing infection. In some embodiments, said infectious agent causes chronic infection. The term "infection" means the invasion of body tissues of an individual by disease-causing microorganisms, their multiplication and the reaction of body tissues to these microorganisms and the toxins that they produce. The infection may be acute or chronic. The term "chronic infection" refers to a long-term infection which may be an apparent, unapparent or latent infection.

In one embodiment, the infectious agent may be without limitation, a virus, bacterium or a parasite and notably Hepatitis C virus (HCV), Epstein-Barr Virus (EBV), Hepatitis B virus (HBV), Human immunodeficiency virus (HIV), cytomegalovirus (CMV), varicella zoster virus, Human Herpes Virus 1 (HHV-1), HHV-2, HHV-6, HHV-8, coxsackie virus B4, influenza A and B viruses, Measles virus, Rubella virus; *Staphylococcus aureus*, *Streptococcus* A, *Helicobacter pylori*, *Chlamydia trachomatis*, *Mycoplasma pneumoniae*, *Haemophilus influenza*, *Borrelia burgdorferi*; *Bartonella Hensalae*; *Toxoplasma gondii*, *Candida albicans*, *Porphyromonas gingivalis*, Prevotellaceae.

The infectious agent antigen may be a virus-specific antigen such as a CMV specific antigen, an EBV specific antigen, a HCV specific antigen, a HBV specific antigen, a Varicella zoster virus specific antigen, a Rubella virus specific antigen or a Measles virus specific antigen.

In one embodiment, said infectious agent antigen or said virus-specific antigen is not an HCV specific antigen.

The infectious agent antigen may be a parasite specific antigen such as a *T. gondii* specific antigen or a *Candida albicans* specific antigen.

The infectious agent antigen may further be a bacteria specific antigen such as a *Porphyromonas gingivalis* specific antigen, a *Chlamydia trachomatis* specific antigen, a *Borrelia bugdorferi* specific antigen or a *Helicobacter pylori* specific antigen.

The term "specific", in the expressions "infectious agent specific antigen", "bacterial specific antigen" or "HCV specific antigen" or the like, means that the antigen is constitutive to, expressed or secreted by this infectious agent and is specific to this infectious agent (as opposed to other infectious agents, microorganisms or organisms).

The term "multiplexed infectious protein microarray" or "MIP" means a protein microarray comprising infectious agent immobilized antigens such as lysates, proteins, peptides, and recombinant epitopes. Said infectious agent antigens are from diverse infectious agent origins.

In preferred embodiments, the antigens immobilized on the microarray of the invention comprise or consist of a CMV specific antigen, and/or a *T. gondii* specific antigen, and/or a HCV specific antigen, and/or an EBV specific antigen. Said antigen or antigens may comprise or consist of any one or more of the specific antigens identified herein.

"CMV specific antigen" may be for example a polypeptide comprising the amino acid sequence of the Cytomegalovirus 65 kDa phosphoprotein (pp65) (ACC No P06725, Checksum 37422EA149E88F30 SEQ ID NO: 60) or a polypeptide comprising a fragment of the pp65 such as for example a polypeptide having the sequence SEQ ID NO: 1 or a polypeptide having amino acids 297-510 of SEQ ID NO: 60; the 28 kDa phosphoprotein (pp28) (ACC No P13200, Checksum A08CC061D2B4B792, SEQ ID NO: 2); the CMV DNA polymerase processivity factor (or 52 kDa phosphoprotein pp52) (ACC No P16790, Checksum E3BDF4C05E4C040A, SEQ ID NO: 3); the Envelope glycoprotein B (ACC No P06473 Checksum D4C7A6A3C7083FEE, SEQ ID NO:4), the CMV Capsid maturation protease (or pp38 or UL80a) (ACC No B8YEA5 Checksum 32A993D6586824C9, SEQ ID NO:5), or a variant or fragment thereof.

"*T. gondii* specific antigen" may be for example a polypeptide comprising the amino acid sequence of the Major antigen p24 or Dense granule protein 1 (GRA1) protein (ACC No P13403, Checksum 3B05D2610C615A53, SEQ ID NO 6), or a variant or fragment thereof.

"HCV specific antigen" may be for example a polypeptide comprising the amino acid sequence of the HCV core protein (ACC No Q86927 protein, Checksum 86C97CAC358E819A, SEQ ID NO: 8), the HCV genotype 1 b core protein (Q68843 protein, Checksum 251AC56249B26432, SEQ ID NO: 7); the HCV genotype 3b core protein (ACC No Q68861 protein, Checksum 2C38B48C6BB9C16A, SEQ ID NO: 9), the HCV genotype 3 g core protein (ACC No Q68863 protein, Checksum BC2932134026E5FD, SEQ ID NO: 10), the NS-4 recombinant mosaic protein from 1, 2, 3, 5 genotypes (SEQ ID NO 13; ACC No Q81594 polypeptide, Checksum 76648D9BB1D3CD12), the P7 NS-2 protein preferably a polypeptide comprising a sequence SEQ ID NO: 47 (Checksum 29DA4EA2575010C3, ACC No Q8UWY6) or a variant or fragment thereof.

The HCV specific antigen may further be a polypeptide comprising the amino acid sequence of the NS-2 protein preferably a fragment of the NS-2 protein such as for example a polypeptide having a sequence comprising SEQ ID NO: 45 (Checksum 9CD421E44C20EB3B, ACC No A0SQM1), SEQ ID NO: 46 (Checksum DF9641 BB8B55A857, Q9J3F5) or a variant or fragment thereof.

The HCV specific antigen may further be a polypeptide comprising the amino acid sequence of the NS-3 protein preferably a fragment of the NS-3 protein such as for example a polypeptide comprising the NS-3 protein recombinant fragment subtype 1c (ACC No Q04045 polypeptide, Checksum 3371E229ED6B117A, SEQ ID NO 11), the sequence SEQ ID NO: 12 (ACC No A3EZH6 polypeptide, Checksum B6A0867B8318D75D) or a variant or fragment thereof.

The HCV specific antigen may further be a polypeptide comprising the amino acid sequence of the NS-5 protein preferably a fragment of the NS-5 protein such as for example a polypeptide comprising a sequence selected from the group consisting of SEQ ID NO: 42 (Checksum 3E6D81759AF0616C, ACC No Q81596), SEQ ID NO: 43 (Checksum 75B77DAF53F696FA, ACC No Q00698) and SEQ ID NO: 44 (Checksum 8100E1378837A3B3, Q68298) or a variant or fragment thereof.

"HBV specific antigen" may be for example a polypeptide comprising the amino acid sequence of the HBs antigen (ACC No Q9JG36, Checksum EB11B70459FBC39A, SEQ ID NO: 57), the Core protein (or HBc antigen) (ACC No Q784Z8, Checksum ED2DA1 DB07FB596D, SEQ ID NO: 58) or a variant or fragment thereof.

"EBV specific antigen" may be for example the Viral Capsid Antigen (VCA) preferably a polypeptide comprising the amino acid sequence of the Major Capsid protein (SEQ ID NO: 15; ACC No P00704, Checksum CF1901F68A06F5C5), the Capsid protein VP26 (ACC No P14348, Checksum DAB605ED00F1A656; SEQ ID NO: 14) or a variant or fragment thereof such as a polypeptide having amino acids 1-162 of SEQ ID NO: 15. The EBV specific antigen may further be for example the Epstein-Barr Nuclear Antigen (EBNA) such as the EBNA 1 (ACC No P03211, Checksum 4D161653E16FC341, SEQ ID NO: 16), the EBNA 2 (ACC No P12978, Checksum DEF40D7F8ED61D1A, SEQ ID NO: 17), the EBNA LP (ACC No Q1HVI8, Checksum 81E6D7AF1E773998, SEQ ID NO: 18) or a variant or fragment thereof.

"Porphyromonas gingivalis specific antigen" may be for example a polypeptide comprising the amino acid sequence selected from the group consisting of SEQ ID NO: 30 (ACC No Q7MXM8, Checksum 88CF44ECC80ECBF2), SEQ ID NO: 31 (ACC No Q7MX54 Checksum 9C67034E31D89900), the amino acid sequence of the 53 kDa major outer membrane protein (ACC No Q9RM67, Checksum ECEED2CAE848AB1B, SEQ ID NO: 32) or a variant or fragment thereof.

"Chlamydia trachomatis specific antigen" may be for example a polypeptide comprising the amino acid sequence of the Chlamydia protein associating with death domain (ACC No G4NMQ5, Checksum 91CA47B123C53C96, SEQ ID NO: 33), the Virulence plasmid protein pGP3-D (ACC No P0CE18, Checksum CE62244839F8971B, SEQ ID NO: 34), the Protein CT_858 (ACC No O84866, Checksum 2D6B3068C546205B, SEQ ID NO: 35) or a variant or fragment thereof.

"Borrelia bugdorferi specific antigen" may be for example a polypeptide comprising the amino acid sequence of the BBR25 lipoprotein (ACC No B7J055, Checksum BA3A52F642E0C2D7, SEQ ID NO: 36), the REV protein (ACC No E4QHM1, Checksum 7A307F804CBA2B7E, SEQ ID NO: 37), the Borrelia burgdorferi virulent strain associated lipoprotein (ACC No O50869 Checksum 0DA265398BA28B43, SEQ ID NO: 38) or a variant or fragment thereof.

"Varicella zoster virus specific antigen" may be for example a polypeptide comprising the amino acid sequence of the Envelope glycoprotein B (ACC No Q4JR05 Checksum 4397ABA2A874C570, SEQ ID NO: 39), the Envelope protein US9 (ACC No Q77NN6, Checksum 18801A669057A3A3, SEQ ID NO: 40), the Structural protein 1 (ACC No Q4JQX4 Checksum FCF865BAE45F171F, SEQ ID NO: 41) or a variant or fragment thereof.

"Helicobacter pylori specific antigen" may be for example a polypeptide comprising the amino acid sequence of the Flagellin B (or Flagellin N) (ACC No Q07911, Checksum 1E3D0728BD14A584, SEQ ID NO: 48), the Flagellin A (ACC No P0A0S1, Checksum E802CCB74474A65A, SEQ ID NO: 49), the Flagellar P-ring protein (ACC No Q1CUQ6, Checksum 192849179F2C9B8D, SEQ ID NO: 50), CagA protein (AAC No P80200, Checksum AB92770835F68490, SEQ ID NO: 62) VacA protein (ACC No Q48245, Checksum 0007370062FCB71F SEQ ID NO: 63), Heat shock protein (AAC No B5Z7T1, Checksum E664297B048BDA73 SEQ ID NO: 64), Urease A protein (AAC No P14916, Checksum 4E77328669CD9A2D, SEQ ID NO: 65), Urease B protein (AAC No P69996, Checksum 4C8A6BC6C8295584, SEQ ID NO: 66) or a variant or fragment thereof.

"Rubella virus specific antigen" may be for example a polypeptide comprising the amino acid sequence of the Structural polyprotein (pp110) (ACC No P07566, Checksum F39B475ACA15C7D1, SEQ ID NO: 51), preferably a polypeptide comprising a sequence of amino acids 1-300 (which is the Capsid protein), 301-582 (which is the E2 envelope glycoprotein) or 583-1063 (which is the E1 envelope glycoprotein) of SEQ ID NO:51, or an immunogenic fragment having a sequence of amino acids 301-534, 583-1028 or 1050-1063 of sequence SEQ ID NO 51 or a variant or fragment thereof. The Rubella virus specific antigen may further be a polypeptide comprising the Non-structural protein (ACC No E7FL28, Checksum 3AFAF4293D8CCA36, SEQ ID NO: 52), preferably a polypeptide comprising a sequence of amino acids 1-1301 (which is the p150 protein), 1302-2116 (which is the p90 protein) of SEQ ID NO: 52 or a variant or fragment thereof.

"Measles virus specific antigen" may be for example a polypeptide comprising the amino acid sequence of the Hemagglutinin glycoprotein (ACC No P08362, Checksum 0E5A05AEDA43D9C6, SEQ ID NO: 53), the Non-structural protein V (ACC No Q9EMA9, Checksum 8B545804E0CF25AD, SEQ ID NO: 54), the Matrix protein (ACC No Q9W850, Checksum 471E73537F58BC1D, SEQ ID NO: 55), the Protein C (ACC No P35977, Checksum 73A1897D32BE7B19, SEQ ID NO: 56) or a variant or fragment thereof.

An infectious agent specific antigen or the self antigen may be a polypeptide comprising at least one fragment or variant of a protein. In the case of infectious agent specific antigen, the protein is coded by this infectious agent.

According to one embodiment, said infectious agent antigens comprise:
  at least one HCV specific antigen comprising an HCV lysate and/or at least one polypeptide comprising a sequence selected from the group consisting of SEQ ID NO: 7, SEQ ID NO: 8, SEQ ID NO: 9, SEQ ID NO: 10, the amino acids 1192-1459 of SEQ ID NO: 11, SEQ ID NO 12, SEQ ID NO: 13, the amino acids 1691-1710 of SEQ ID NO: 13, the amino acids 1712-1733 of SEQ ID NO: 13, the amino acids 1921-1940 of SEQ ID NO: 13, a variant or fragment thereof, at least one EBV specific antigen comprising an EBV lysate and/or at least one polypeptide comprising a sequence selected from the group consisting of SEQ ID NO: 16, amino acid sequence 1-162 of SEQ ID NO: 15, a variant or a fragment thereof, and at least one H. pylori specific antigen comprising an H. pylori lysate and/or at least one polypeptide selected from the group consisting of SEQ ID NO: 62, SEQ ID NO: 63, SEQ ID NO: 64, SEQ ID NO: 65, SEQ ID NO: 66, a variant or a fragment thereof.

According to another embodiment, said infectious agent antigens comprise:

at least one HCV specific antigen comprising a polypeptide of sequence SEQ ID NO: 7, SEQ ID NO: 11 and SEQ ID NO: 13 or SEQ ID NO: 8, SEQ ID NO: 11 and SEQ ID NO: 13 or SEQ ID NO: 9, SEQ ID NO: 11 and SEQ ID NO: 13 or SEQ ID NO: 10, SEQ ID NO: 11 and SEQ ID NO: 13 or SEQ ID NO: 7, SEQ ID NO: 12 and SEQ ID NO: 13 SEQ ID NO: 8, SEQ ID NO: 12 and SEQ ID NO: 13 or SEQ ID NO: 9, SEQ ID NO: 12 and SEQ ID NO: 13 or SEQ ID NO: 10, SEQ ID NO: 12 and SEQ ID NO: 13 or SEQ ID NO: 7, SEQ ID NO: 8, SEQ ID NO: 11 and SEQ ID NO: 13 or SEQ ID NO: 7, SEQ ID NO: 9, SEQ ID NO: 11 and SEQ ID NO: 13 or SEQ ID NO: 7, SEQ ID NO: 10, SEQ ID NO: 11 and SEQ ID NO: 13 or SEQ ID NO: 8, SEQ ID NO: 9, SEQ ID NO: 11 and SEQ ID NO: 13 or SEQ ID NO: 8, SEQ ID NO: 10, SEQ ID NO: 11 and SEQ ID NO: 13 or SEQ ID NO: 9, SEQ ID NO: 10, SEQ ID NO: 11 and SEQ ID NO: 13 or SEQ ID NO: 7, SEQ ID NO: 8, SEQ ID NO: 12 and SEQ ID NO: 13 or SEQ ID NO: 7, SEQ ID NO: 9, SEQ ID NO: 12 and SEQ ID NO: 13 or SEQ ID NO: 7, SEQ ID NO: 10, SEQ ID NO: 12 and SEQ ID NO: 13 or SEQ ID NO: 8, SEQ ID NO: 9, SEQ ID NO: 12 and SEQ ID NO: 13 or SEQ ID NO: 8, SEQ ID NO: 10, SEQ ID NO: 12 and SEQ ID NO: 13 or SEQ ID NO: 9, SEQ ID NO: 10, SEQ ID NO: 12 and SEQ ID NO: 13 or SEQ ID NO: 8, SEQ ID NO: 9, SEQ ID NO: 11 and SEQ ID NO: 13 or SEQ ID NO: 7, SEQ ID NO: 8, SEQ ID NO: 10, SEQ ID NO: 11 and SEQ ID NO: 13 or SEQ ID NO: 10, SEQ ID NO: 8, SEQ ID NO: 9, SEQ ID NO: 11 and SEQ ID NO: 13 or SEQ ID NO: 7, SEQ ID NO: 8, SEQ ID NO: 9, SEQ ID NO: 12 and SEQ ID NO: 13 or SEQ ID NO: 7, SEQ ID NO: 8, SEQ ID NO: 10, SEQ ID NO: 12 and SEQ ID NO: 13 or SEQ ID NO: 10, SEQ ID NO: 8, SEQ ID NO: 9, SEQ ID NO: 12 and SEQ ID NO: 13 or SEQ ID NO: 7, SEQ ID NO: 8, SEQ ID NO: 9, SEQ ID NO: 10, SEQ ID NO: 11, SEQ ID NO: 12 and SEQ ID NO: 13, at least one EBV specific antigen comprising a polypeptide of sequence SEQ ID NO: 16 and at least one H. pylori specific antigen comprising an H. pylori lysate, optionally H. pylori specific antigen further comprises polypeptides of sequence SEQ ID NO: 62 and SEQ ID NO: 63.

According to another embodiment, said infectious agent antigens comprise at least one HCV specific antigen comprising a polypeptide of sequence SEQ ID NO: 8 and optionally a polypeptide of sequence SEQ ID NO: 13 or a variant or a fragment thereof, at least one EBV specific antigen comprising a polypeptide of sequence SEQ ID NO: 16 and optionally an EBV lysate and/or a variant and/or a fragment thereof, and at least one H. pylori specific antigen comprising an H. pylori lysate and/or at least one polypeptide selected from the group consisting of SEQ ID NO: 62, SEQ ID NO: 63, a variant and a fragment thereof, preferably H. pylori specific antigen comprises an H. pylori lysate and/or a polypeptide comprising a sequence SEQ ID NO: 62.

According to another embodiment, said infectious agent antigens comprise a polypeptide of sequence SEQ ID NO: 8, a polypeptide of sequence SEQ ID NO: 16 and an H. pylori lysate or polypeptides of sequence SEQ ID NO: 8, SEQ ID NO: 16 and SEQ ID NO: 62 or polypeptides of sequence SEQ ID NO: 8, SEQ ID NO: 16 and SEQ ID NO: 63 or polypeptides of sequence SEQ ID NO: 8, SEQ ID NO: 13, SEQ ID NO: 16, SEQ ID NO: 62 and an H. pylori lysate or polypeptides of sequence SEQ ID NO: 8, SEQ ID NO: 13, SEQ ID NO: 16 and an H. pylori lysate or polypeptides of sequence SEQ ID NO: 8, SEQ ID NO: 13, SEQ ID NO: 16, SEQ ID NO: 62 and SEQ ID NO: 63 and an H. pylori lysate or polypeptides of sequence SEQ ID NO: 8, SEQ ID NO: 11, SEQ ID NO: 13, SEQ ID NO: 16 and an H. pylori lysate or polypeptides of sequence SEQ ID NO: 8, SEQ ID NO: 11, SEQ ID NO: 13, SEQ ID NO: 16 SEQ ID NO: 62, SEQ ID NO: 63 and an H. pylori lysate or polypeptides of sequence SEQ ID NO: 8, SEQ ID NO: 11, SEQ ID NO: 12, SEQ ID NO: 13, SEQ ID NO: 16 and an H. pylori lysate or polypeptides of sequence SEQ ID NO: 8, SEQ ID NO: 11, SEQ ID NO: 12, SEQ ID NO: 13, SEQ ID NO: 16, SEQ ID NO: 62, SEQ ID NO: 63 and an H. pylori lysate.

The protein microarray assay according to the invention may further comprise T. gondii, HSV1, HSV2 and VZV antigens.

As used herein the term "polypeptide" refers to any chain of amino acids linked by peptide bonds, regardless of length or post-translational modification. Polypeptides include natural proteins, synthetic or recombinant polypeptides and peptides (i.e. polypeptides of less than 50 amino acids) as well as hybrid, post-translationally modified polypeptides, and peptidomimetic.

As used herein, polypeptide or protein references in the format P13200 or A08CC061D2B4B792 for SEQ ID NO: 2 are Uniprot database references in which reference P13200 is the protein or polypeptide accession number (ACC) No) and reference A08CC061D2B4B792 is the Sequence Checksum (Checksum).

A polypeptide may be modified by natural processes, such as the post-translational maturation processes or by chemical processes which are well known to the person skilled in the art. The same type of modifications may be present at a plurality of locations on the polypeptide and anywhere within the polypeptide: in the peptide backbone, in the amino acid chain or even at the carboxy-terminal or amino-terminal ends. These types of modification may be the result of a natural or synthetic post-translational process, these processes being well known to the person skilled in the art.

Modification of a polypeptide may mean notably cationic or anionic modifications such as, for example, acetylation, acylation, ADP-ribosylation, amidation, covalent binding of flavin, covalent binding of a heme, covalent binding of a nucleotide or of a nucleotide derivative, covalent binding of a lipid or of a lipid derivative, covalent binding of a phosphatidylinositol, covalent or non-covalent cross linking, cyclisation, formation of a disulphide bond, demethylation, the formation of cysteine, the formation of pyroglutamate, formylation, gamma-carboxylation, glycosylation, the formation of a GPI anchor, hydroxylation, iodisation, methylation, myristoylation, oxidation, the proteolytic process, phosphorylation, prenylation, racemisation, seneloylation, sulphation, amino acid addition such as arginylation or ubiquitination (PROTEINS STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990) and Rattan et al., Protein Synthesis: Posttranslational Modifications and Aging, Ann. N.Y. Acad. Sci. 663:48-62 (1992)).

In one embodiment, the infectious agent antigen or the self antigen may be a modified polypeptide of a sequence selected from the group consisting of sequence SEQ ID NO: 1 to SEQ ID NO: 61. For example, the protein paratarg-7 (pP-7) which is a virus specific antigen according to the invention is naturally hyperphosphorylated. The hyperphosphorylated form of pP-7 is a particularly interesting virus specific antigen.

As used herein, the term "amino acid" refers to the 20 standard alpha-amino acids as well as naturally occurring and synthetic derivatives. A polypeptide may contain L or D amino acids or a combination thereof.

The term "variants" in "protein variants" includes naturally occurring variants, such as splice variants, alleles and isoforms, or they may be produced by recombinant means. Variations in amino acid sequence may be introduced by substitution, deletion or insertion of one or more codons into the nucleic acid sequence encoding the protein that results in a change in the amino acid sequence of the protein. Optionally the variation is by substitution of 1, 2, 3, 4, 5, 6, 7, 8, 9, 10, 11, 12, 13, 14, 15, 16, 17, 18, 19, 20 or more amino acids with any other amino acid in the protein. Amino acid substitutions may be conservative or non-conservative. Preferably, substitutions are conservative substitutions, in which one amino acid is substituted for another amino acid with similar structural and/or chemical properties. Additionally or alternatively, the variation may be by addition or deletion of 1, 2, 3, 4, 5, 6, 7, 8, 9, 10, 11, 12, 13, 14, 15, 16, 17, 18, 19, 20 or more amino acids within the protein.

Amino acid substitutions may be conservative or non-conservative. Preferably, substitutions are conservative substitutions, in which one amino acid is substituted for another amino acid with similar structural and/or chemical properties. Exemplary conservative substitutions are listed below.

Ala (A) val; leu; ile
Arg (R) lys; gin; asn
Asn (N) gln; his; lys
Asp (D) glu
Cys (C) ser
Gln (Q) asn
Glu (E) asp
Gly (G) pro; ala
His (H) asn; Gln; lys; arg
Ile (I) leu; val; met; ala;
Leu (L) norleucine; ile; met; ala; phe
Lys (K) arg; Gln; asn
Met (M) leu; phe; ile
Phe (F) leu; val; ile; ala; tyr
Pro (P) ala
Ser (S) thr
Thr (T) ser
Trp (W) tyr; phe
Tyr (Y) trp; phe; thr; ser
Val (V) ile; leu; met; phe; ala; norleucine Variant proteins may include proteins that have at least about 80% amino acid sequence identity with a polypeptide sequence disclosed herein. Preferably, a variant protein will have at least about 80%, 81%, 82%, 83%, 84%, 85%, 86%, 87%, 88%, 89%, 90%, 91%, 92%, 93%, 94%, 95%, 96%, 97%, 98%, 99% amino acid sequence identity to a full-length polypeptide sequence or a fragment of a polypeptide sequence as disclosed herein. Amino acid sequence identity is defined as the percentage of amino acid residues in the variant sequence that are identical with the amino acid residues in the reference sequence, after aligning the sequences and introducing gaps, if necessary, to achieve the maximum percent sequence identity, and not considering any conservative substitutions as part of the sequence identity. Sequence identity may be determined over the full length of the variant sequence, the full length of the reference sequence, or both. Methods for sequence alignment and determination of sequence identity are well known in the art, for example using publicly available computer software such as BioPerl, BLAST, BLAST-2, CS-BLAST, FASTA, ALIGN, ALIGN-2, LALIGN, Jaligner, matcher or Megalign (DNASTAR) software and alignment algorithms such as the Needleman-Wunsch and Smith-Waterman algorithms.

For example, the percentage identity may be calculated by performing a pairwise global alignment based on the Needleman-Wunsch alignment algorithm to find the optimum alignment (including gaps) of two sequences along their entire length, for instance using Needle, and using the BLOSUM62 matrix with a gap opening penalty of 10 and a gap extension penalty of 0.5.

Fragments of the proteins and variant proteins disclosed herein are also encompassed by the invention. Such fragments may be truncated at the N-terminus or C-terminus, or may lack internal residues, for example, when compared with a full length protein. Certain fragments lack amino acid residues that are not essential for enzymatic activity. Preferably, said fragments are at least about 10, 20, 30, 40, 50, 60, 70, 80, 90, 100, 110, 120, 150, 250, 300, 350, 400, 450, 500 or more amino acids in length.

In some embodiments, the infectious agent specific antigen may be an infectious agent lysate.

The term "lysate" in the expression "infectious agent lysate" refers to the cellular debris and fluid produced by lysis of infectious agent particles. According to the invention, said lysate may be obtained by lysis after purification of a sample of the infectious agent. Lysate may be obtained by using the infectious agent at any stage of its development. For example, *T. gondii* lysate may be Sporozoites, tachyzoites, or bradyzoites *T. gondii* lysate preferably a tachyzoites *T. gondii* lysate.

The protein microarray assay is performed by applying the biological sample to the substrate. Once the biological sample has been applied to the protein microarray, the microarray is incubated under conditions that allow for immunoglobulin in the sample to bind one or more antigen on the substrate. Incubation conditions will vary depending on the type of sample analyzed, its concentration and the detectable labels employed. Detection schemes are generally described in, for example, Haab et al Curr Opin Drug Discov Devel. 2001 January; 4(1):116-23., MacBeath et al. Nat Genet. 2002 December; 32 Suppl:526-32., and Kodadek, Chemistry & Biology, 8: 105-115 (2001)). Typically and preferably, all unbound compounds are washed off the microarray, leaving only bound compounds. The binding of a compound in the sample to an antigen on the substrate is visualized via methods including fluorescence, chemiluminescence, colorimetric, RLS, SPR and mass spectroscopy. To maximize the robustness and quantitative accuracy of the microarray, comparative detection measurements can be made, using an internal standard for each antigen to be assayed. In this respect, in the case of fluorescence detection, two differentially labeled solutions containing compounds of interest can be mixed together and then incubated with the microarray so that the fluorescence ratio at each spot on the microarray corresponds to the ratio of each compound in the two solutions (see, e.g., Haab et al., supra).

In one embodiment, the protein microarray assay is a quantitative protein microarray assay.

The biological sample according to the invention can be any suitable sample, but preferably is a sample obtained from a mammal (e.g., a human). The sample can be a solid sample, such as a tissue sample, or the sample can be fluid, such as a sample of body fluid. For instance, a section of whole tissue can be homogenized to liquefy the components found in the tissue. The tissue sample can be obtained from any suitable organ, including diseased organs (e.g., organs affected by cancer). Suitable fluid samples include, but are not limited to, blood, serum, plasma, lymph, urine, cerebrospinal fluid and, interstitial fluid. Biological sample may be purified monoclonal immunoglobulin from any suitable organ or fluid samples. For performing the protein microarray assay, different dilutions of the biological sample adjusted for monoclonal Ig concentration may be used. For example, an Ig concentration of 3, 4, 5, 6, 7, 8, 9, 10, 11, 12, 13, 14, 15, 16, 17, 18, 19, 20, 21, 22, 23, 24 g/L or more may be used, and/or an Ig concentration of 30, 29, 28, 27, 26, 25, 24, 23, 22, 21, 20, 19, 18, 17, 16, 15, 14, 13, 12, 11, 10, 9, 8, 7, 6, 5, 4, 3 g/L or less. Preferably, an Ig concentration of more than 3.5 g/L, 4 to 30 g/L, 7 to 25, 10 to 20 or 15 to 18 g/L is used.

Whatever biological sample is used, each of the one or more compounds in the sample preferably comprises a detectable label. The detectable label preferably is attached to each protein (notably each mc Ig) via covalent linkage to the amino groups on the proteins. Any suitable detectable label known in the art can be employed in the protein microarray. Preferably, the detectable label is a fluorescent dye, such as, for example, Cy5 (red fluorescence) and Cy3 (green fluorescence). The sample preferably is in a solution, and is applied to the protein microarray using methods described in the art. Methods for preparing protein samples for protein microarrays are described for example, in, Haab et al., supra.

The term "antibody" ("Ab") or "immunoglobulin" (Ig) is used herein in the broadest sense, and encompasses monoclonal, polyclonal or multispecific antibodies, minibodies, heteroconjugates, diabodies, triabodies, chimeric, antibodies and antibody fragments, or variants thereof that retain antigen binding activity. Antibodies are defined herein as retaining at least the ability to bind the antigen specifically.

In some embodiment, the immunoglobulins of the invention are native immunoglobulins. Native immunoglobulins are usually heterotetrameric glycoproteins of about 150,000 Daltons, typically composed of two identical light (L) chains and two identical heavy (H) chains. The heavy chain is approximately 50 kD in size, and the light chain is approximately 25 kDa. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains. The light chains of immunoglobulins from any vertebrate species can be assigned to one of two clearly distinct types, called kappa (.kappa.) and lambda (.lambda.), based on the amino acid sequences of their constant domains. The ratio of the two types of light chain varies from species to species. As a way of example, the average kappa chains to lambda chains ratio is 20:1 in mice, whereas in humans it is 2:1 and in cattle it is 1:20.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g. IgG1, IgG2, IgG3, IgG4, IgA, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "isotype" refers to the antibody class (for instance IgG1, IgG2, IgG3, IgG4, IgD, IgA, IgE, or IgM) that is encoded by heavy chain constant region genes. In a normal serum sample, immuglobulins levels are of 3-16 g/L for IgG; of 0.5-4 g/L for IgA and of 0.5-3 g/L for IgM.

Immunoglobulins are secreted by plasma cells and each plasma cell produces a single type of immunoglobulin. In monoclonal gammopathies, there is an expansion of a single plasma cell clone, and consequently an increase in the monoclonal immunoglobulin (mc Ig) produced by this clone.

In one embodiment, immunoglobulin is preferably a monoclonal immunoglobulin. The terms "monoclonal immunoglobulin", "mc Ig" or "monoclonal immunoglobulin composition" as used herein refer to a protein produced by clonally expanded Ig producing plasma cells. The presence of a mc Ig serves as a marker of the clonal proliferation of the plasma cells in the diagnostic for a monoclonal gammopathy. In addition, the disease course can be monitored by following the concentration of the mc Ig. Diagnosis of a monoclonal gammopathy may be carried out in a number of ways. Serum and urine protein electrophoresis (SPEP, UPEP) (see FIG. 6), immunofixation electrophoresis (IFE) and nephelometric or turbidimetric measurement of serum immunoglobulins remain the gold standard laboratory techniques for monitoring of monoclonal gammopathies. SPEP is the standard method for screening for mc Ig and is based upon scanning gels in which serum proteins have been separated, fixed and stained. The SPEP allows distinguishing 5 fractions according to the electric charge, respectively from anode to cathode: albumin, alpha-1 globulins, alpha-2 globulins, beta globulins and gamma globulins (see FIG. 6). The concentration of bands can be quantified by densitometry. By comparing the SPEP of a normal serum (FIG. 6A) to the serum of a patient having a monoclonal gammopathy (FIG. 6B), the SPEP of a patient having a monoclonal gammopathy is characterized by the presence of a spike due to the over-expression of the m Ig.

According to one embodiment, the mc Ig may be an immunoglobulin A, G or M.

Preferably, said mc Ig is a marker monoclonal immunoglobulin. According to the invention, a "marker monoclonal immunoglobulin" refers to the mc Ig which is a marker of a monoclonal gammopathy.

Monoclonal immunoglobulin purification may be performed by chromatographic methods for example Non-Affinity Chromatographic Methods such as hydrophobic interaction chromatography or affinity chromatography such as affinity Protein A chromatography or Immobilized Metal Affinity Chromatography (IMAC). Immunoglobulin purification may further be performed by any method providing a separation of proteins according to their molecular weight and/or their isoelectric point (pI) such as for example mono or bi-dimensional electrophoresis. The purification is performed using physico-chemical properties of Ig such as isoelectric point, molecular weight, or electric charge. Monoclonal immunoglobulin purification is a key step for studying mc Ig specificity because it is necessary to separate mc Ig from polyclonal Igs and other globulins (beta and alpha). In one embodiment, the technique employed is based on electric charge and allows mc Ig to be separated from polyclonal Igs, using agarose electrophoretic gels (SAS-MX Hi res kit Helena-Biosciences, Gateshead, NE11 0SD). After electrophoresis, only a part of the gel is stained using Coomassie brilliant Blue to allow visualization of mc Ig position. The part of the unstained agarose gel corresponding to mc Ig is cut and mc Ig is eluted passively into PBS buffer overnight with agitation. The purification step is controlled by performing Isoelectric focusing on purified mc Ig on agarose gel (range of Ph=3.5-10) then western blotting onto PVDF followed by immunodetection using Horseradish peroxidase labeled antibody against heavy Ig chain.

"Immunoglobulin concentration" of purified mc Ig samples may be measured by protein assay such as bovine serum albumin (BCA) assay (BC assay kit Optima) or by using specific methods such as immuno-nephelemetric assay onto Immage Beckman analyzer. The value of the mc Ig concentration permits the amount of mc Ig used on the MIP array to be adjusted. The purified mc Ig samples are used in the method of the invention at two concentrations. Preferably, the purified mc Ig samples are used at concentrations between 12.5 and 200 µg/ml. According to one embodiment, the first purified mc Ig sample concentration is between 20 and 30 µg/ml, the second purified mc Ig sample concentration is between 45 and 55 µg/ml. Typically, the purified mc Ig samples are used in the method of the invention at concentrations of 25 and 50 µg/ml.

The intensity of the fluorescence signal obtained via MIP of mc Ig specific for an infectious agent or for a self antigen can be compared with positive and negative controls to determine whether mc Ig specifically binds to the corresponding antigen. The increase or decrease of mc Ig fluorescence signal may be obtained by comparing the results of different samples provided from the same patient during treatment or follow-up (e.g. before and/or after therapy).

The term "control sample" includes any sample that would permit specific and non-specific binding of the monoclonal immunoglobulin tested to be distinguished. A control sample may be a sample containing tag sequences such as histidine or glutathione S-transferase (GST) tags or a sample containing diluents or buffers such as PBS and/or BSA. A control sample may further be a serum sample of a healthy patient.

The protein microarray of the invention is particularly useful in determining the specificity of monoclonal immunoglobulin in myeloma and MGUS, to stratify patients according to Ag-specificity of their mc Ig, to permit the development of personalized medicine in myeloma and MGUS.

Monoclonal gammopathy is a disorder caused by abnormal proliferation of a single clone of plasma cells. Monoclonal gammopathies may be present in a wide spectrum of diseases, that includes notably myeloma and monoclonal gammopathy of undetermined significance (MGUS).

Monoclonal Gammopathy of Undetermined Significance (MGUS) is defined by the presence of mc Ig below 30 g/L in plasma, plasma cells below 10% in bone marrow, and no clinical, or biological alterations. Most often the diagnosis is performed during a routine laboratory test (electrophoresis of serum sample). MGUS subjects are not treated, and a biological follow-up is performed once a year.

"Myeloma", "Multiple Myeloma" or "MM" is a malignant proliferation of plasma cells in the bone marrow>10%, the presence of mc Ig in concentration>30 g/L in plasma, and biological or clinical alterations such as kidney damage, osteoporosis, hypercalcemia, anemia, leucopenia. Diagnosis is made when bone marrow analysis shows more than 10% of plasma cells. The treatment is intensive using different chemotherapic drugs, and for subsets of patients may include bone marrow graft. The life expectancy is still short for most patients (median: 5 years).

The array of the invention may be a single step assay, which may be used to simultaneously test serum and purified monoclonal immunoglobulin of patients for reactivity to numerous self antigens and germs known to cause chronic infection. The protein array according to the invention is as sensitive as the current techniques used to detect chronic infection in plasma and it is the only assay permitting simultaneous detection of specific immunoglobulins on very small samples and particularly on purified mc Ig. Use of the protein microarray of the invention proved considerably more efficient for studies of mc Ig specificity than phage display, epitope reconstruction or epitope mediated antigen prediction (E-MAP), which all proved disappointing. Consequently, the methods and arrays of the invention permit the monoclonal immunoglobulin specificity of subsets of MGUS and myeloma patients at the time of diagnosis to be determined and also to follow-up the patients including monitoring the response of patients to treatment. The methods and arrays of the invention facilitate personalized medicine in myeloma and MGUS and are useful for patient diagnosis and monitoring.

The invention further provides a method of analyzing interactions between an antigen and a monoclonal immunoglobulin of a MGUS or a myeloma patient. The method comprises (a) producing a protein microarray as described herein, (b) contacting the protein microarray with a sample comprising serum patients and purified monoclonal immunoglobulin, and (c) detecting binding of the one or more immunoglobulin with one or more of the antigen immobilized on the protein microarray.

It will be appreciated that the method for analyzing interactions between an antigen and an immunoglobulin is used to identify mc Ig that interact with the antigen of interest present on the substrate. In this manner, the inventive method can be employed to elucidate antibody specificity toward infectious agent antigens or self antigen.

As used herein, the term "specificity" or similar terms, used in the context of an antibody regarding to its target, refers to the antibody specifically binding to the target antigen (as opposed to other antigens). An antibody which "specifically binds" to a target protein binds to said target protein with greater affinity and/or avidity that to other proteins or epitopes, even closely related proteins or epitopes. Preferably, an antibody of the invention binds to infectious agent specific antigens as described herein, such as polypeptides comprising or consisting of the sequence of SEQ ID No 1 to 61 with greater affinity and/or avidity than it binds to other proteins. Typically, the antibody binds with an affinity corresponding to a $K_D$ of about $10^7$ M or less, such as about $10^8$ M or less, such as about $10^9$ M or less, about $10^{10}$ M or less, or about $10^{11}$ M or even less when determined by surface plasmon resonance (SPR) technology in a BIAcore 3000 instrument using recombinant CD38 as the ligand and the antibody as the analyte. The antibody may bind to the target with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g. BSA, casein). The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold. The phrases "an antibody recognizing an antigen" and "an antibody specific for an antigen" are used interchangeably herein with the term "an antigen binding peptide which binds specifically to an antigen". Likewise, the phrases "an antibody recognizing an antigen" and "an antibody specific for an antigen" are used interchangeably herein with the term "an antibody which binds specifically to an antigen".

The invention further provides a method for determining whether a Monoclonal Gammopathy of Undetermined Significance (MGUS) or Myeloma patient carries mc Ig which is specific for an infectious agent or for a self antigen, wherein said method comprises a protein microarray assay comprising the steps of:
  a) incubating a biological sample of the MGUS or myeloma patient with a protein microarray comprising (a) a substrate, (b) antigens immobilized on the substrate, said antigens comprise at least one infectious agent antigen and/or at least one self-antigen,
  b) detecting if said mc Ig is bound to said antigen(s), preferably detecting if purified mc Ig is bound to said antigen(s).

The invention further provides a method for determining whether a Monoclonal Gammopathy of Undetermined Significance (MGUS) or Myeloma patient carries a marker mc Ig which is specific for an infectious agent or for a self antigen, wherein said method comprises a protein microarray assay comprising the steps of:
  a) incubating a biological sample of the MGUS or myeloma patient with a protein microarray comprising (a) a substrate, (b) antigens immobilized on the substrate, said antigens comprise infectious agent antigens and/or self-antigens,
  b) detecting if said marker mc Ig is bound to said antigens, preferably detecting if said purified marker mc Ig is bound to said antigens
wherein said marker mc Ig is identifiable as a spike of immunoglobulins by electrophoresis of said patient serum or serum-containing fluid or patient urine or urine-containing fluid.

The detection of mc Ig is provided as described herein, by using for example fluorescence, chemiluminescence, colorimetric, RLS, SPR or mass spectroscopy.

According to the method of the invention, the mc Ig detected as bound to at least one infectious agent or self antigens, are specific for said antigen tested.

The method according to the invention may comprise determining the concentration of mc Ig specific for an infectious agent or for a self antigen, for example by detecting specific binding of said mc Ig in said patient at different moment of time during the therapy or before or after therapy or by comparison with a control sample.

The invention also provides use of a protein microarray for characterizing mc Ig specificity of a Monoclonal Gammopathy of Undetermined Significance (MGUS) or Myeloma patient wherein said protein microarray comprises (a) a substrate, (b) antigens immobilized on said substrate, wherein said antigens comprise infectious agent antigens which comprise at least one HCV specific antigen, at least one EBV specific antigen and at least one *H. pylori* specific antigen.

MGUS may be diagnosed by performing serum protein electrophoresis showing a monoclonal peak in beta or gamma globulin zone.

However, current methods of diagnosis of MGUS do not provide information concerning the potential of evolution of MGUS to myeloma nor concerning mc Ig specificity.

Thus, the invention further provides a method of prognosing the outcome of myeloma in a patient or the potential risk of a MGUS patient to have a myeloma, wherein said method comprising the step of determining whether a mc Ig of said patient is specific for an infectious agent or for a self antigen using the method according to the invention, said method optionally comprising the step of determining the concentration of said mc Ig and its specificity for an infectious agent or a self and/or comparing the fluorescence signal intensity of said specific mc Ig to a control sample. According to one embodiment, the detection of mc Ig directed against at least one infectious or self antigen should be indicative of an increased likelihood of progression of MGUS to myeloma and/or a poor prognosis of survival. Curative treatment for various chronic infections being known, the detection of mc Ig directed against at least one infectious agent would be indicative of a chronic infection and thus of a good prognosis of treating the MGUS or of increased likelihood of patient survival after treatment of said chronic infection.

Also provided is a method of monitoring the response to a therapy of a myeloma patient or a MGUS patient or of diagnosing an MGUS or of diagnosing a myeloma relapse or of diagnosing therapy-refractory myeloma or MGUS, said method comprising determining whether a mc Ig of said patient is specific for an infectious agent or for a self antigen using the method according to the invention, wherein said method optionally comprises the step of determining the specificity of said mc Ig for an infectious agent or a self antigen and/or comparing the fluorescence signal intensity of said specific mc Ig to a control sample. According to one embodiment, the detection of mc Ig directed against at least one self antigen or infectious agent, or detection of an increase of the signal obtained on the MIP array of said mc Igs is indicative of therapy-refractory myeloma or of a myeloma relapse.

The term "relapse" in the expression "myeloma relapse" refers to the recurrence of myeloma disorder after recovery following therapy; and or recurrence of one or more symptoms (e.g., elevation of blood concentration of mc Ig, increase of plasma cells in bone marrow, kidney damage, high concentration of beta2 microglobulin) associated with a myeloma disorder after recovery following therapy.

Reference to "therapy-refractory" myeloma indicates that said—myeloma is refractory to a therapy or therapies conventionally used to treat said conditions. The term "Refractory" refers to the resistance or non-responsiveness of a disease or condition to a treatment or to any previous treatment. A therapy-refractory myeloma means that at least some significant portion of the symptoms associated with said myeloma or (e.g., high blood concentration of mc Ig more than 3.0 g/dL) are not eliminated or lessened by that therapy.

Also is provided a method for monitoring or designing a treatment regimen for a MGUS or myeloma patient, comprising determining whether a MGUS or myeloma patient carries a mc Ig specific for an infectious agent or for a self antigen as described herein.

The invention also concerns a method for treating a MGUS or improving treatment of myeloma patient or preventing myeloma in a patient having a MGUS comprising (a) the method of determining whether the mc Ig of a patient is specific for an infectious agent or for a self antigen according to the invention and (b) the step of treating the patient with an immunosuppressive drug or an anti-infectious agent drug.

In the context of the invention, the term "treating" or "treatment" means reversing, alleviating, inhibiting the progress of, or preventing the disorder or condition to which such term applies, or one or more symptoms of such disorder or condition. In particular, the treatment of the disorder may consist in inhibiting the progression of the MGUS or myeloma. More preferably, such treatment leads to the total eradication of the MGUS or the myeloma.

The term "diagnosis" is used herein to refer to the identification of a molecular or pathological state, disease or condition, such as the identification of MGUS or the myeloma or to refer to identification of a patient suffering from MGUS or the myeloma who may benefit from a particular treatment regimen.

The term "prognosis" is used herein to refer to the prediction of the likelihood of benefit from therapy. The term "prediction" or "predicting" refers to the likelihood that a patient will respond either favourably or unfavourably to a particular therapy. In one embodiment, prediction or predicting relates to the extent of those responses. In one embodiment, the prediction or predicting relates to whether and/or the probability that a patient will develop MGUS or myeloma following treatment, for example treatment with a particular therapeutic agent, and for a certain period of time without disease recurrence. The predictive methods of the invention can be used clinically to make treatment decisions by choosing the most appropriate treatment modalities for any particular patient. The predictive methods of the present invention are valuable tools in predicting if a patient is likely to respond favourably to a treatment regimen, such as a given therapeutic regimen (anti-viral or anti-biotic drugs), or whether the patient having MGUS will develop myeloma following a therapeutic regimen is likely.

In the context of the present invention, the individual or patient is mammal preferably is a human individual.

The term "anti-infectious agent drugs" means any compounds that reduces or eradicates infection by neutralizing, blocking, inhibiting, abrogating, reducing or interfering with microorganism growth, metabolism or ability to infects its host, preferably the anti-infectious agent drugs is antiviral such as ribavirine or pegylated interferon in VHC treatment or antibiotic drugs such as clarythromycine in treatment of *H. pylori*.

The term "anti-autoimmune drug" means any compound that inhibits or suppress the onset of autoimmune diseases or the action to retard the onset thereof or any compound that ameliorates symptoms after the onset of autoimmune diseases, and the action to cure the disease such as corticosteroids or immunosuppressive agents.

The methods of the invention are preferably ex vivo or in vitro methods.

Although having distinct meanings, the terms "comprising", "having", "containing' and "consisting of" may be replaced with one another throughout the above description of the invention.

In the frame of the present description, all compounds, polypeptides and monoclonal immunoglobulin may optionally be isolated and/or purified.

BRIEF DESCRIPTION OF THE DRAWING(S)

FIG. 1 is a diagram illustrating the "EBV/CMV/*T. gondii*/HCV protein microarray according to the invention. Each antigen or lysates was spotted in four replicates. Tag controls (His, GST), and negative controls (BSA, PBS) are used to validate the specificity of the IgG detection. Concentrations of antigens: EBNA (8 µM), VCA C1 (8 µM), VCA C2 (32 µM); Core, NS-3 and NS-4 (16 µM); Mix 5Ag for CMV (16 µM); p24 (12 µM). Lysate were printed at C1 (200 µg/m L) and C2 (400 µg/mL).

Figure 2:
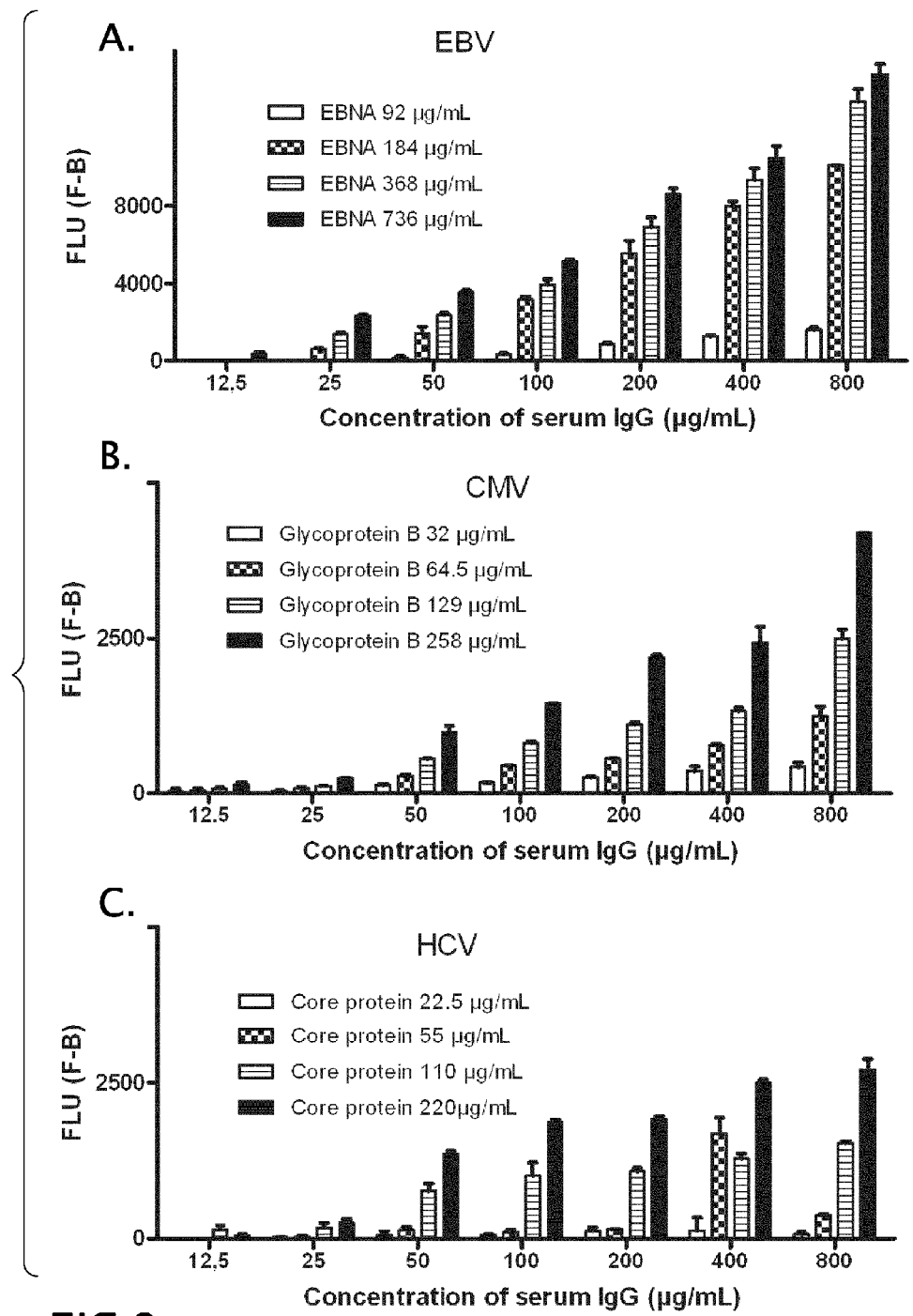

FIG. 2 illustrates the fluorescence minus background noise (FLU (F-B)) collected from single antigen arrays: EBV-EBNA (FIG. 2A), CMV-glycoprotein (FIG. 2B), HCV-core (FIG. 2C). For each germ, serum dilutions of a patient found positive for the germ by ELISA were tested on a single antigen array. The median fluorescence intensity minus background noise (FLU (F-B)) was, collected at different concentrations of antigens (32-258 µg/mL (1-8 µM) for glycoprotein B of CMV, and 92-736 µg/mL (2-16 µM) for EBV-EBNA and 22.5-220 µg/mL (2-16 µM) for HCV-core) for different quantities of hybridized IgG (12.5-800 µg/mL). Positive and negative results obtained with patient sera tested for EBV (n=42), CMV (n=44) and HCV (n=60) are shown.

Figure 3:
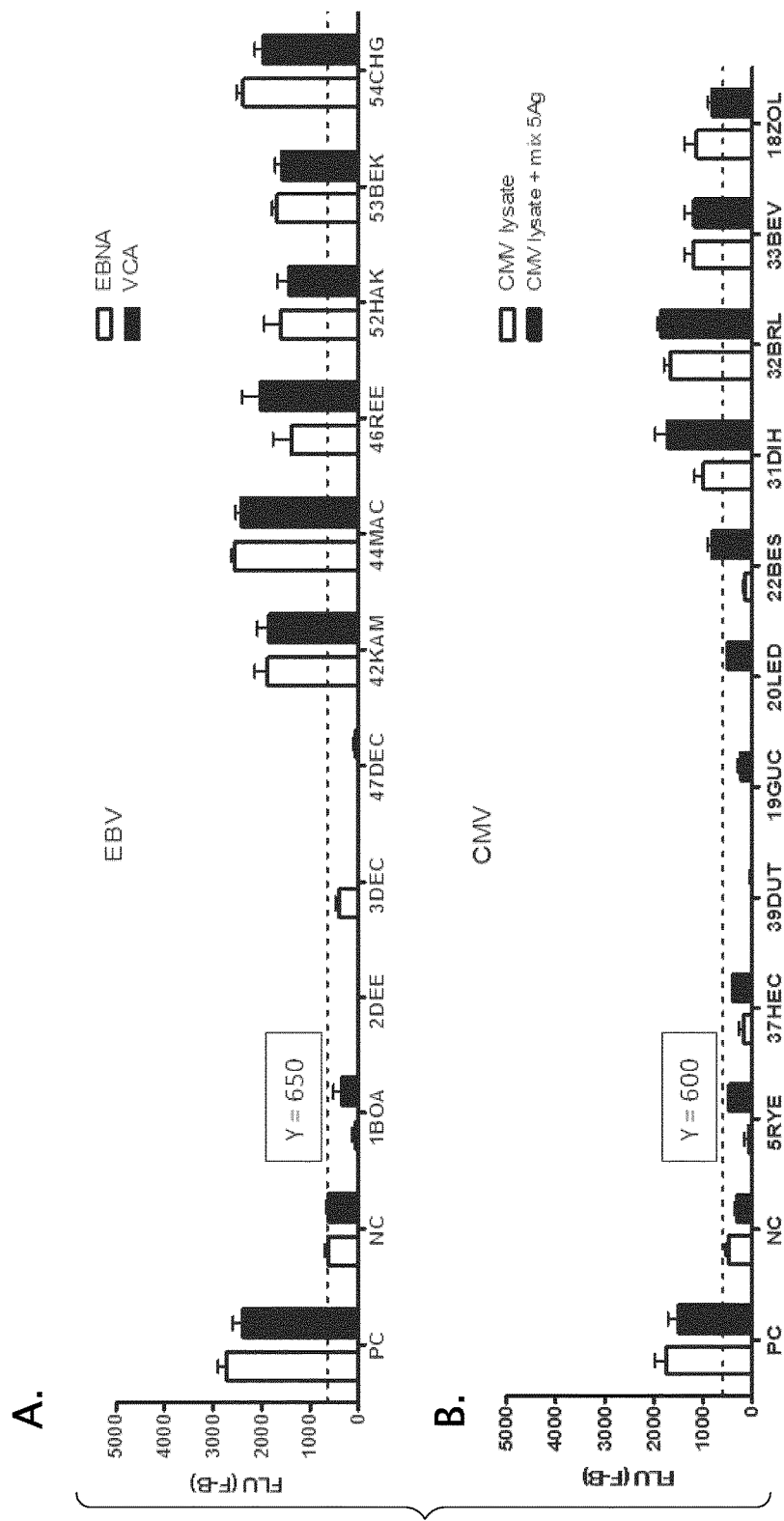
Figure 4:
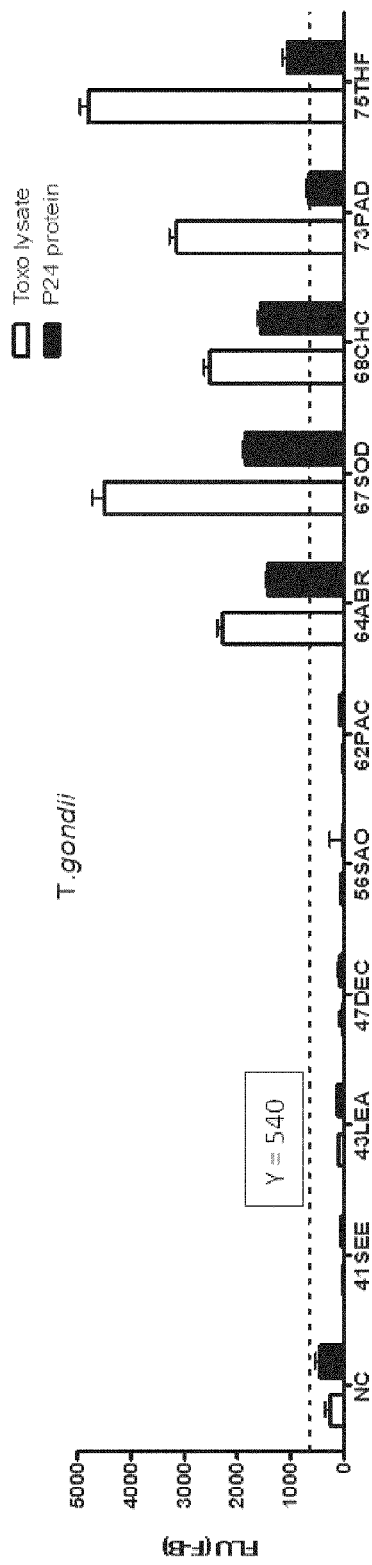
Figure 5:
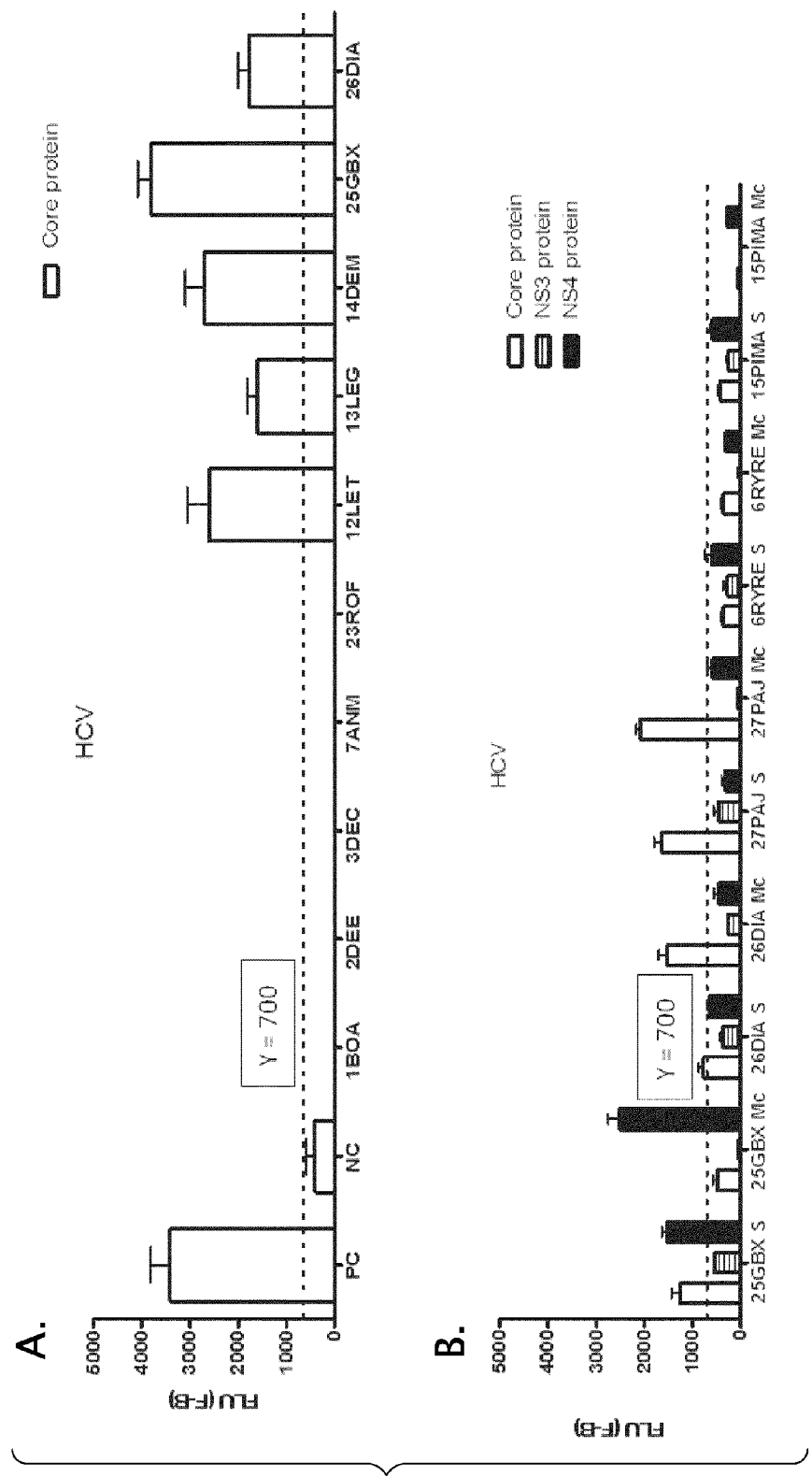

FIGS. 3 to 5 illustrates the fluorescence minus background noise (FLU (F-B)) collected from the multiplexed infectious protein (MIP) microarray. The MIP microarray used carried several antigens from EBV (FIG. 3A), CMV (FIG. 3B), *T. gondii* (FIG. 4) and HCV (FIGS. 5A and 5B). Results obtained for each germ are shown separately in FIGS. 3 to 5. The data show results obtained for 10 patients: patients were selected with serum found negative for EBV (n=4), CMV (n=5) and *T. gondii* (n=5), and patients with serum found positive for EBV (n=6), CMV (n=5) and *T. gondii*. (n=5). The threshold of significant fluorescence was determined for each germ using the negative control. Graphs represent the median fluorescence intensity minus background noise (FLU (F-B)) collected from the arrayed antigens: EBV (FIG. 3A), CMV (FIG. 3B), *T. gondii* (FIG. 4) and HCV (FIGS. 5A and 5B). PC: Positive control, NC: Negative Control. Then the MIP microarray was tested for monoclonal immunoglobulin (5th and last figure). For these studies we selected two patients with serum found negative for HCV, and three patients with serum found positive for HCV. Both sera and purified monoclonal immunoglobulin were analyzed on the same slide. The threshold of significant fluorescence was determined for each germ using the negative control. Graphs represent the median fluorescence intensity minus background noise (FLU (F-B)) obtained for core NS-3 and NS-4 antigens from HCV. S: serum, mc: monoclonal immunoglobulin.

Figure 6:
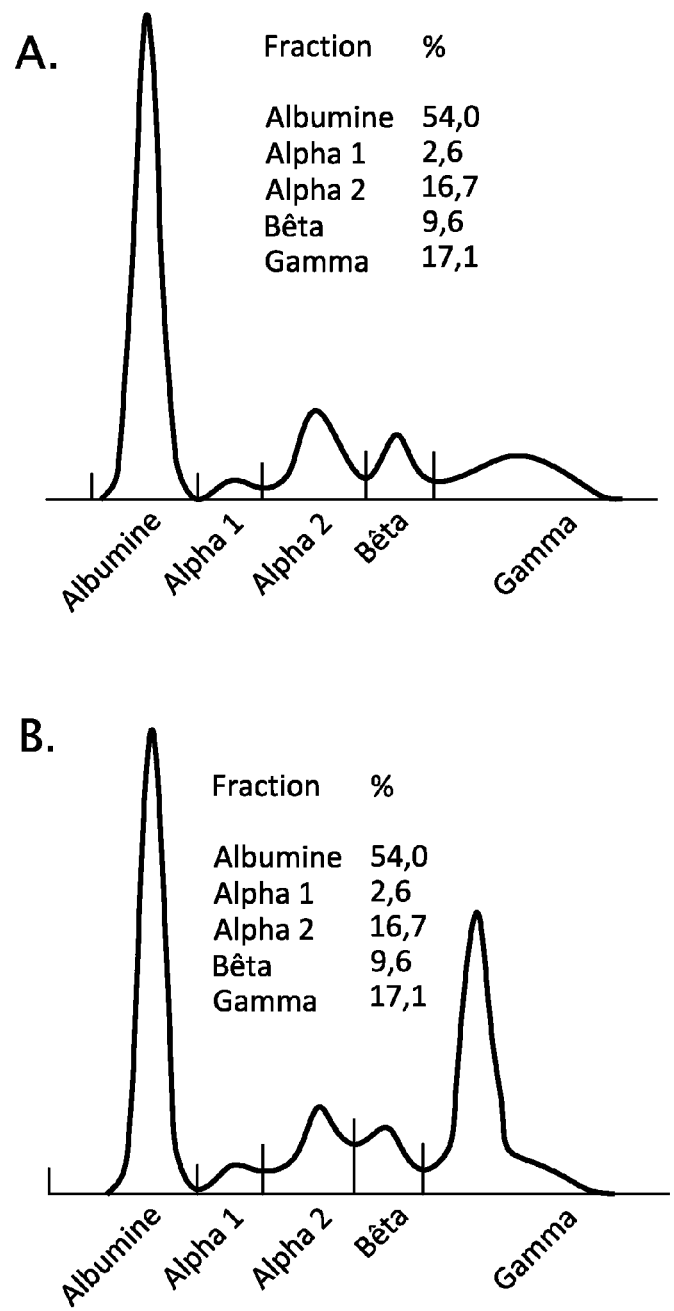

FIG. 6 illustrates serum protein electrophoresis: (A): serum without spike in the gamma-globulins zone (B): serum with a monoclonal spike in the gamma-globulins zone.

Figure 7:
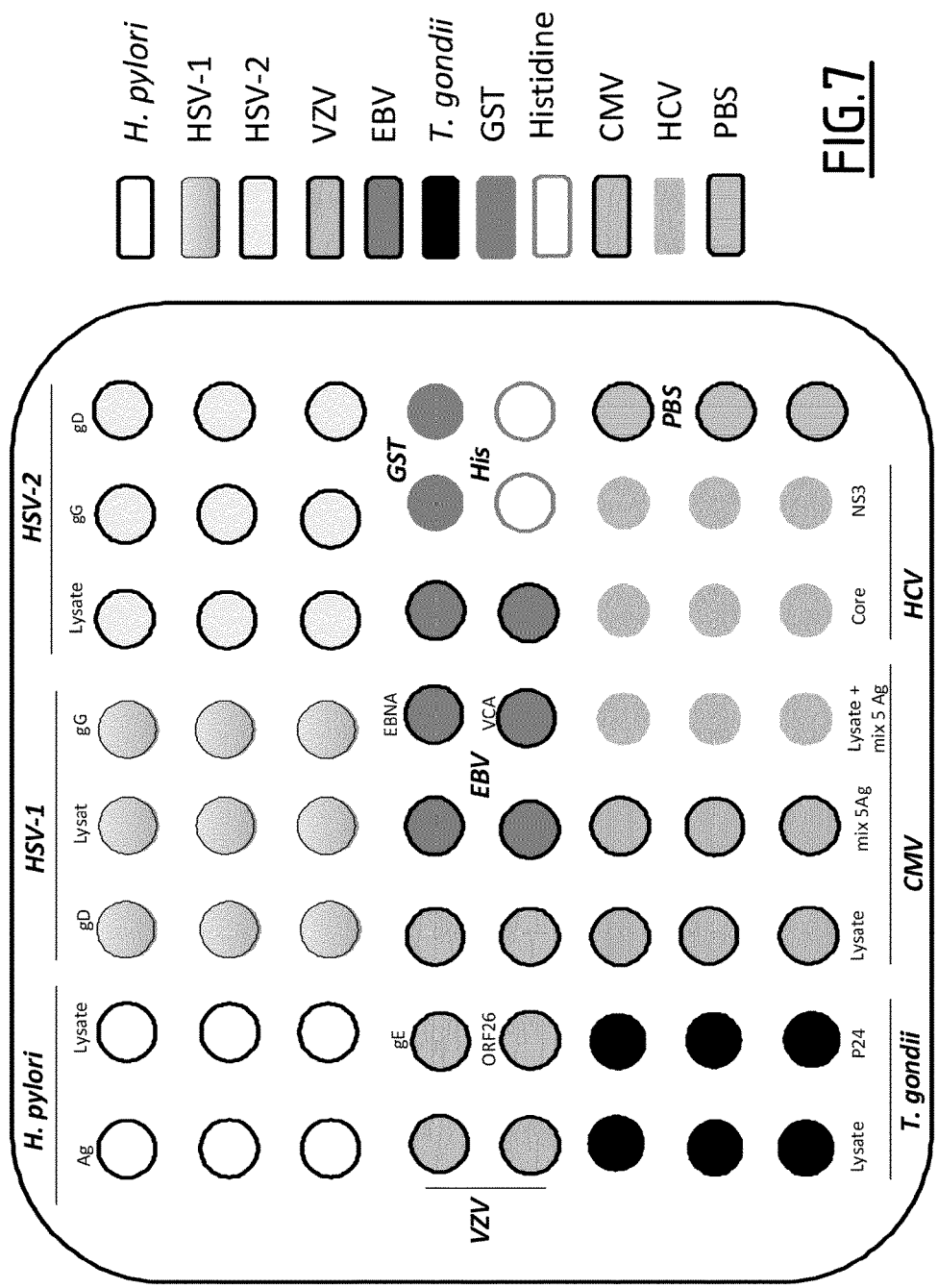

FIG. 7 is a diagram illustrating the "8-germs MIP microarray" according to the invention. Each antigen or lysates was spotted in three replicates. Tag controls (His, GST), and negative controls (PBS) are used to validate the specificity of the mc Ig detection. Concentrations of antigens: *H. pylori* Ag (500 µg/mL), *H. pylori* lysate (500 µg/mL), HSV-1 gD (12 µM), HSV-1 lysate (130 µg/mL), HSV-1 gG (12 µM), HSV-2 lysate (150 µg/mL), HSV-2 gG (16 µM), HSV-2 gD (14 µM), VZV gE (14 µM), VZV ORF 26 (16 µM), EBNA (8 µM), VCA (10 µM), *T. gondii* lysate (200 µg/mL), *T. gondii* p24 (12 µM), CMV lysate (400 µg/mL), mix 5Ag for CMV (16 µM), HCV Core (16 µM), HCV NS-3 (16 µM).

Figure 8:
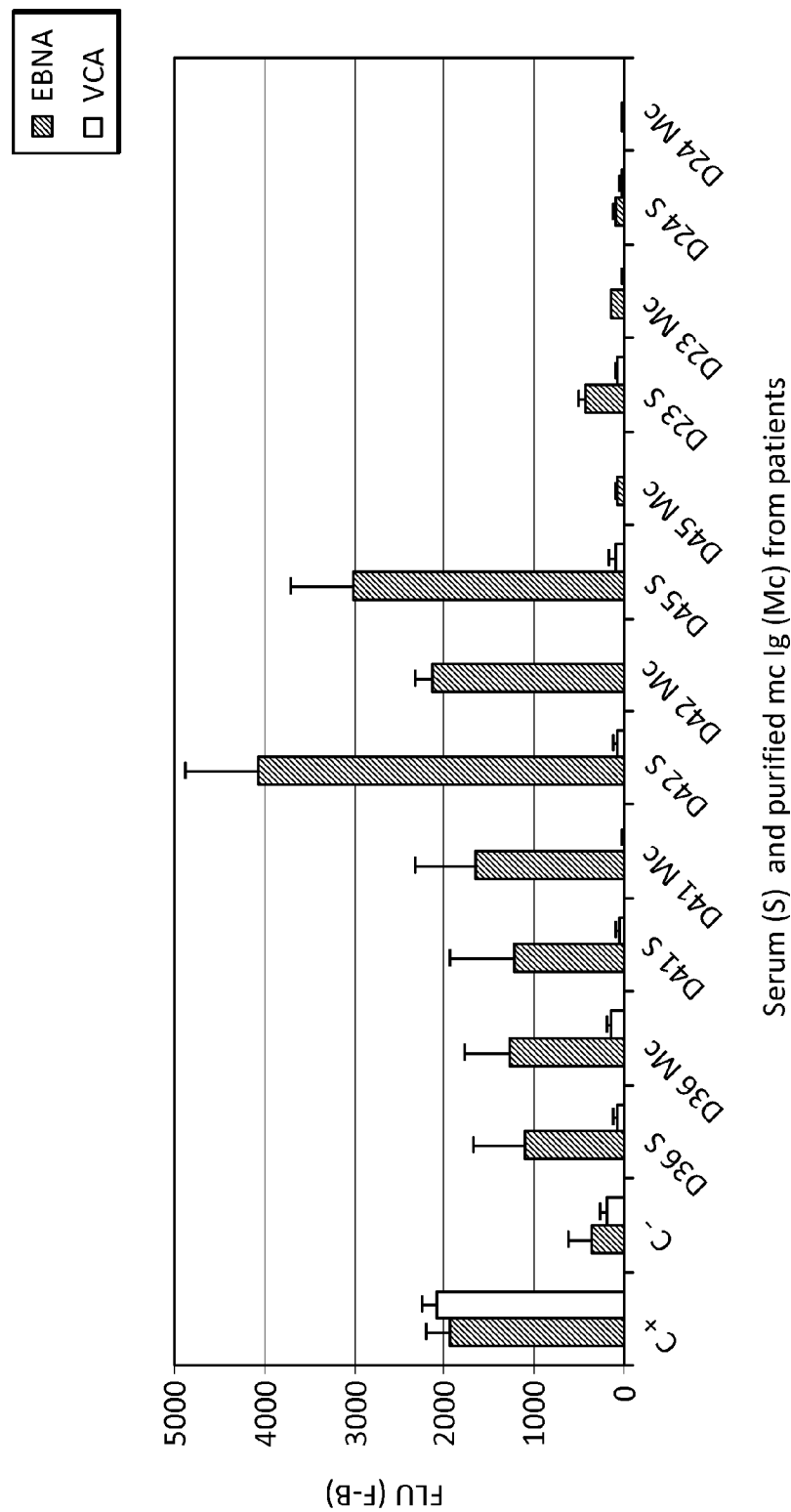

FIG. 8 illustrates the median fluorescence intensity minus background noise [FLU (F-B)] collected from the arrayed antigens: (A): The results shown were obtained with sera from 4 patients found positive for EBV (D36, D41 D42 and D45) and 2 patients with serum found negative for EBV (D23 and D24). Purified mc Ig from patients D36, D41 and D42 specifically recognize EBNA. Negative control (C−), positive control (C+), Sera (S) and purified mc Ig (Mc) were analysed on the same slide. The threshold of significant fluorescence was determined using the negative control.

Figure 9:
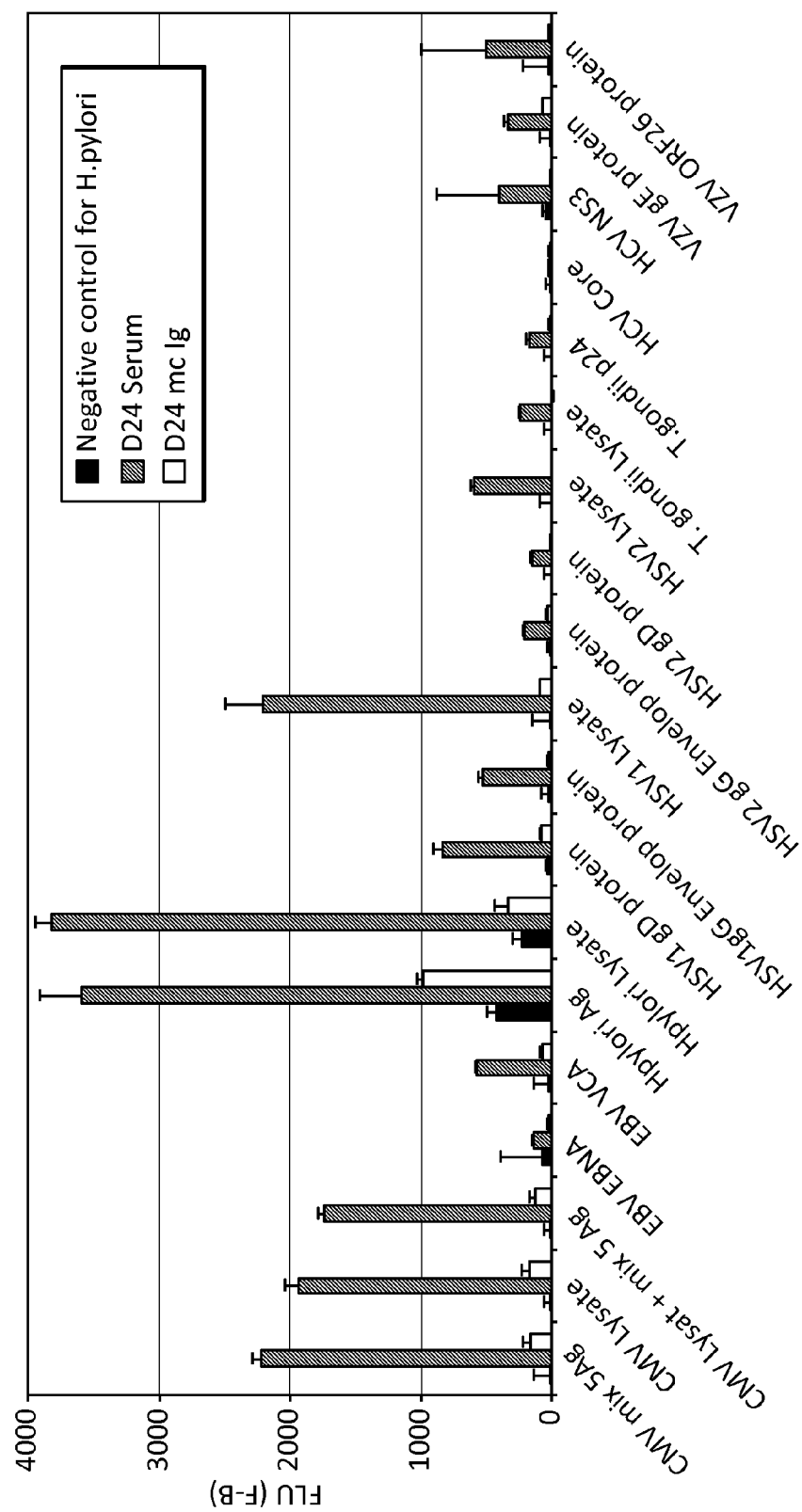

FIG. 9 illustrates the median fluorescence intensity minus background noise [FLU (F-B)] collected from the arrayed antigens: The results shown were obtained with serum from a patient (D24) found positive for *H. pylori*. Sera and purified mc Ig were analysed on the same slide. The threshold of significant fluorescence was determined using the negative control (C−).

EXAMPLES

Example 1

A/ Patients and Methods

Serum Samples

The study was performed on a panel of 70 human sera obtained from a heterogeneous group constituted of a majority of hospitalized patients and a few outpatients, including 34 women and 36 men, of age ranging from 7 to 73 (49.3±11.9) years and for whom one or several serological analyses had been prescribed. With consent, samples of venous blood were collected without anticoagulant. After coagulation, blood samples were centrifuged at 3500 rpm for 15 minutes at 4° C. and sera were collected and stored at −20° C. until analysis. The sera were provided by laboratories of the University Hospital of Nantes (Virology, Bacteriology and Parasitology laboratories).

Determination of Serological Status

Serological status for one or several pathogens including EBV, CMV, HCV and *T. gondii* was determined using classical ELISAs, as described below.

HCV:

HCV serological status was determined by chemiluminescent ELISA immunoassay on an Architect Abbott analyzer using the Abbott anti-HCV kit (ref. 6C37). This assay detects antibodies directed against structural and non-structural proteins of HCV using the following antigens: HCr 43, composed of the products of two non-contiguous coding regions of the HCV genome, amino-acids (aa) 1192 to 1457 from the NS-3 sequence and aa 1-150 from the HCV core sequence; C-100-3, a chimeric fusion protein with a part of human superoxiydase dismutase (h-SOD) and aa 1569-1931 of the NS-3 and NS-4 sequences.

CMV:

CMV serological status was determined by quantitative sandwich chemiluminescent immunoassay on a Diasorin Liaison analyzer using the Liaison®CMV IgG kit (ref. 310740). This assay detects antibodies directed against human CMV by using magnetic particles coated with inactivated human CMV (type AD169). The second antibody is a monoclonal mouse antibody directed against anti-human IgG, conjugated with isoluminol.

EBV:

EBV serological status was determined by quantitative sandwich chemiluminescent immunoassay on a Diasorin Liaison analyzer using the Liaison®EBNA IgG kit (ref. 310520) and Liasion® VCA IgG kit (ref. 310510) on a Diasorin Liaison analyzer. These assays detect antibodies directed against EBV nuclear antigen (EBNA) by using magnetic particles coated with synthetic peptide EBNA-1, or against the viral capsid antigen (VCA) by using magnetic particles coated with synthetic VCA peptide p18. The second antibody is a monoclonal mouse antibody against anti-human IgG conjugated with isoluminol.

*T. gondii:*

Determination of serological status against *T. gondii* was performed using quantitative ELISA on AxSYM System from Abbott. This assay detects IgG directed against the whole tachyzoïte *T. gondii* using coated microparticles; the main antigen is represented by *T. gondii* membrane protein p30. The secondary antibody is an anti-human IgG alkaline phosphatase conjugate; revelation is done by addition of 4-methylumbelliferyl phosphate.

Determination of IgG Concentration

The IgG concentration of each serum sample was determined with an immuno-nephelometric assay performed on a Beckman Immage Analyser. Then for each serum, IgG concentrations were adjusted from 12.5 to 800 µg/mL in PBS with 1% bovine serum albumin (BSA) and 0.1% Tween 20 (T-PBS) for further use on protein microarray (80 µL per incubation pad). Purification of mc Ig G from MGUS and myeloma patients was performed separating monoclonal Igs from polyclonal Igs and beta globulins by electric charge, using electrophoresis on agarose gels (kit Paragon SPE-II; Beckman Coulter, Villepinte, France). A portion of the agarose gel is stained using Coomassie Brilliant Blue and bands corresponding to monoclonal (apparent MW, pI) or polyclonal Igs (MW, pI) are then cut on the unstained portion of the agarose gel and proteins are eluted from gels into PBS. Purity may be verified using immunofixation (SAS-MX; Helena Biosciences, Gateshead, United Kingdom) or/and isoelectrofocusing and immunoblotting. IgG concentrations in eluates of purified monoclonal immunoglobulin were determined using the same immuno-nephelemetric assay as for serum. Tween 20 0.1% (TPBS) prior to hybridization onto the microarray.

Design of the Multiplexed Protein Microarray

Selected Antigens and Lysates

Antigens were supplied by Abcam (Cambridge, United Kingdom), Advanced Biotechnologies Inc. (Columbia, Md., USA) and Virogen (Watertown, Mass., USA). Lysates were supplied by Advanced Biotechnologies Inc. (Columbia, Md., USA).

For EBV the three Ag used were: Viral Capsid Antigen (VCA) p23 (sequence SEQ ID NO: 15; ref. ab43145, Abcam), p23 region 1-162aa (ref. 00211-V, Virogen) and Epstein-Barr Nuclear Antigen (EBNA) recombinant protein EBNA-1 of sequence SEQ ID NO: 16 (ref. 10-523-001, Advanced Biotechnologies).

For CMV, a mixture of five antigens was used: region 297-510 of Cytomegalovirus pp65 IE having the sequence SEQ ID NO: 60 (ref. ab54103, Abcam); immunodominant region of CMV pp28 (UL99; SEQ ID NO: 2) (ref. ab43038, Abcam); immunodominant region of CMV pp52 (UL44; sequence SEQ ID NO: 3) (ref. ab43044, Abcam); immunodominant region of glycoprotein B (SEQ ID NO: 4) (ref. ab43040, Abcam); and immunodominant region of CMV pp38 (UL80a; SEQ ID NO: 5) (ref. ab73042, Abcam) as well as a purified viral lysate (ref. 10-144-000, Advanced Biotechnologies).

For *T. gondii*, one antigen was used e.i. p24 (GRA1) protein of sequence SEQ ID NO: 6 (ref. ab43137, Abcam) and a purified trachyzoites lysate (ref. 10-279-001, Advanced Biotechnologies).

For HCV, three antigens were used: core protein composed of 119 aa (1-119) having the sequence SEQ ID NO: 8 (ref. ab49015, Abcam); NS-3 protein recombinant fragment subtype 1c (1192-1459 aa) (ref. ab91395, Abcam, SEQ ID NO 11) and NS-4 recombinant mosaic protein containing the HCV NS-4 immunodominant regions 1691-1710 aa, 1712-1733 aa, 1921-1940 aa from 1, 2, 3, 5 genotypes (SEQ ID NO: 13; ref. ab49027, Abcam). Some antigens contain histidine-tag or glutathione S-transferase (GST) fusion proteins.

Before being printed, the adequate concentration range of each antigen and lysate was determined. For this purpose, antigens were diluted in PBS from 1 to 16 µM, and lysates were diluted from 10 to 400 µg/mL. Lysates were ultrasonicated prior to dilution to avoid aggregates.

Preparation of the MIP Microarray

Antigen (10 µL, 1-16 µM) or lysate (10 µL, 10-400 µg/mL) solutions were pipetted in 384-well microtiter plates (PDC 90 Porvair Sciences Ltd., Shepperton, United Kingdom). Then, samples were transferred onto FAST slides 16 pad of nitrocellulose (Whatman, Maidstone, United Kingdom) using the sciFLEXARRAYER S3 Piezo Electric Dispenser (Scienion, Berlin—Germany). In all cases 6 drops were printed; each drop is estimated to contain 500 µL. Antigens, tag, fusion proteins and negative controls were also spotted.

As shown in FIG. 1, the arrays consisted of 8×8 matrices that included: (i) seven Ag: 3 for EBV, 3 for HCV, 1 for *T. gondii*; (ii) two lysates (CMV, *T. gondii*) in two concentrations; (iii) mix of CMV lysates and five Ag; (iv) two tag controls (GST, histidine); (v) two negative controls (PBS, BSA). Spotting was performed inside a chamber at 25° C. and 60% humidity. FIG. 1 shows the design of the microarray, and the concentrations of antigens, lysates and CMV mix.

Processing of Microarray Slides

Printed slides were saturated for 1 hour at room temperature with TPBS and 5% BSA in order to prevent non specific antibody binding. After washing with TPBS, slides were incubated with 80 µl of diluted serum or purified monoclonal immunoglobulin (12.5 to 800 µg/mL), for two hours at room temperature. After a second washing, slides were incubated with a labelled secondary antibody (0.1 to 4 µg/mL, Dylight™ 680 Labelled Goat anti-human IgG (H+L), from Kirkegaard & Perry Laboratories, Inc., Gaithersburg, Md., USA) while shaking in the dark, then washed with TPBS. The testing of each serum and monoclonal immunoglobulin was repeated at least three times. Fluorescence signal, detected with the Odyssey infrared imaging system scanner at 21 µm resolution (LI-COR Biosciences, NE, USA), was used to determine the serological status of each sample.

Data Analysis

Specific fluorescence was quantified using the GenePix® Pro 4 Microarray Acquisition & Analysis Software (Molecular Devices, Sunnyvale, Calif., USA). For each sample, the median fluorescence intensity (FLU) was determined after subtraction of background slide fluorescence. The intensity of each spot was analysed and the ratio of fluorescence minus background was calculated. Results for each sample (patients and controls) were represented on histograms using GraphPad 5.0 software (San Diego, Calif., USA). FLU values represent the mean of four replicates from one experiment. Experiments were repeated three times on different arrays for each patient FLU values obtained for each sample were compared to positive and negative controls for each germ. For each antigen, a positivity threshold was determined, that corresponds to a level of fluorescence above all negative controls. Patients for whom the mean FLU value was higher than the positivity threshold were considered positive for the antigen tested. When several antigens were used for the same pathogen, if one or more positive results were obtained for a serum, the patient was considered as positive.

B/ Results

Determination of Sera and Antigen Concentrations

In order to optimize the microarray assay, we performed different experimental conditions allowing the best ratio of "antigen-antibody". For each germ, a range of concentration from 1 to 16 µM of each antigen or 10-400 µg/mL lysate was first spotted onto the MIP protein microarray. Then, hybridization with different concentrations of serum IgG (from 12.5 to 800 µg/mL), as well as different concentrations of labelled secondary antibody (from 0.1 to 4 µg/mL, dilutions 1/250 to 1/10000) were tested in different pads of the same protein array. Detection of antibodies against EBV was performed using two major antigens: Epstein-Barr Nuclear Antigen (EBNA) and Viral Capsid Antigen (VCA). Examples of results obtained are shown in FIG. 2. The concentrations used ranged from 92 to 736 µg/mL for EBNA (FIG. 2A), from 32 to 258 µg/mL for glycoprotein B of CMV (FIG. 2B) and from 22.5 to 220 µg/mL for the core protein of HCV (FIG. 2C). For EBNA, CMV and HCV, the intensity of the fluorescent signal was too low when antigen concentration was 1 µM, and when IgG serum concentrations were less than 50 µg/mL.

For CMV, the inventors tested different antigens including glycoprotein B, and also virus lysates. FIG. 2B shows the fluorescence signals obtained with a CMV-positive serum used at different concentrations of IgG.

For HCV, the inventors tested three different antigens (core protein, NS-3 and NS-4). FIG. 2C shows the florescence obtained for HCV core protein with a positive serum. For the 4 germs, the intensity of the fluorescence signal increased with the concentration of antigen and IgG. The data obtained allowed us to define that the most suitable quantity of IgG to be used per pad was 100 to 400 µg/mL (8 to 32 µg/80 µL). Table 1 presents the optimal concentrations of antigens and lysates to be used for spotting and subsequent hybridization, in order to compare serological status determined by Elisa and by MIP. The final IgG concentration for hybridization was 400 µg/mL (32 µg/80 µL per pad), and the final secondary antibody concentration for detection was 0.2 µg/mL (dilution 1/5000).

TABLE 1

Optimal concentration of antigens and lysates for the Epstein-Barr virus, Cytomegalovirus, *T. gondii*, Hepatitis C Virus used in MIP microarray assay.

| Infectious agent | Type | Protein | Concentrations |
|---|---|---|---|
| EBV | Antigen | EBNA | 8 μM |
|  |  | VCA | 32 μM |
| CMV | Lysate |  | 400 μg/mL |
|  | Antigen | Glycoprotein B | 8 μM |
|  | Mix 5 Ag | pp65, pp28, pp52, pp38 glycoprotein B | 16 μM |
|  | Lysate + mix 5 Ag |  | 200 μg/mL, 16 μM |
| *T. gondii* | Lysate |  | 400 μg/mL |
|  | Antigen | P24 | 12 μM |
| HCV | Antigen | Core | 16 μM |
|  |  | NS-3 | 16 μM |
|  |  | NS-4 | 16 μM |

TABLE 2

Results obtained with 70 sera analyzed by classical ELISAs (E) used routinely in hospital diagnostic laboratories, and by the MIP microarray immunoassay (MA)

| ID | Age | Sex | IgG (g/L) | EBV EBNA E | EBV EBNA MA | EBV VCA E | EBV VCA MA | CMV Lysate + 5 Ag mix E | CMV Lysate + 5 Ag mix MA | T. gondii Lysate + Ag E | T. gondii Lysate + Ag MA | HCV Core E | HCV Core MA |
|---|---|---|---|---|---|---|---|---|---|---|---|---|---|
| 1BOA | 25 | F | 6.7 | − | − | ± | + | − | − | NA | NA | − | − |
| 2DEE | 25 | M | 24.2 | ± | + | + | − | + (*) | − | NA | NA | − | − |
| 3DEC | 67 | F | 3.9 | ± | − | − | − | + | − | NA | NA | − | − |
| 4BIT | 36 | M | 11.7 | + | + | − | + | NA | NA | NA | NA | − | − |
| 5RYE | 34 | M | 8.9 | ± | − | − | − | − | − | NA | NA | − | − |
| 7ANM | 27 | F | 12.2 | NA | NA | NA | NA | − | − | NA | NA | − | − |
| 9OUC | 60 | F | 15.5 | + | + | + | + | + | + | NA | NA | − | + |
| 11CHI | 11 | M | 13.1 | NA | NA | NA | NA | NA | NA | NA | NA | − | − |
| 12LET | 28 | M | 12.2 | NA | NA | NA | NA | NA | NA | NA | NA | ++++ | + |
| 13LEG | 61 | M | 17.4 | NA | NA | NA | NA | NA | NA | NA | NA | + | + |
| 14DEM | 57 | F | 12 | NA | NA | NA | NA | NA | NA | NA | NA | + | + |
| 15XXA | 22 | M | 11 | ± | − | + | + | NA | + | NA | NA | − | − |
| 16MAH | 20 | F | 13.9 | + | + | + | + | +++ | + | + | + | − | − |
| 17GRN | 41 | M | 10.9 | NA | NA | NA | NA | +++ | + | NA | NA |  |  |
| 18ZOL | 47 | M | 12 | + | + | + | + | + | + | NA | NA | − | − |
| 19GUC | 30 | M | 8.6 | + | + | + | + | − | − | + | + | − | − |
| 20LED | 28 | M | 8.4 | + | + | + | + | − | − | NA | NA | NA | NA |
| 21GRP | 45 | F | 12.1 |  |  |  |  | + | + | NA | NA | NA | NA |
| 22BES | NA | NA | 8.8 | + | + | + | + | + | + | NA | NA | NA | NA |
| 23ROF | 48 | M | 3.5 | + | + | + | ± | + | + | NA | NA | − | − |
| 25GBX | 35 | F | 18.8 | NA | NA | NA | NA | NA | NA | NA | NA | + | + |
| 26DIA | 43 | F | 28.8 | NA | NA | NA | NA | NA | NA | NA | NA | + | + |
| 27 PAJ | NA | H | 33.1 | NA | NA | NA | NA | NA | NA | NA | NA | + | + |
| 28VAP | 46 | M | 10.8 | NA | NA | NA | NA | NA | NA | NA | NA | + | + |
| 29GIP | 42 | M | 9.1 | NA | NA | NA | NA | NA | NA | NA | NA | + | + |
| 30ROA | 63 | M | 16.1 | NA | NA | NA | NA | NA | NA | NA | NA | + | + |
| 31DIH | 43 | F | 23.8 | + | + | + | + | + | + | NA | NA | + | + |
| 32BRL | 49 | M | 10.2 | + | + | + | + | + | + | NA | NA | − | − |
| 33BEV | 50 | F | 7.7 | + | + | + | + | + | + | NA | NA | − | − |
| 34SAO | 71 | M | 16.7 | NA | NA | NA | NA | NA | NA | NA | NA | − | − |
| 35POL | 20 | F | 4.7 | NA | NA | NA | NA | NA | NA | − | − | − | − |
| 36SHM | 37 | F | 8.9 | NA | NA | NA | NA | NA | NA | − | − | ++++ | + |
| 37 HEC | 59 | M | 5.4 | + | + | + | + | − | − | + | + | − | − |
| 38CHH | 24 | M | 10.4 | + | + | + | + | + | + | + | + | − | − |
| 39DUT | 34 | M | 4.4 | + | + | − | + | − | − | + | + | − | − |
| 40MUB | 32 | M | 7.7 | NA | NA | NA | NA | + (**) | + | − | − | − | − |
| 41SEE | 24 | F | 4.9 | NA | NA | NA | NA | NA | NA | − | − | − | − |
| 42KAM | 51 | M | 7.9 | + | + | + | + | + | + | NA | NA | − | − |
| 43LEA | 36 | F | 6.9 | NA | NA | NA | NA | NA | NA | − | − | NA | NA |
| 44MAC | 40 | M | 11.1 | + | + | + | + | + (***) | + | NA | NA | − | − |
| 45HUA | 17 | F | 10.9 | − | − | + | + | − | − | NA | NA | − | − |
| 46REE | 45 | M | 14.5 | + | + | + | + | + | + | NA | NA | − | − |
| 47DEC | 7 | F | 9.1 | − | − | − | − | − | − | − | − | NA | NA |
| 48DOD | 34 | F | 11.5 | NA | NA | NA | NA | NA | NA | + | + | − | − |
| 49TEO | 33 | M | 22.1 | + | + | + | + | − | − | + | + | − | − |
| 50BAM | 32 | F | 10.4 | NA | NA | NA | NA | NA | NA | + | + | NA | NA |
| 51MIM | 53 | F | 10.5 | + | + | + | + | + | + | + | + | − | − |
| 52HAK | 26 | M | 12.8 | + | + | + | + | − | − | + | + | − | − |
| 53BEK | 35 | F | 6.1 | + | + | + | + | + | + | + | + | − | − |
| 54CHG | 73 | M | 8.3 | + | + | + | + | − | − | + | + | − | − |
| 55SAS | 34 | F | 7.9 | NA | NA | NA | NA | + | + | + | + | − | − |

TABLE 2-continued

Results obtained with 70 sera analyzed by classical ELISAs (E) used routinely in hospital diagnostic laboratories, and by the MIP microarray immunoassay (MA)

| | | | | EBV | | | | CMV Lysate + 5 | | T. gondii Lysate + | | HCV | |
|---|---|---|---|---|---|---|---|---|---|---|---|---|---|
| | | | | EBNA | | VCA | | Ag mix | | Ag | | Core | |
| ID | Age | Sex | IgG (g/L) | E | MA | E | MA | E | MA | E | MA | E | MA |
| 56SAO | 22 | F | 18.9 | NA | NA | NA | NA | NA | NA | − | − | − | NA |
| 58ZOK | 27 | M | 11.1 | NA | NA | NA | NA | NA | NA | NA | NA | − | NA |
| 59LEB | 47 | M | 8.1 | + | + | + | + | + | + | NA | NA | − | − |
| 60COY | 61 | F | 6.4 | + | + | + | + | − | − | NA | NA | − | − |
| 61CLJ | 59 | M | 7.6 | ± | + | + | + | − | − | NA | NA | − | − |
| 62PAC | 43 | M | 12.8 | + | + | + | + | + | + | − | − | − | − |
| 63MAJ | 37 | M | 13.3 | + | + | + | + | + | + | − | + | − | − |
| 64ABR | 60 | M | 8.41 | + | | + | | − | − | + | + | − | − |
| 65DIA | 53 | F | 17.5 | + | + | + | + | + | + | + | + | − | − |
| 66YAH | 36 | F | 15.1 | NA | NA | NA | NA | NA | NA | + | + | − | − |
| 67SOD | 24 | F | 10.6 | NA | NA | NA | NA | NA | NA | + | + | − | − |
| 68CHC | 32 | F | 10.1 | NA | NA | NA | NA | NA | NA | + | + | NA | NA |
| 69MEN | 21 | M | 14.9 | + | + | + | + | + | + | + | + | − | − |
| 70BIA | 31 | F | 13.2 | NA | NA | NA | NA | NA | NA | + | + | − | − |
| 71TER | 57 | M | 22.5 | + | − | − | − | − | − | + | + | − | − |
| 72TAH | 29 | F | 12.0 | + | + | + | + | + | + | + | + | NA | NA |
| 73PAD | 66 | M | 6.8 | + | + | + | + | − | − | + | + | − | − |
| 74LEC | 49 | F | 14.3 | + | + | + | + | + | + | NA | NA | − | − |
| 75THF | 44 | F | 14.1 | + | + | + | + | − | − | + | + | + | + |

E: ELISA;
MA: Array;
NA: Not available,
±: involve patients with results near the detection threshold),
(*): past infection;
(**): low;
(***) recent infection.

Analysis of Serum Reactivity Against Arrayed Antigens

The inventors assessed the antibody reactivity of the 70 human sera against EBV, CMV, T. gondii, and HCV (a summary of the serological characteristics of patients is presented in Table 2). The data shown are representative of three experiments, independently performed.

Each serum was tested three times for each germ. FIGS. 3 to 5 present results obtained for EBV, CMV, T. gondii and HCV for a representative selection of ten patients. Fluorescence scanning of microarray slides incubated with representative sera of the different groups of patients showed that the MIP microarray assay allows the detection of antibodies specifically directed against microbial antigens in accordance with ELISA results (Tables 3 and 4).

TABLE 3

Discordant results between ELISA and MIP microarray immunoassay.

| | | | | EBV | | | | CMV Lysate + mix 5 Ag | | T. gondii Lysate + Ag | |
|---|---|---|---|---|---|---|---|---|---|---|---|
| | | | IgG | EBNA | | VCA | | | | | |
| Pt ID | Age | Sex | (g/L) | E | MA | E | MA | E | MA | E | MA |
| 1BOA | 25 | F | 6.7 | − | − | ± | + | − | − | ND | ND |
| 2DEE | 25 | M | 24.2 | ± | + | + | − | + | − | ND | ND |
| 3DEC | 67 | F | 3.9 | ± | − | − | − | + | − | ND | ND |
| 4BIT | 36 | M | 11.7 | + | + | − | + | ND | ND | ND | ND |
| 5RYE | 34 | M | 8.9 | ± | − | − | − | − | − | ND | ND |
| 15XXA | 22 | M | 11 | ± | − | + | + | ND | ND | ND | ND |
| 37HEC | 59 | M | 5.4 | + | + | + | + | − | − | + | − |
| 39DUT | 34 | M | 4.4 | + | − | + | − | − | − | + | + |
| 55SAS | 34 | F | 7.9 | ND | ND | ND | ND | + | − | + | − |
| 61CLJ | 59 | M | 7.6 | ± | + | + | + | − | − | ND | ND |
| 63MAJ | 37 | M | 13.3 | + | + | + | + | + | + | − | + |
| 71TER | 57 | M | 22.5 | + | − | − | − | − | − | + | + |

Age, sex, Ig G concentration and results of EBV, CMV and T. gondii ELISA (E) and MIP microarray (MA) for each patient presenting a discordant result.
Pt: patient;
±: results near the detection threshold;
ND: not done.

For EBV, the presence of IgG against the two antigens EBNA and/or VCA antigens was determined by the two techniques on sera obtained from 42 patients. For EBNA the same 32 patients were found positive, and the same 3 patients were found negative, by ELISAs and by MIP microarray. Five patients were classified uncertain by ELISA (considered "borderline" with the detection limit). Among these 5 patients, 3 were found negative and two were found positive by MIP microarray. For two patients the detection of IgG against EBNA was positive by ELISA and negative by MIP microarray. One presented with a high concentration of IgG directed against the varicella-zoster virus (VZV), suggesting that a false positivity due to EBV/VZV cross reactivity was possible. For the other patient presented a high level of IgG (22.5 g/L) and this patient was found negative for VCA of EBV by ELISA and MIP microarray. For VCA, 3/35 patients showed discordant results; 2 were found positive using ELISA and negative using MIP microarray. The patient with a high concentration of antibodies directed against VZV was also discordant for EBNA. The other patient presented with a high concentration of IgG (24 g/L); for this patient the detection of antibodies against EBNA was uncertain by ELISA and positive using MIP microarray. For one patient, the inventors found a positive detection of IgG against VCA using the multiplexed protein microarray and negative results using ELISA. For this patient, the detection of IgG directed against EBNA was positive by both ELISA and MIP microarray, suggesting a greater sensitivity for VCA for the MIP microarray (Table 3).

For CMV, 3/44 patients were found discordant using the two techniques: these patients had positive results by ELISA and negative results by MIP microarray (see table 3). For 1 patient, a similar discordance was found for $T.\ gondii$ (positive ELISA and negative MIP microarray). Considering the two other patients with positive ELISA and negative MIP microarray tests, one presented a high serum IgG concentration (23 g/L), and the other a low concentration of IgG in serum (3.9 g/L) (table 3).

For $T.\ gondii$, results were discordant for 3/33 patients. Two patients who were found positive by ELISA were found negative by MIP microarray. For these 2 patients, the IgG concentration was lower than 8 g/L. One of the patients was also negative for CMV by MIP microarray but positive by ELISA.

One patient was found positive by MIP microarray and negative by ELISA. For the patient with a very low level of IgG directed against $T.\ gondii$ when tested by ELISA, serum should be used less diluted to obtain a positive result by MIP microarray. Nonlinear relationship was evident and suggested the presence of a "hook effect". Under specific conditions, a high analyte concentration can simulate false negative signals (Table 4).

For HCV, 60 patients were compared using the two techniques. There was no discordance between ELISA and MIP microarray results. The 48 sera found negative by ELISA were also negative using the MIP microarray technique, and the 12 sera found positive by ELISA were also positive using the MIP microarray assay. Hence the MIP microarray had excellent sensitivity (100%) and specificity (100%) for the detection of anti-HCV IgG.

The two methods, MIP microarray and ELISA assays, were compared using the Chi-squared test on discordant results (+/− and −/+). No statistical difference was found: values were 0, 0.57, 1.73 and 0.57 for EBNA, VCA, CMV and $T.\ gondii$, respectively (Table 4).

TABLE 4

Agreement rate between results obtained assessing serum IgG reactivity by ELISA and by MIP microarray assay.

|  |  | A | B | C | D | E | F | Agreement (%) |
|---|---|---|---|---|---|---|---|---|
| Elisa |  | + | − | ± | ± | + | − |  |
| MIP |  | + | − | − | + | − | + |  |
| EBV | EBNA + VCA | 35 | 1 | 2 | 1 | 2 | 0 | 95 |
|  | EBNA | 31 | 3 | 3 | 2 | 2 | 0 | 94 |
|  | VCA | 33 | 4 | 0 | 1 | 2 | 1 | 92.5 |
| CMV |  | 24 | 17 | 0 | 0 | 3 | 0 | 93 |
| $T.\ gondii$ |  | 22 | 8 | 0 | 0 | 2 | 1 | 91 |
| HCV |  | 12 | 48 | 0 | 0 | 0 | 0 | 100 |

Results are given as numbers of concordant results: A, positive ELISA and positive MIP array; B, negative ELISA and negative MIP array; and discordant results: E, positive ELISA and negative MIP array; F, negative ELISA and positive MIP array. C and D were available only for EBV (EBNA and VCA), for which ELISA gave a result near the detection threshold (±) and the MIP array gave either a positive (C) or a negative (D) result. The % agreement for each germ was calculated on concordant results; the Chi-squared test performed on discordant patients was not significant for EBV, CMV, and $T.\ gondii$.

Analysis of Mc Ig Specificity with the MIP Microarray Assay

The inventors tested the suitability of the EBV/CMV/$T.\ gondii$/HCV microarray assay for analysis of the specificity of purified mc Igs. Sera and purified mc Igs of 3 HCV-positive patients presenting with either myeloma (2 patients) or MGUS (1 patient) were tested. For both serum and purified mc Ig, the MIP microarray showed specific detection of a single HCV antigen, either the core protein (2 patients) or NS-4 (1 patient) (FIG. 5).

C/ Discussion

The inventors showed that the MIP microarray assay can be used to detect the presence of IgG directed against various infectious epitopes in human sera. The MIP microarray allows the generation of high quality fluorescence signals suitable for the determination of serological status of patients for EBV, CMV, $T.\ gondii$ and HCV. Agreement between results obtained by ELISAs and the MIP microarray assay was 95% for EBV, 93% for CMV, 91% for $T.\ gondii$, and 100% for HCV. For EBV, CMV and $T.\ gondii$, discordance was most often due to a positive ELISA and negative MIP microarray assay. However, among the 5 sera found uncertain for EBNA by ELISA, the MIP microarray found 3 positive. Hence the MIP assay uses lesser volumes and is as sensitive as ELISAs and more sensitive than ELISA for anti-EBNA antibody detection. Regarding EBV, the detection of two types of antibodies minimized the risk of false negativity of false positivity: combining EBNA and VCA results, there was only one "false negative" serum by MIP microarray. Comparison of the MIP microarray and the ELISA assays on discordant results showed no statistical difference.

Altogether these results highlight the importance of IgG concentration: in all cases in cases with discordant results, the IgG concentration was outside of normal values, most often high. For the ELISA technique, plasma samples are used at fixed volume and dilution, without taking the IgG level into account. In contrast, for the MIP microarray assay, a dilution is performed for each sample so as to obtain 400

µg/mL IgG, deposited on a pad. For instance one patient with a positive ELISA assay but negative MIP microarray result for *T. gondii* was tested again on the MIP microarray using a higher dilution of sample (200 µg/mL µg of IgG instead of 400 µg/mL), this time with positive result. This is consistent with a "hook effect" for sera with high levels of specific antibodies. Thus, in order to avoid false negative results, it is advisable to test plasma samples at two Ig concentrations: 200 and 400 µg/mL.

It is worth noting that the EBV/CMV/*T. gondii*/HCV MIP microarray was found suitable to study the anti-infectious specificity of mc Ig. This is of importance since mc Ig can be specific for infectious antigens, as demonstrated for HCV-infected MGUS or myeloma patients whose mc Ig are directed against HCV proteins. The EBV/CMV/*T. gondii*/HCV MIP microarray detected the HCV specificity of mc Ig from 3/3 HCV-infected patients. For the purpose of analyzing mc Ig specificity, the MIP microarray presents the advantage of allowing simultaneous analysis against several germs with very small amount and volume of purified mc Ig.

As an ever-increasing variety of microarray formats becomes available (patterned microarrays, three-dimensional pads, flat surface spot microarrays), these versatile tools will be more and more used in high-throughput functional genomics and proteomics. Those results demonstrate that this test format has important advantages, and that reliable and reproducible analytical and clinical data can be obtained with microarrays. The novel EBV/CMV/*T. gondii*/HCV microarray assay is a suitable alternative assay for simultaneous serodiagnostics of infectious diseases in small volume samples in a clinical context. In the future, the design of the MIP microarray can be completed by the addition of more antigens and lysates of new viruses, bacteria or parasites.

This approach presents a wide range of potential applications for epidemiologic research as well as for the diagnosis of infectious diseases.

In conclusion, a major novel aspect of the MIP microarray assay resides in the combination of epitopes from a selection of infectious agents known to cause chronic infection, to be used for the diagnostic work-up of patients with a variety of diseases linked to chronic infection such as allergies, inflammatory diseases, auto-immune diseases or chronic monoclonal gammapathies. The MIP microarray assay with EBV, CMV, *T. gondii* and HCV antigens will allow testing patients with a single assay rather than a series of ELISAs. This is particularly interesting for biological samples typically available only in small volumes, such as purified mc Igs or cerebrospinal fluid.

The microarray test format should become in the near future a tool of choice for rapid diagnosis of infectious diseases and pathologic conditions linked to infection, as well as for the characterization of the infectious specificity of mc Ig.

Example 2

A/ Methods

Patients, Samples, and Mc Ig Purification

After informed consent, serum was obtained from patients diagnosed with MGUS or myeloma in different centers: Nantes, Dijon, Paris. Serum samples were aliquoted and kept at −20° C. until analysis. The presence and type of mc Ig was verified using serum electrophoresis onto agarose gel and immunofixation A homogeneous spike-like peak in a focal region of the gamma-globulin zone indicates a monoclonal gammopathy (FIG. 6). The mc Ig was purified using modification of serum electrophoresis ie elution from agarose gel electrophoresis of the zone corresponding of the mc Ig in the gamma globulin migration, then elution from into PBS and then the purity of purified mc Ig is verified using isoelectofocalisation and immunoblotting as previously described (Bigot-Corbel E. et al., Blood 2008; 112: 4357-4358; Féron D. Et al. Analytical Biochem 2013; 433: 202-209).

Selected Antigens and Lysates

Antigens (Ag) were supplied by Abcam (Cambridge, United Kingdom), Advanced Biotechnologies Inc. (Columbia, Md., USA), Virogen (Watertown, Mass., USA), EastCoast Bio (North Berwick, USA). Lysates were supplied by Advanced Biotechnologies Inc. (Columbia, Md., USA), EastCoast Bio (North Berwick, USA).

For EBV the three antigens have been used: Viral Capside Antigen (VCA) p23 (ref. ab43145, Abcam), p23 region 1-162aa (ref. 00211-V, Virogen) and Epstein-Barr Nuclear Antigen (EBNA) recombinant protein EBNA-1 (ref. 10-523-001, Advanced Biotechnologies).

For CMV, a mixture of five antigens has been used: region 297-510 of CMV pp65 IE (ref. ab54103, Abcam); CMV pp28 (UL99) immunodominant region (ref. ab43038, Abcam); CMV pp52 (UL44) immunodominant region (ref. ab43044, Abcam); glycoprotein B immunodominant region (ref. ab43040, Abcam); and CMV pp38 (UL80a) immunodominant region (ref. ab73042, Abcam) as well as a purified viral lysate (ref. 10-144-000, Advanced Biotechnologies).

For *T. gondii*, one antigen have been used, p24 (GRA1) protein (ref. ab43137, Abcam) and a purified tachyzoite lysate (ref. 10-279-001, Advanced Biotechnologies).

For HCV, three antigens have been used: core protein composed of 119 aa (1-119) (ref. ab49015, Abcam); NS-3 protein recombinant fragment subtype 1c (1192-1459 aa) (ref. ab91395, Abcam) and NS-4 recombinant mosaic protein containing the HCV NS-4 immunodominant regions aa1691-1710, aa1712-1733, aa1921-1940 from genotypes 1, 2, 3, 5 (ref. ab49027, Abcam).

For *Helicobacter pylori* (*H. pylori*), one antigen extract (ref. FC 509, EastCoast Bio) and one bacterial lysate (ref. FC504, East Cost Bio) have been used.

For Herpes Simplex Virus 1 (HSV1), two antigens were used: HSV1 gD immunodominant regions (ref.ab43045, Abcam) and HSV-1 gG immunodominant regions (ref.ab43048, Abcam) as well as purified viral lysate (ref.10-145-000, Advanced Biotechnologies).

For Herpes Simplex Virus 2 (HSV2), two antigens have been used: HSV-2 gD immunodominant regions with 33aa (266-39) (ref.ab48971, Abcam) and aminoacids 525-578 of HSV2 gG Envelope Protein (ref.ab67703, Abcam) as well as purified viral lysate (ref.10-146-000, Advanced Biotechnologies).

For Varicella Zoster Virus (VZV), two antigens have been used: one contains immunodominant regions of protein gE and the other immunodominant regions of ORF26. Some antigens contain histidine-tag or glutathione S-transferase (GST) fusion proteins. Before being printed, the adequate concentration range of each antigen and lysate was determined. For this purpose, antigens were diluted in PBS from 1 to 16 µM, and lysates were diluted from 10 to 500 µg/mL. Lysates were ultra-sonicated prior to dilution to avoid aggregates.

Preparation of the 8-Germs MIP Microarray

Ag (10 µL, 1-16 µM) or lysate (10 µL, 10-400 µg/mL) solutions were pipetted in 384-well microtiter plates (Porvair Sciences Ltd., Shepperton, United Kingdom). Then, samples were transferred onto FAST slides 16 pad of nitrocellulose (Whatman, Maidstone, United Kingdom) using the sciFLEX ARRAYER S3 Piezo Electric Dispenser (Scienion, Berlin—Germany). In all cases 6 drops were printed; each drop is estimated to contain 500 µL. Ag, tag, fusion proteins and negative controls were also spotted. The arrays consisted of 8×8 matrices that included: (i) thirteen Ags: 2 for EBV, 3 for HCV, 1 for *T. gondii*, 1 for *H. pylori*, 2 for HSV1, 2 for HSV2, 2 for VZV; (ii) five lysates (CMV, *T. gondii*, *H. pylori*, HSV1, HSV2); (iii) mix of five Ag; (iv) two tag controls (GST, histidine); (v) one negative control (PBS) (FIG. 7). Spotting was performed inside a chamber at 25° C. and 60% humidity.

Processing of Microarray Slides

Printed slides were saturated for 1 hour at room temperature with T-PBS and 5-10% BSA in order to prevent non-specific Ab binding. After washing with TPBS, slides were incubated with 80 µL of diluted serum (100 to 800 µg/mL) or purified mc Ig (12.5 to 200 µg/mL), for two hours at room temperature. After a second washing, slides were incubated with a labelled secondary Ab (0.1 to 4 µg/mL) of Dylight™ 680-labelled goat anti-human IgG (H+L) (Kirkegaard & Perry Laboratories Inc., Gaithersburg, Md., USA) or Dylight™ 680 goat anti-human IgA from antibodies-online or monoclonal antibody to lambda light chains Alexa Fluor® 700-conjugated (Exbio, Czech Republic) or goat anti-human kappa chains Alexa Fluor® 700-conjugated (Invitrogen, Belgium) while shaking in the dark, then washed with T-PBS. Fluorescence signal, detected with the Odyssey infrared imaging system scanner at 21 µm resolution (LI-COR Biosciences, NE, USA) was used to determine the serological status of each sample.

Data Analysis

Specific fluorescence was quantified using the GenePix® Pro 4 Microarray Acquisition & Analysis Software (Molecular Devices, Sunnyvale, Calif., USA). For each sample, the median fluorescence intensity (FLU) was determined after subtraction of background slide fluorescence. Results for each sample (patients and controls) were represented on histograms using GraphPad 5.0 software (San Diego, Calif., USA). FLU values represent the mean of four replicates from one experiment. Experiments were repeated three times on different arrays for each patient. FLU values obtained for each sample were compared to positive and negative commercial controls for each germ. For each antigen, the positivity threshold was the mean plus 2 standard deviations of fluorescence values obtained for the negative control for each germ. Patients or whom the mean FLU value was higher than the positivity threshold were considered as positive for the antigen tested. When several antigens were used for the same pathogen, if one or more positive results were obtained for a serum, the patient was considered as positive.

Western Blot Analysis

The MP Diagnostics (MPD) HELICO BLOT 2.1 Western Blot kit assay consists of a Western Blot made from bacterial lysate of *H. pylori* strain ATCC 49503 and a recombinant antigen called CIM. The test strip contains *H. pylori* antigens with molecular weights of 116 kDa (CagA), 89 kDa (VacA), 37 kDa, 35 kDa, 30 kDa (Urease A), and 19.5 kDa as separate lines. The CIM had been originally identified by screening of immunogenic proteins of *H. pylori* and was synthesized by recombinant technology. The test was done and interpreted according to instructions of the manufacturer. Patient sera were diluted at 1/60. Mc Ig were concentrated at 0.025-0.05 g/L. Diluted and non-diluted sera and purified mc Igs were incubated with the strips according to instructions of the manufacturer. The manufacturer's recommended criteria for determining *H. pylori* positivity by Helico Blot 2.1 were as follows:

(1) 116 kDa (CagA) positive, where CagA has to be present with at least one of the following bands—89 kDa (VacA), 37 kDa, 35 kDa, 30 kDa (UreA), or 19.5 kDa, or with CIM, (2) presence of any one band at 89 kDa, 37 kDa, or 35 kDa, with or without CIM, (3) presence of both 30 kDa and 19.5 kDa band with or without CIM.

These criteria were used to validate the positivity of serum but not for mc Ig because we look for specificity for only one antigen.

B/ Results

Analysis of Mc Ig Specificity with the 8-Germ MIP Microarray Assay

It has been previously shown that mc Ig of patients who are infected with HCV typically recognize HCV core or NS4. Sera and purified mc Ig from 90 patients with myeloma or MGUS were analysed using the novel, 8-germ MIP microarray. For 59 patients with EBV-positive serum, mc Ig specifically recognized EBNA (Epstein Barr nuclear Ag) in 19% cases (FIG. 8), and for 25 patients with *H. Pylori*-positive serum, mc Ig was found specific for one *H. Pylori* antigen (CagA protein) in 8% of cases (FIG. 9).

Specificity of mc Ig for *H. pylori* CagA protein was confirm using western blot analysis.

In contrast, for 45 patients found positive for CMV, no CMV specificity was found for the mc Ig. For 38 patients found positive for HHV-1 or HHV-2, no HHV-1/2 specificity was found for the mc Ig. For 41 patients found positive for VZV, no VZV specificity was found for the mc Ig, and for 16 patients found positive for *T. gondii*, no *T. gondii* specificity was found for the mc Ig.

Altogether, for 23 of the 101 (22.8%) patients studied, the mc Ig was found specific for one Ag of these 3 germs: HCV, EBV, *H. pylori*. Using the 8 germ MIP array immunoassay, in the cohort studied, no patient was found to have a mc Ig directed at Ag from CMV, HHV-1, HHV-2, VZV, or *T. gondii*. In this series, 20.6% of MGUS and 24.2% of myeloma patients (non significant difference, p=0.810) present with a mc Ig that is directed against HCV, EBV or *H. pylori*.

C/ Discussion

This study is the first systematic analysis of the specificity of mc Ig of MGUS and myeloma patients. The MIP array immunoassay designed for this study is uniquely suited to successfully analyse the specificity of mc Ig: prior to the protein array technology, screening mc Ig for a panel of Ag using classical assays such as ELISAs required large quantities of purified mc Ig, usually not available. The inventors found that antigens from three germs known to cause other B-cell malignancies (EBV, HCV, *H. pylori*) can be the targets of mc Ig of more than 20% of MGUS and myeloma patients. The exact proportion of patients with mc Ig specific for these three germs will have to be determined in large cohorts of MGUS and myeloma patients. In contrast, in the same cohort the inventors found no evidence that Ag from CMV, HHV-1, HHV-2 or VZV (all common germs) or *T. gondii* (less frequent) are targeted by mc Ig. Nevertheless, these observations will have to be confirmed in large cohorts of patients; these studies are on-going in the laboratory of the inventors.

These findings regarding HCV, EBV and *H. pylori* demonstrate that chronic antigen stimulation is a key step in the pathogenesis of MGUS and myeloma for subsets of patients, estimated in this first study to represent more than 20% of MGUS and myeloma patients. The inventors provide a new tool to stratify patients according to the antigen-specificity of mc Ig. This novel assay, based on the protein array technology, allows testing the specificity of minute amounts of purified mc Ig for up to 36 different Ag in a single assay. This technology is considerably more efficient for studies of mc Ig specificity than phage display, epitope reconstruction or epitope mediated antigen prediction (E-MAP), which all proved disappointing. Two reasons explain the paucity of results using these techniques: first, the technical complexity makes it difficult to use in clinical practice; second, these techniques are predictive only and it is necessary to confirm the specificity of mc Ig with other assays. The new array will allow the stratification of patients according to particular antigen-specificity of their mc Ig.

Indeed the Ag-specificity of mc Ig may be associated with specific patient characteristics, risk of disease progression or/and response to treatment, in view of personalized medicine in myeloma and MGUS. Indeed, differences and distinct disease evolution and response to treatment are observed among myeloma patients. Chronic stimulation by various categories of Ag can contribute to the diversity of clinical, biological and cytogenetic presentation, as well as the heterogeneity of response. New protocols taking antigen specificity of mc Ig into account could lead to curative treatment in MGUS and improved response to treatment in myeloma: treatment including antibiotics or antiviral drugs could cure subsets of MGUS and facilitate response to treatment in myeloma.

The invention claimed is:

1. A method for determining whether a Gammopathy of Undetermined Significance (MGUS) or myeloma is specific for an infectious agent, wherein said method comprises a protein microarray assay comprising:
   a) incubating a purified monoclonal immunoglobulin sample of the MGUS or myeloma patient with a protein microarray comprising (a) a substrate and (b) antigens immobilized on the substrate, said antigens comprising infectious agent antigens which comprise at least one virus-specific antigen and at least one bacteria-specific antigen, and
   b) detecting if said monoclonal immunoglobulin is bound to said antigens.

2. The method according to claim 1, wherein said infectious agent antigens further comprise at least one parasite-specific antigen.

3. The method according to claim 2, wherein said infectious agent antigen is:
   a virus specific antigen specific for an infectious agent selected from the group consisting of Hepatitis C virus (HCV), Epstein-Barr Virus (EBV), Hepatitis B virus (HBV), Human immunodeficiency virus (HIV), cytomegalovirus (CMV), varicella-zoster virus, HHV-1, HHV-2, HHV-6, HHV-8, coxsackie virus B4, influenza A and B viruses and Rubella virus and Measles virus, and/or
   a bacteria specific antigen specific for an infectious agent selected from the group consisting of Helicobacter pylori, Staphylococcus aureus, Streptococcus A, Chlamydia trachomatis, Mycoplasma pneumoniae, Haemophilus influenza, Borrelia burgdorferi; Bartonella Hensalae, Porphyromonas gingivalis and Prevotellaceae, and/or
   a parasite specific antigen specific for Toxoplasma gondii and Candida albicans.

4. The method according to claim 3, wherein said parasite specific antigen is a polypeptide comprising the amino acid sequence of SEQ ID NO: 6 or a variant or fragment thereof.

5. The method according to claim 1, wherein said virus-specific antigen is specific for an infectious agent selected from the group consisting of Hepatitis C virus (HCV) and Epstein-Barr Virus (EBV), and/or said bacteria-specific antigen is specific of Helicobacter pylori bacterium.

6. The method according to claim 1, wherein said virus specific antigen is a polypeptide comprising the amino acid sequence selected from the group consisting of SEQ ID NO: 1, SEQ ID NO: 2, SEQ ID NO: 3, SEQ ID NO:4, SEQ ID NO:5, SEQ ID NO: 7, SEQ ID NO: 8, SEQ ID NO: 9, SEQ ID NO: 10, SEQ ID NO 11, SEQ ID NO: 12, SEQ ID NO 13, SEQ ID NO: 14, SEQ ID NO: 15, SEQ ID NO: 16, SEQ ID NO: 17 SEQ ID NO: 18; SEQ ID NO: 39, SEQ ID NO: 40, SEQ ID NO: 41 SEQ ID NO: 42, SEQ ID NO: 43, SEQ ID NO: 44, SEQ ID NO: 45, SEQ ID NO: 46, SEQ ID NO: 47 SEQ ID NO: 51; SEQ ID NO:52 SEQ ID NO: 53, SEQ ID NO: 54, SEQ ID NO: 55, SEQ ID NO: 56; SEQ ID NO: 57, SEQ ID NO: 58 SEQ ID NO: 60, or a variant or fragment thereof.

7. The method according to claim 6, wherein said virus specific antigen is a polypeptide comprising the amino acids 1-300, 301-582, 583-1063, 301-534, 583-1028 or 1050-1063 of sequence SEQ ID NO 51 or the amino acids 1-1301 or 1302-2116 of sequence SEQ ID NO: 52 or a variant or fragment thereof.

8. The method according to claim 1, wherein said bacteria specific antigen is a polypeptide comprising the amino acid sequence selected from the group consisting of SEQ ID NO: 30, SEQ ID NO: 31, SEQ ID NO: 32 SEQ ID NO: 33, SEQ ID NO: 34, SEQ ID NO: 35 SEQ ID NO: 36, SEQ ID NO: 37, SEQ ID NO: 38, SEQ ID NO: 48, SEQ ID NO: 49, SEQ ID NO: 50, SEQ ID NO: 62, SEQ ID NO: 63, SEQ ID NO: 64, SEQ ID NO: 65 and SEQ ID NO: 66 and a variant or fragment thereof.

9. The method according to claim 1, wherein said infectious agent antigen is
- at least one HCV specific antigen comprising an HCV lysate and/or at least one polypeptide comprising a sequence selected from the group consisting of SEQ ID NO: 7, SEQ ID NO: 8, SEQ ID NO: 9, SEQ ID NO: 10, the amino acids 1192-1459 of SEQ ID NO: 11, SEQ ID NO 12, SEQ ID NO: 13, the amino acids 1691-1710 of SEQ ID NO: 13, the amino acids 1712-1733 of SEQ ID NO: 13, the amino acids 1921-1940 of SEQ ID NO: 13, a variant or fragment thereof,
- at least one EBV specific antigen comprising an EBV lysate and/or at least one polypeptide comprising a sequence selected from the group consisting of SEQ ID NO: 16, amino acid sequence 1-162 of SEQ ID NO: 15, a variant or a fragment thereof, and/or
- at least one *H. pylori* specific antigen comprising an *H. pylori* lysate and/or at least one polypeptide selected from the group consisting of SEQ ID NO: 62, SEQ ID NO: 63, SEQ ID NO: 64, SEQ ID NO: 65, SEQ ID NO: 66, a variant or a fragment thereof.

* * * * *